United States Patent
Lin et al.

(10) Patent No.: US 12,258,324 B2
(45) Date of Patent: Mar. 25, 2025

(54) FATTY ACID ANALOGUES AND METHODS OF USE

(71) Applicant: LIN BIOSCIENCE PTY LTD., San Diego, CA (US)

(72) Inventors: Yu-Hsin Tom Lin, San Diego, CA (US); Cheng-Chi Irene Wang, San Diego, CA (US); Jason Olejniczak, San Diego, CA (US)

(\*) Notice: Subject to any disclaimer, the term of this patent is extended or adjusted under 35 U.S.C. 154(b) by 0 days.

(21) Appl. No.: 17/055,550

(22) PCT Filed: May 15, 2019

(86) PCT No.: PCT/US2019/032506
§ 371 (c)(1),
(2) Date: Nov. 13, 2020

(87) PCT Pub. No.: WO2019/222414
PCT Pub. Date: Nov. 21, 2019

(65) Prior Publication Data
US 2021/0221781 A1    Jul. 22, 2021

Related U.S. Application Data

(60) Provisional application No. 62/672,414, filed on May 16, 2018.

(51) Int. Cl.
| | | |
|---|---|---|
| C07D 295/215 | (2006.01) | |
| A61K 9/00 | (2006.01) | |
| A61K 31/4725 | (2006.01) | |
| A61K 31/573 | (2006.01) | |
| A61K 38/13 | (2006.01) | |
| A61P 27/04 | (2006.01) | |
| C07C 275/26 | (2006.01) | |
| C07C 275/30 | (2006.01) | |
| C07C 311/32 | (2006.01) | |
| C07D 211/38 | (2006.01) | |
| C07D 211/48 | (2006.01) | |
| C07D 213/40 | (2006.01) | |
| C07D 237/20 | (2006.01) | |
| C07D 249/06 | (2006.01) | |
| C07D 257/04 | (2006.01) | |
| C07D 309/14 | (2006.01) | |
| C07D 487/04 | (2006.01) | |

(52) U.S. Cl.
CPC ........ *C07D 295/215* (2013.01); *A61K 9/0048* (2013.01); *A61K 9/0053* (2013.01); *A61K 31/4725* (2013.01); *A61K 31/573* (2013.01); *A61K 38/13* (2013.01); *A61P 27/04* (2018.01); *C07C 275/26* (2013.01); *C07C 275/30* (2013.01); *C07C 311/32* (2013.01); *C07D 211/38* (2013.01); *C07D 211/48* (2013.01); *C07D 213/40* (2013.01); *C07D 237/20* (2013.01); *C07D 249/06* (2013.01); *C07D 257/04* (2013.01); *C07D 309/14* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 5,338,858 A | 8/1994 | Devadas et al. | |
| 5,846,514 A | 12/1998 | Foster et al. | |
| 6,334,997 B1 | 1/2002 | Foster et al. | |
| 6,531,477 B1* | 3/2003 | Markwalder | C07D 471/04 514/303 |
| 7,714,014 B2* | 5/2010 | He | A61P 35/00 514/403 |
| 7,744,910 B2* | 6/2010 | Gschneidner | A61P 19/10 514/9.9 |
| 8,790,927 B2* | 7/2014 | Park | A61K 36/13 435/410 |
| 2005/0164951 A1 | 7/2005 | Hammock et al. | |

FOREIGN PATENT DOCUMENTS

| | | | | |
|---|---|---|---|---|
| WO | WO 99/54321 | * | 4/1999 | ......... C07D 295/182 |
| WO | WO2009/086429 A1 | | 7/2009 | |
| WO | WO2014078895 A1 | | 5/2014 | |
| WO | WO2019016293 A1 | | 1/2019 | |

OTHER PUBLICATIONS

Database Registry Chemical Abstracts Service, Columbus, Ohio, Accession No. RN 495-69-2, Entered STN: Nov. 16, 1984.*
Database Registry Chemical Abstracts Service, Columbus, Ohio, Accession No. RN 1247546-61-7, Entered STN: Oct. 27, 2010.*
Database Registry Chemical Abstracts Service, Columbus, Ohio, Accession No. RN 344578-02-5, Entered STN: Jul. 5, 2001.*
Berge et al.: Pharmaceutical Salts. Journal of Pharmaceutical Science. 66:1-19 (1997).
Bundgaard et al. Design of Prodrugs pp. 7-9, 21-24 (1985).
Higuchi et al. Pro-drugs as Novel Delivery Systems, vol. 14 of the A.C.S. Symposium Series; and in Bioreversible Carriers in Drug Design, ed. Edward B. Roche, American Pharmaceutical Association and Pergamon Press (1987).
PCT/US2019/032506 International Preliminary Report on Patentability dated Nov. 17, 2020.
PCT/US2019/032506 International Search Report and Written Opinion dated Sep. 10, 2019.

(Continued)

*Primary Examiner* — Samantha L Shterengarts

(57) ABSTRACT

Provided herein are compounds, pharmaceutical compositions, and methods of treatment for various diseases or conditions, such as cancer. In one aspect, the method comprises the treatment of metastatic cancers. Compounds and methods provided herein are also used for the treatment of diseases such as inflammatory disease, cardiovascular disease, autoimmune disease, and dry eye syndrome. Further provided herein are dietary supplement formulations and methods for supporting a healthy lifestyle.

15 Claims, No Drawings

(56) References Cited

OTHER PUBLICATIONS

Pubmed Compound Summary for CID 151922. 12-Phenyldodecanoic acid. U.S. National Library of Medicine. 33 pages (2005) https://pubchem.ncbi.nlm.nih.gov/compound/151922).

Pubmed Compound Summary for CID 22978774. '12-[(Cyclohexylcarbamoyl)amino]dodecanoic acid. U.S. National Library of Medicine. 30 pages (2007) https://pubchem.ncbi.nlm.nih.gov/compound/22978774.

* cited by examiner

FATTY ACID ANALOGUES AND METHODS OF USE

CROSS-REFERENCE

This application claims the benefit of U.S. provisional patent application No. 62/672,414 filed on May 16, 2018, which is incorporated herein by reference in its entirety.

BACKGROUND

A need exists in the medicinal arts for the effective treatment of diseases, such as cancer, inflammatory disease, cardiovascular disease, autoimmune disease, and dry eye syndrome. Additionally, supplements comprising compounds capable of supporting a healthy lifestyle are needed.

BRIEF SUMMARY OF THE INVENTION

Provided herein are compounds and methods for the treatment of proliferative diseases, such as cancer, inflammatory disease, cardiovascular disease, autoimmune disease, and dry eye syndrome. In some embodiments, the cancer is a metastatic cancer. Further disclosed herein are dietary supplement formulations and methods. These formulations and methods can be useful for helping individuals, among other things, to support a healthy lifestyle.

Some embodiments provided herein describe a compound, or a pharmaceutically acceptable salt, solvate, or stereoisomer thereof, having the structure of Formula (I):

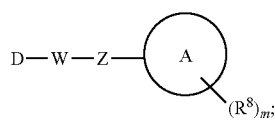

Formula I wherein:
D is —$CO_2H$, —$C(=O)NR^7R^9$, or tetrazolyl;
W is —$(CH_2)_p$-$(L)_n$-$(CH_2)_q$—;
each L is independently —$(CR^1R^2)$—, —O-alkylene-, —$NR^7$-alkylene-, —S-alkylene-, —$S(=O)$-alkylene, —$S(=O)_2$-alkylene, or —Se-alkylene-;
Z is a bond, —$NR^3C(=O)NR^4$—, —$NR^3C(=O)$—, —$NR^3C(=O)NR^4$-alkylene-, —$NR^3C(=O)$-alkylene-$NR^4$—, —$NR^3C(=O)$-alkylene-, —$NR^3S(=O)_2$—, —$S(=O)_2NR^3$, —$NR^3S(=O)_2$-alkylene-, —$NR^3S(=O)_2$-alkylene-$NR^6$—, —$S(=O)_2NR^3$-alkylene-, —$S(=O)_2$—, —$(C_1$-$C_3$ heteroaryl)-, —$NR^3C(=O)$-alkylene-O—, —$NR^3C(=O)$-alkylene-S—, or —OC$(=O)NR^4$—;
Ring A is optionally substituted aryl, optionally substituted heteroaryl, optionally substituted $C_2$-$C_8$ heterocycloalkyl, or optionally substituted $C_3$-$C_8$ cycloalkyl;
each $R^1$ or $R^2$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)$$NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, —$NR^cR^d$, or $R^1$ and $R^2$ are taken together to form a $C_1$-$C_6$ cycloalkyl or $C_1$-$C_6$ heterocycloalkyl, wherein both $R^1$ and $R^2$ on a single carbon are not hydrogen;
$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;
$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;
each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;
or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$;
$R^3$ is hydrogen, —$S(=O)R^b$, —$S(=O)_2R^d$, —$S(=O)_2NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;
$R^4$ is hydrogen, —$S(=O)R^b$, —$S(=O)_2R^d$, —$S(=O)_2NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;
$R^6$ is hydrogen, —$S(=O)R^b$, —$S(=O)_2R^d$, —$S(=O)_2NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

R$^7$ and R$^9$ are independently hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

each R$^8$ is independently hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

m is 1-5;
n is 0-3;
p is 0-9;
q is 0-5;
provided that the atom chain connecting D and Z is 11, 12, 13, or 14 atoms; and
provided that when A is

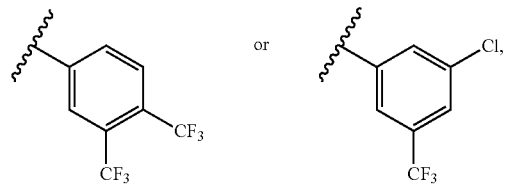 [SMILES: *c1ccc(C(F)(F)F)c(C(F)(F)F)c1 ; *c1cc(Cl)cc(C(F)(F)F)c1]

then
(i) D is not —CO$_2$H,
(ii) W is not —(CH$_2$)$_{12}$— or —(CH$_2$)$_{14}$—, or
(iii) Z is not —NHC(=O)NH—.

Certain embodiments provided herein provide for a compound, or a pharmaceutically acceptable salt, solvate, or stereoisomer thereof, having the structure of Formula (I):

Formula I

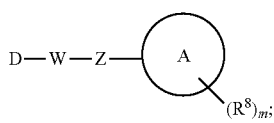

wherein:
D is —CO$_2$H, —C(=O)NR$^7$R$^9$, or tetrazolyl;
W is —(CH$_2$)$_p$-(L)$_n$-(CH$_2$)$_q$—;
each L is independently —(CR$^1$R$^2$)—, —O-alkylene-, —NR$^7$-alkylene-, —S-alkylene-, —S(=O)-alkylene, —S(=O)$_2$-alkylene, or —Se-alkylene-;

Z is a bond, —NR$^3$C(=O)NR$^4$—, —NR$^3$C(=O)—, —NR$^3$C(=O)NR$^4$-alkylene-, —NR$^3$C(=O)-alkylene-NR$^4$—, —NR$^3$C(=O)-alkylene-, —NR$^3$S(=O)$_2$—, —S(=O)$_2$NR$^3$, —NR$^3$S(=O)$_2$-alkylene-, —NR$^3$S(=O)$_2$-alkylene-NR$^6$—, —S(=O)$_2$NR$^3$-alkylene-, —S(=O)$_2$—, —(C$_1$-C$_3$ heteroaryl)-, —NR$^3$C(=O)-alkylene-O—, —NR$^3$C(=O)-alkylene-S—, or —OC(=O)NR$^4$—;

Ring A is optionally substituted aryl, optionally substituted heteroaryl, optionally substituted C$_2$-C$_8$ heterocycloalkyl, or optionally substituted C$_3$-C$_8$ cycloalkyl, wherein Ring A is not phenyl.

each R$^1$ or R$^2$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, —NR$^c$R$^d$, or R$^1$ and R$^2$ are taken together to form a C$_1$-C$_6$ cycloalkyl or C$_1$-C$_6$ heterocycloalkyl, wherein both R$^1$ and R$^2$ on a single carbon are not hydrogen;

R$^a$ is hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

R$^b$ is C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

each R$^c$ and R$^d$ is independently hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, C$_1$-C$_6$ alkyl, C$_1$-C$_6$ haloalkyl, —OH, —OMe, or —NH$_2$;

R$^3$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

R$^4$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

R$^6$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

R$^7$ and R$^9$ are independently hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each R$^8$ is independently hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

m is 1-5;
n is 0-3;
p is 0-9;
q is 0-5; and
provided that the atom chain connecting D and Z is 11, 12, 13, or 14 atoms.

In some embodiments of a compound of Formula (I), the compound has the Formula (Ia-1) or Formula (Ia-2), or a pharmaceutically acceptable salt, solvate, or stereoisomer thereof:

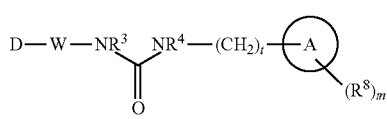

Formula (Ia-1)

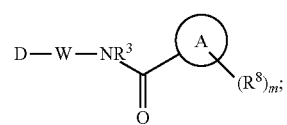

Formula (Ia-2)

wherein W is —(CH$_2$)$_p$-(L)$_n$(CH$_2$)$_q$—, and t is 0-2.

In some embodiments, a compound of Formula (I) has the Formula (Ib), or a pharmaceutically acceptable salt, solvate, or stereoisomer thereof:

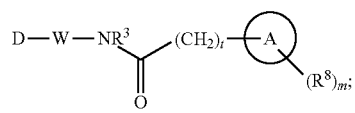

Formula (Ib)

wherein t is 0-2.

In some embodiments, a compound of Formula (I) has the Formula (Ic), or a pharmaceutically acceptable salt, solvate, or stereoisomer thereof:

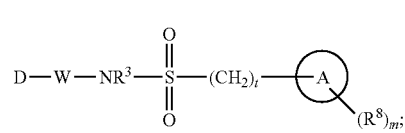

Formula (Ic)

wherein t is 0-2.

In some embodiments of a compound of Formula (I), Z is a bond. In some embodiments of a compound of Formula (I), Z is —NR$^3$C(=O)NR$^4$—. In some embodiments of a compound of Formula (I), Z is NR$^3$C(=O)NR$^4$-alkylene-. In some embodiments of a compound of Formula (I), Z is NR$^3$C(=O)NR$^4$—CH$_2$—.

In some embodiments of a compound of Formula (I), Z is —NR$^3$C(=O)-alkylene-NR$^4$—. In some embodiments of a compound of Formula (I), Z is —NR$^3$C(=O)—CH$_2$NR$^4$—. In some embodiments of a compound of Formula (I), Z is —(C$_1$-C$_3$ heteroaryl)-. In some embodiments of a compound of Formula (I), Z is triazolyl, tetrazolyl, furanyl, pyrrolyl, thiazolyl, oxazolyl, isoxazolyl, imidazolyl, pyrazolyl, thiadiazolyl, or oxadiazolyl. In some embodiments of a compound of Formula (I), Z is triazolyl. In some embodiments of a compound of Formula (I), Z is —NR$^3$C(=O)-alkylene-O—. In some embodiments of a compound of Formula (I), Z is —NR$^3$C(=O)—CH$_2$—O—. In some embodiments of a compound of Formula (I), Z is —OC(=O)NR$^4$—. In some embodiments of a compound of Formula (I), Z is —NR$^3$S(=O)$_2$-alkylene-NR$^6$—. In some embodiments of a compound of Formula (I), Z is —NR$^3$S(=O)$_2$—CH$_2$CH$_2$NR$^6$—.

In some embodiments of a compound of Formula (I), Formula (Ia-1), Formula (Ia-2), Formula (Ib) or Formula (Ic), D is —CO$_2$H. In some embodiments of a compound of Formula (I), Formula (Ia-1), Formula (Ia-2), Formula (Ib) or Formula (Ic), D is —C(=O)NR$^7$R$^9$. In some embodiments of a compound of Formula (I), Formula (Ia-1), Formula (Ia-2), Formula (Ib) or Formula (Ic), D is tetrazolyl.

In some embodiments of a compound of Formula (I), Formula (Ia-1), Formula (Ia-2), Formula (Ib) or Formula (Ic), $R^1$ and $R^2$ are independently hydrogen, $C_1$-$C_6$ alkyl, $C_3$-$C_8$ cycloalkyl, or $C_1$-$C_6$ haloalkyl.

In some embodiments of a compound of Formula (I), Formula (Ia-1), Formula (Ia-2), Formula (Ib) or Formula (Ic), $R^1$ and $R^2$ are independently hydrogen. In some embodiments of a compound of Formula (I), Formula (Ia-1), Formula (Ia-2), Formula (Ib) or Formula (Ic), $R^1$ and $R^2$ are hydrogen.

In some embodiments of a compound of Formula (I), Formula (Ia-1), Formula (Ia-2), Formula (Ib) or Formula (Ic), $R^3$ and $R^4$ are independently hydrogen, $C_1$-$C_6$ alkyl, $C_3$-$C_8$ cycloalkyl, or $C_1$-$C_6$ haloalkyl. In some embodiments of a compound of Formula (I), Formula (Ia-1), Formula (Ia-2), Formula (Ib) or Formula (Ic), $R^3$ and $R^4$ are independently hydrogen. In some embodiments of a compound of Formula (I), Formula (Ia-1), Formula (Ia-2), Formula (Ib) or Formula (Ic), $R^3$ and $R^4$ are H.

In some embodiments of a compound of Formula (I), Formula (Ia-1), Formula (Ia-2), Formula (Ib) or Formula (Ic), $R^6$ is hydrogen, $C_1$-$C_6$ alkyl, $C_3$-$C_8$ cycloalkyl, or $C_1$-$C_6$ haloalkyl. In some embodiments of a compound of Formula (I), Formula (Ia-1), Formula (Ia-2), Formula (Ib) or Formula (Ic), $R^6$ is hydrogen or $C_1$-$C_6$ alkyl. In some embodiments of a compound of Formula (I), Formula (Ia-1), Formula (Ia-2), Formula (Ib) or Formula (Ic), wherein $R^6$ is $CH_3$.

In some embodiments of a compound of Formula (I), Formula (Ia-1), Formula (Ia-2), Formula (Ib) or Formula (Ic), $R^7$ and $R^9$ are independently hydrogen, $C_1$-$C_6$ alkyl, $C_3$-$C_8$ cycloalkyl, or $C_1$-$C_6$ haloalkyl.

In some embodiments of a compound of Formula (I), Formula (Ia-1), Formula (Ia-2), Formula (Ib) or Formula (Ic), $R^7$ and $R^9$ are independently hydrogen, or $C_1$-$C_6$ alkyl. In some embodiments of a compound of Formula (I), Formula (Ia-1), Formula (Ia-2), Formula (Ib) or Formula (Ic), $R^7$ is H. In some embodiments of a compound of Formula (I), Formula (Ia-1), Formula (Ia-2), Formula (Ib) or Formula (Ic), $R^7$ is H or $CH_3$. In some embodiments of a compound of Formula (I), Formula (Ia-1), Formula (Ia-2), Formula (Ib) or Formula (Ic), $R^7$ and $R^9$ are H.

In some embodiments of a compound of Formula (I), Formula (Ia-1), Formula (Ia-2), Formula (Ib) or Formula (Ic), $R^8$ is hydrogen, halogen, $C_1$-$C_6$ alkyl, $C_3$-$C_8$ cycloalkyl, or $C_1$-$C_6$ haloalkyl. In some embodiments of a compound of Formula (I), Formula (Ia-1), Formula (Ia-2), Formula (Ib) or Formula (Ic), $R^8$ is halogen. In some embodiments of a compound of Formula (I), Formula (Ia-1), Formula (Ia-2), Formula (Ib) or Formula (Ic), $R^8$ is fluorine. In some embodiments of a compound of Formula (I), Formula (Ia-1), Formula (Ia-2), Formula (Ib) or Formula (Ic), $R^8$ is $C_1$-$C_6$ haloalkyl. In some embodiments of a compound of Formula (I), Formula (Ia-1), Formula (Ia-2), Formula (Ib) or Formula (Ic), $R^8$ is trifluoroalkyl. In some embodiments of a compound of Formula (I), Formula (Ia-1), Formula (Ia-2), Formula (Ib) or Formula (Ic), $R^8$ is trifluoromethyl.

In some embodiments of a compound of Formula (I), Formula (Ia-1), Formula (Ia-2), Formula (Ib) or Formula (Ic), L is —O-alkylene-. In some embodiments of a compound of Formula (I), Formula (Ia-1), Formula (Ia-2), Formula (Ib) or Formula (Ic), L is —S-alkylene-. In some embodiments of a compound of Formula (I), Formula (Ia-1), Formula (Ia-2), Formula (Ib) or Formula (Ic), L is —OCH$_2$CH$_2$—. In some embodiments of a compound of Formula (I), Formula (Ia-1), Formula (Ia-2), Formula (Ib) or Formula (Ic), L is —NR$^7$CH$_2$CH$_2$—.

In some embodiments of a compound of Formula (I), Formula (Ia-1), Formula (Ia-2), Formula (Ib) or Formula (Ic), L is —S(=O)$_2$-alkylene. In some embodiments of a compound of Formula (I), Formula (Ia-1), Formula (Ia-2), Formula (Ib) or Formula (Ic), L is —S(=O)$_2$—CH$_2$CH$_2$—.

In some embodiments of a compound of Formula (I), Formula (Ia-1), Formula (Ia-2), Formula (Ib) or Formula (Ic), n is 1, 2, or 3. In some embodiments of a compound of Formula (I), Formula (Ia-1), Formula (Ia-2), Formula (Ib) or Formula (Ic), n is 1. In some embodiments of a compound of Formula (I), Formula (Ia-1), Formula (Ia-2), Formula (Ib) or Formula (Ic), n is 2. In some embodiments of a compound of Formula (I), Formula (Ia-1), Formula (Ia-2), Formula (Ib) or Formula (Ic), n is 3.

In some embodiments of a compound of Formula (I), Formula (Ia-1), Formula (Ia-2), Formula (Ib) or Formula (Ic), p is 1. In some embodiments of a compound of Formula (I), Formula (Ia-1), Formula (Ia-2), Formula (Ib) or Formula (Ic), p is 6. In some embodiments of a compound of Formula (I), Formula (Ia-1), Formula (Ia-2), Formula (Ib) or Formula (Ic), p is 7. In some embodiments of a compound of Formula (I), Formula (Ia-1), Formula (Ia-2), Formula (Ib) or Formula (Ic), p is 8. In some embodiments of a compound of Formula (I), Formula (Ia-1), Formula (Ia-2), Formula (Ib) or Formula (Ic), p is 9.

In some embodiments of a compound of Formula (I), Formula (Ia-1), Formula (Ia-2), Formula (Ib) or Formula (Ic), q is 0. In some embodiments of a compound of Formula (I), Formula (Ia-1), Formula (Ia-2), Formula (Ib) or Formula (Ic), q is 1. In some embodiments of a compound of Formula (I), Formula (Ia-1), Formula (Ia-2), Formula (Ib) or Formula (Ic), q is 2.

In some embodiments of a compound of Formula (I), Formula (Ia-1), Formula (Ia-2), Formula (Ib) or Formula (Ic), Ring A is aryl. In some embodiments of a compound of Formula (I), Formula (Ia-1), Formula (Ia-2), Formula (Ib) or Formula (Ic), Ring A is phenyl. In some embodiments of a compound of Formula (I), Formula (Ia-1), Formula (Ia-2), Formula (Ib) or Formula (Ic), Ring A is heteroaryl. In some embodiments of a compound of Formula (I), Formula (Ia-1), Formula (Ia-2), Formula (Ib) or Formula (Ic), Ring A is 6-membered heteroaryl. In some embodiments of a compound of Formula (I), Formula (Ia-1), Formula (Ia-2), Formula (Ib) or Formula (Ic), Ring A is pyridyl, pyrimidinyl, or pyrazinyl. In some embodiments of a compound of Formula (I), Formula (Ia-1), Formula (Ia-2), Formula (Ib) or Formula (Ic), Ring A is pyrimidinyl. In some embodiments of a compound of Formula (I), Formula (Ia-1), Formula (Ia-2), Formula (Ib) or Formula (Ic), Ring A is pyrazinyl. In some embodiments of a compound of Formula (I), Formula (Ia-1), Formula (Ia-2), Formula (Ib) or Formula (Ic), Ring A is a 5-membered heteroaryl. In some embodiments of a compound of Formula (I), Formula (Ia-1), Formula (Ia-2), Formula (Ib) or Formula (Ic), Ring A is thiophenyl, furanyl, pyrrolyl, thiazolyl, oxazolyl, isoxazolyl, imidazolyl, triazolyl, tetrazolyl, pyrazolyl, thiadiazolyl, or oxadiazolyl. In some embodiments of a compound of Formula (I), Formula (Ia-1), Formula (Ia-2), Formula (Ib) or Formula (Ic), Ring A is oxazolyl, pyrazolyl, pyrrolyl, or imidazolyl. In some embodiments of a compound of Formula (I), Formula (Ia-1), Formula (Ia-2), Formula (Ib) or Formula (Ic), Ring A is $C_2$-$C_8$ heterocycloalkyl. In some embodiments of a compound of Formula (I), Formula (Ia-1), Formula (Ia-2), Formula (Ib) or Formula (Ic), Ring A is tetrahydropyranyl, morpholinyl, pyrrolidinyl, piperidinyl, or piperazinyl. In some embodiments of a compound of Formula (I), Formula (Ia-1), Formula (Ia-2), Formula (Ib) or Formula (Ic), Ring A is piperidinyl. In some embodiments of a compound of Formula (I), Formula (Ia-1), Formula (Ia-2), Formula (Ib) or Formula (Ic), Ring A is $C_3$-$C_8$ cycloalkyl. In some embodiments of a compound of Formula (I), Formula (Ia-1), Formula (Ia-2), Formula (Ib) or Formula (Ic), Ring A is cyclohexyl. In some embodiments of a compound of Formula (I), Formula (Ia-1), Formula (Ia-2), Formula (Ib) or Formula (Ic), Ring A comprises at least one N atom in the ring. In some embodiments of a compound of Formula (I), Formula (Ia-1), Formula (Ia-2), Formula (Ib) or Formula (Ic), Ring A comprises at least two N atoms in the ring. In some embodiments of a compound of Formula (I), Formula (Ia-1), Formula (Ia-2), Formula (Ib) or Formula (Ic), Z is connected to Ring A through a ring nitrogen.

In some embodiments of a compound of Formula (I), Formula (Ia-1), Formula (Ia-2), Formula (Ib) or Formula (Ic), the atom chain connecting D and Z is 11, 12, 13, or 14 atoms. In some embodiments of a compound of Formula (I), Formula (Ia-1), Formula (Ia-2), Formula (Ib) or Formula (Ic), the atom chain connecting D and Z is 11 or 13 atoms. In some embodiments of a compound of Formula (I), Formula (Ia-1), Formula (Ia-2), Formula (Ib) or Formula (Ic), wherein the atom chain connecting D and Z is 11 atoms. In some embodiments of a compound of Formula (I), Formula (Ia-1), Formula (Ia-2), Formula (Ib) or Formula (Ic), the atom chain connecting D and Z is 12 atoms. In some embodiments of a compound of Formula (I), Formula (Ia-1), Formula (Ia-2), Formula (Ib) or Formula (Ic), the atom chain connecting D and Z is 13 atoms. In some embodiments of a compound of Formula (I), Formula (Ia-1), Formula (Ia-2), Formula (Ib) or Formula (Ic), the atom chain connecting D and Z is 14 atoms.

Some embodiments provided herein describe a pharmaceutical composition comprising a compound of Formula (I), Formula (Ia-1), Formula (Ia-2), Formula (Ib) or Formula (Ic), or a pharmaceutically acceptable salt, solvate, or stereoisomer thereof, and a pharmaceutically acceptable excipient. In some embodiments a pharmaceutical composition comprising a compound of Formula (I), Formula (Ia-1), Formula (Ia-2), Formula (Ib) or Formula (Ic) is formulated as a capsule. In some embodiments a pharmaceutical composition comprising a compound of Formula (I), Formula (Ia-1), Formula (Ia-2), Formula (Ib) or Formula (Ic) is formulated as a tablet. In some embodiments a pharmaceutical composition comprising a compound of Formula (I), Formula (Ia-1), Formula (Ia-2), Formula (Ib) or Formula (Ic) is formulated as an ointment. In some embodiments a pharmaceutical composition comprising a compound of Formula (I), Formula (Ia-1), Formula (Ia-2), Formula (Ib) or Formula (Ic) is formulated for intraperitoneal or intravenous injection. In some embodiments a pharmaceutical composition comprising a compound of Formula (I), Formula (Ia-1), Formula (Ia-2), Formula (Ib) or Formula (Ic) is formulated for ophthalmic administration. In some embodiments a pharmaceutical composition comprising a compound of Formula (I), Formula (Ia-1), Formula (Ia-2), Formula (Ib) or Formula (Ic), is formulated as eye drops. In some embodiments a pharmaceutical composition comprising a compound of Formula (I), Formula (Ia-1), Formula (Ia-2), Formula (Ib) or Formula (Ic), is formulated for the treatment of dry eyes. In some embodiments a pharmaceutical composition comprising a compound of Formula (I), Formula (Ia-1), Formula (Ia-2), Formula (Ib) or Formula (Ic), comprises at least one lubricant. In some embodiments a pharmaceutical composition comprising a compound of Formula (I), Formula (Ia-1), Formula (Ia-2), Formula (Ib) or Formula (Ic), comprises at least one of polyvinyl alcohol, povidone, carboxymethylcellulose sodium, glycerin, mineral oil, white petrolatum, light mineral oil, polyethylene glycol, propylene glycol, hypromellose, hydroxypropyl methylcellulose, carmellose sodium, or dextran. In some embodiments a pharmaceutical composition comprising a compound of Formula (I), Formula (Ia-1), Formula (Ia-2), Formula (Ib) or Formula (Ic) comprises at least one of polyvinyl alcohol, povidone, carboxymethylcellulose sodium, glycerin, light mineral oil, castor oil, flaxseed oil, or mineral oil. In some embodiments a pharmaceutical composition comprising a compound of Formula (I), Formula (Ia-1), Formula (Ia-2), Formula (Ib) or Formula (Ic) comprises at least one of glycerin, light mineral oil, or mineral oil. In some embodiments a pharmaceutical composition comprising a compound of Formula (I), Formula (Ia-1), Formula (Ia-2), Formula (Ib) or Formula (Ic) comprises at least one redness reducer. In some embodiments a pharmaceutical composition comprising a compound of Formula (I), Formula (Ia-1), Formula (Ia-2), Formula (Ib) or Formula (Ic) comprises at least one of naphazoline, phenylephrine, tetrahydrozoline, or a pharmaceutically acceptable salt, solvate, or stereoisomer thereof. In some embodiments a pharmaceutical composition comprising a compound of Formula (I), Formula (Ia-1), Formula (Ia-2), Formula (Ib) or Formula (Ic) comprises at least one anti-inflammatory agent. In some embodiments a pharmaceutical composition comprising a compound of Formula (I), Formula (Ia-1), Formula (Ia-2), Formula (Ib) or Formula (Ic) comprises at least one of a steroid, an immunosuppressant, or an anti-inflammatory agent. In some embodiments a pharmaceutical composition comprising a compound of Formula (I), Formula (Ia-1), Formula (Ia-2), Formula (Ib) or Formula (Ic) comprises dexamethasone. In some embodiments a pharmaceutical composition comprising a compound of Formula (I), Formula (Ia-1), Formula (Ia-2), Formula (Ib) or Formula (Ic) comprises cyclosporine A. In some embodiments a pharmaceutical composition comprising a compound of Formula (I), Formula (Ia-1), Formula (Ia-2), Formula (Ib) or Formula (Ic) comprises lifitegrast. In some embodiments a pharmaceutical composition comprising a compound of Formula (I), Formula (Ia-1), Formula (Ia-2), Formula (Ib) or Formula (Ic) comprises at least one of dexamethasone, cyclosporine A, or lifitegrast. In some embodiments a pharmaceutical composition comprising a compound of Formula (I), Formula (Ia-1), Formula (Ia-2), Formula (Ib) or Formula (Ic) comprises at least one stabilizer or preservative. In some embodiments a pharmaceutical composition comprising a compound of Formula (I), Formula (Ia-1), Formula (Ia-2), Formula (Ib) or Formula (Ic) comprises at least one of oxychloro complex, PURITE, chlorobutanol, polyquaternium-1, sodium perborate, edetate disodium, sorbic acid, benzalkonium chloride, polixetonium, Dequest, Vanish, or polyquaternium-42. In some embodiments a pharmaceutical composition comprising a compound of Formula (I), Formula (Ia-1), Formula (Ia-2), Formula (Ib) or Formula (Ic) comprises at least one of sodium perborate, benzalkonium chloride, or polyquaternium-1.

Some embodiments provided herein describe a method of treating a proliferative disease, wherein the method comprises administering a compound or pharmaceutical composition of Formula (I), Formula (Ia-1), Formula (Ia-2), Formula (Ib) or Formula (Ic), or pharmaceutically acceptable salt, solvate, or stereoisomer thereof to a subject in need thereof. In some embodiments, the proliferative disease is cancer. In some embodiments, the cancer is non-melanoma skin cancer, lung cancer, brain cancer, breast cancer, prostate cancer, colorectal cancer, bladder cancer, melanoma, non-Hodgkin lymphoma, kidney cancer, leukemia, pancreatic cancer, mesothelioma, head and neck cancer, gastric cancer, small cell lung cancer, or eye cancer. In some embodiments, the proliferative disease is metastatic cancer.

Some embodiments provided herein describe a method of inducing apoptosis in a cell, wherein the method comprises contacting the cell with a compound or pharmaceutical composition of Formula (I), Formula (Ia-1), Formula (Ia-2), Formula (Ib) or Formula (Ic), or a pharmaceutically acceptable salt, solvate, or stereoisomer thereof.

Some embodiments provided herein describe a method of inhibiting cell migration, wherein the method comprises contacting a cell with a compound or pharmaceutical composition of Formula (I), Formula (Ia-1), Formula (Ia-2), Formula (Ib) or Formula (Ic), or a pharmaceutically acceptable salt, solvate, or stereoisomer thereof.

Some embodiments provided herein describe a method of treating inflammatory or an autoimmune disease, wherein the method comprises administering a compound or pharmaceutical composition of Formula (I), Formula (Ia-1), Formula (Ia-2), Formula (Ib) or Formula (Ic), or a pharmaceutically acceptable salt, solvate, or stereoisomer thereof to a subject in need thereof. In some embodiments, the inflammatory or autoimmune disease is rheumatoid arthritis, Crohn's disease, ulcerative colitis, psoriasis, lupus erythematosus, multiple sclerosis or migraine headaches.

Some embodiments provided herein describe a method of treating a cardiovascular disease, wherein the method comprises administering a compound or pharmaceutical composition of Formula (I), Formula (Ia-1), Formula (Ia-2), Formula (Ib) or Formula (Ic), or a pharmaceutically acceptable salt, solvate, or stereoisomer thereof to a subject in need thereof. In some embodiments, the cardiovascular disease is coronary artery disease, hypertriglyceridemia, heart failure, arrhythmia, or diabetes.

Some embodiments provided herein describe a method of treating dry eye, wherein the method comprises administering a compound or pharmaceutical composition of Formula (I), Formula (Ia-1), Formula (Ia-2), Formula (Ib) or Formula (Ic), or a pharmaceutically acceptable salt, solvate, or stereoisomer thereof to a subject in need thereof. In some embodiments, the dry eye is caused by keratoconjunctivitis sicca, diabetes, rheumatoid arthritis, lupus, scleroderma, Sjogren's syndrome, aqueous tear deficiency, lipid abnormalities, lacrimal gland dysfunction, lacrimal gland inflammation, meibomian gland dysfunction, thyroid disorders or vitamin A deficiency. In some embodiments, the method comprises ophthalmic administration of a compound or pharmaceutical composition of Formula (I), Formula (Ia-1), Formula (Ia-2), Formula (Ib) or Formula (Ic), or a pharmaceutically acceptable salt, solvate, or stereoisomer thereof. In some embodiments, the method comprises ophthalmic administration to the ocular surface, or the area adjacent to the ocular surface.

Some embodiments provided herein describe an orally administered supplement formulation in unit dose form, comprising a compound of Formula (I), Formula (Ia-1), Formula (Ia-2), Formula (Ib) or Formula (Ic), wherein the compound is used to promote proper development and functioning of the brain and nervous system.

Some embodiments provided herein describe an orally administered supplement formulation in unit dose form, comprising a compound of Formula (I), Formula (Ia-1), Formula (Ia-2), Formula (Ib) or Formula (Ic), wherein the compound is used to promote the formation of healthy cell membranes.

Some embodiments provided herein describe an orally administered supplement formulation in unit dose form, comprising a compound of Formula (I), Formula (Ia-1), Formula (Ia-2), Formula (Ib) or Formula (Ic), wherein the compound is used to maintain proper thyroid, adrenal, or liver activity.

Some embodiments provided herein describe an orally administered supplement formulation in unit dose form, comprising a compound of Formula (I), Formula (Ia-1), Formula (Ia-2), Formula (Ib) or Formula (Ic), wherein the compound is used to maintain proper hormone production and hormone levels.

Some embodiments provided herein describe an orally administered supplement formulation in unit dose form, comprising a compound of Formula (I), Formula (Ia-1), Formula (Ia-2), Formula (Ib) or Formula (Ic), wherein the compound is used to help maintain a healthy blood pressure.

Some embodiments provided herein describe an orally administered supplement formulation in unit dose form, comprising a compound of Formula (I), Formula (Ia-1), Formula (Ia-2), Formula (Ib) or Formula (Ic), wherein the compound is used to promote regulation of blood clotting.

Some embodiments provided herein describe an orally administered supplement formulation in unit dose form, comprising a compound of Formula (I), Formula (Ia-1), Formula (Ia-2), Formula (Ib) or Formula (Ic), wherein the compound is used to promote regulation of healthy cholesterol levels.

Some embodiments provided herein describe an orally administered supplement formulation in unit dose form, comprising a compound of Formula (I), Formula (Ia-1), Formula (Ja-2), Formula (Ib) or Formula (Ic), wherein the compound is used to support healthy skin and hair.

In some embodiments of a formulation of Formula (I), Formula (Ia-1), Formula (Ia-2), Formula (Ib) or Formula (Ic), the formulation is formulated as a capsule. In some embodiments of a formulation of Formula (I), Formula (Ia-1), Formula (Ia-2), Formula (Ib) or Formula (Ic), the formulation is formulated as a tablet. In some embodiments of a formulation of Formula (I), Formula (Ia-1), Formula (Ia-2), Formula (Ib) or Formula (Ic), the formulation is formulated as an ointment. In some embodiments of a formulation of Formula (I), Formula (Ia-1), Formula (Ia-2), Formula (Ib) or Formula (Ic), the formulation is formulated as eye drops. In some embodiments of a formulation of Formula (I), Formula (Ia-1), Formula (Ia-2), Formula (Ib) or Formula (Ic), the formulation is a heterogeneous mixture. In some embodiments of a formulation of Formula (I), Formula (Ia-1), Formula (Ia-2), Formula (Ib) or Formula (Ic), the formulation is a homogenous mixture. In some embodiments of a formulation of Formula (I), Formula (Ia-1), Formula (Ia-2), Formula (Ib) or Formula (Ic), the formulation further comprises an excipient, wherein the excipient is selected from the group consisting of cellulose, stearic acid, silicon dioxide, magnesium stearate, titanium dioxide, natural vanillin, polyethylene glycol, riboflavin, carnauba wax, and any combination thereof. In some embodiments of a formulation of Formula (I), Formula (Ia-1), Formula (Ia-2), Formula (Ib) or Formula (Ic), the formulation is contained in a container.

Some embodiments provided herein describe a method comprising administering a formulation of Formula (I), Formula (Ia-1), Formula (Ia-2), Formula (Ib) or Formula (Ic), in unit dose form to a human. In some embodiments, the method promotes proper development and functioning of the brain and nervous system. In some embodiments, the method promotes the formation of healthy cell membranes. In some embodiments, the method supports proper thyroid, adrenal, or liver health. In some embodiments, the method maintains proper hormone production and hormone levels.

In some embodiments, the method helps maintain a healthy blood pressure. In some embodiments, the method promotes regulation of blood clotting. In some embodiments, the method supports regulation of cholesterol levels. In some embodiments, the method supports healthy skin and hair. In some embodiments, the method supports energy, vitality, or energy and vitality of the human. In some embodiments, the method is a method of supporting a healthy lifestyle, supporting well-being, or supporting a healthy lifestyle and well-being of the human.

Some embodiments provided herein describe a method of making a supplement formulation in unit dose form, comprising combining one or more compounds described herein.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)N($R^a$), —N($R^a$)C(O)$OR^a$, —OC(O)—N($R^a$)$_2$, —N($R^a$)C(O)$R^a$, —N($R^a$)S(O)$_t R^a$ (where t is 1 or 2), —S(O)$_t OR^a$ (where t is 1 or 2), —S(O)$_t R^a$ (where t is 1 or 2) and —S(O)$_t N(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)N($R^a$), —N($R^a$)C(O)$OR^a$, —OC(O)—N($R^a$)$_2$, —N($R^a$)C(O)$R^a$, —N($R^a$)S(O)$_t R^a$ (where t is 1 or 2), —S(O)$_t OR^a$ (where t is 1 or 2), —S(O)$_t R^a$ (where t is 1 or 2) and —S(O)$_t N(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$), —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)R$^a$ (where t is 1 or 2), —R$^b$—S(O)OR$^a$ (where t is 1 or 2) and —R$^b$—S(O)N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula $-R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" or "cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula $-R^c$-carbocyclyl where $R^c$ is an alkylene chain as defined above. The alkylene chain and the carbocyclyl radical are optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" or "heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)R$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a, 7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^{2}H$), tritium ($^{3}H$), iodine-125 ($^{125}I$) or carbon-14 ($^{14}C$). Isotopic substitution with $^{2}H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present invention, whether radioactive or not, are encompassed within the scope of the present invention.

In certain embodiments, the compounds disclosed herein have some or all of the $^{1}H$ atoms replaced with $^{2}H$ atoms.

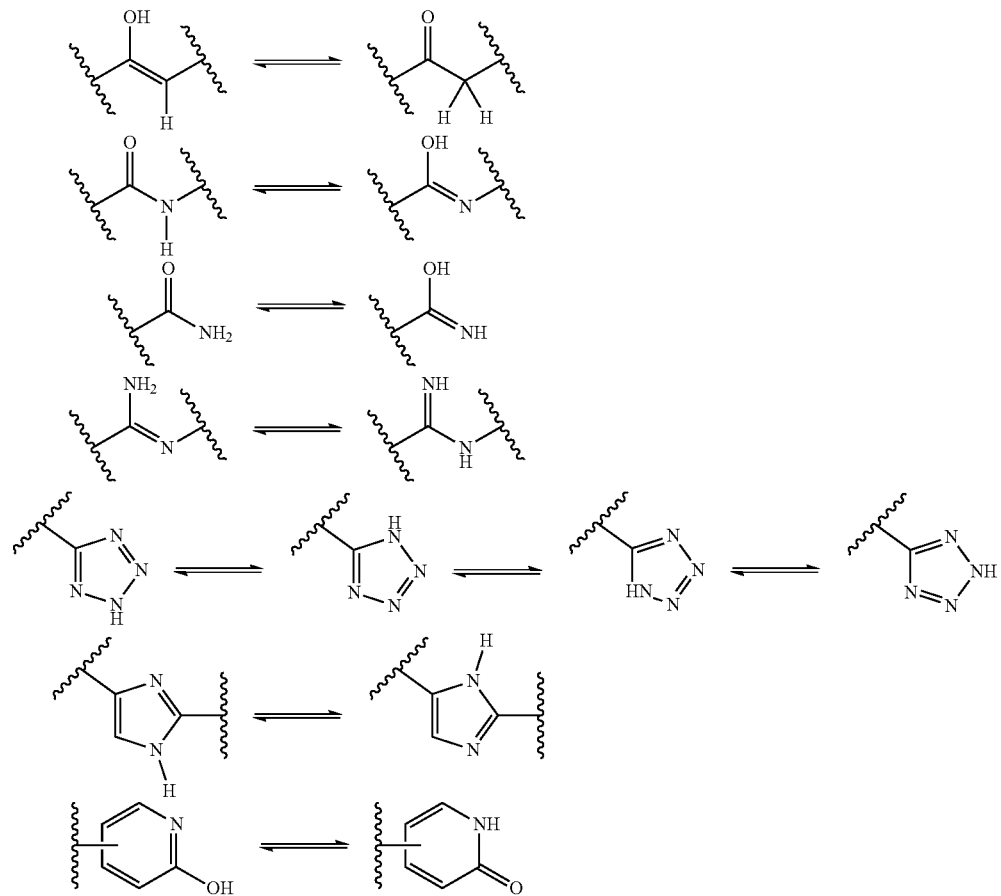

The compounds disclosed herein, in some embodiments, are used in different enriched isotopic forms, e.g., enriched in the content of $^{2}H$, $^{3}H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Compounds

Provided herein in some embodiments are compounds and pharmaceutical compositions comprising said compounds. The subject compounds and compositions are useful for the treatment of proliferative diseases, such as cancer or metastatic cancer, inflammatory disease, cardiovascular disease, autoimmune disease, and dry eye syndrome or for use as health supplements.

Some embodiments provided herein describe a compound, or a pharmaceutically acceptable salt, solvate, or stereoisomer thereof, having the structure of Formula (A):

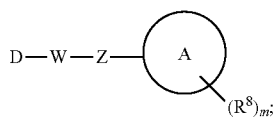

Formula (A)

wherein:
D is —CO$_2$H, —C(=O)NR$^7$R$^9$, or tetrazolyl;
W is —(CH$_2$)$_p$-(L)$_n$-(CH$_2$)$_q$—;
each L is independently —(CR$^1$R$^2$)—, —O-alkylene-, —NR$^7$-alkylene-, —S-alkylene-, —S(=O)-alkylene, —S(=O)$_2$-alkylene, or —Se-alkylene-;
Z is a bond, —NR$^3$C(=O)NR$^4$—, —NR$^3$C(=O)—, —NR$^3$C(=O)NR$^4$-alkylene-, —NR$^3$C(=O)-alkylene-NR$^4$—, —NR$^3$C(=O)-alkylene-, —NR$^3$S(=O)$_2$—, —S(=O)$_2$NR$^3$, —NR$^3$S(=O)$_2$-alkylene-, —NR$^3$S(=O)$_2$-alkylene-NR$^6$—, —S(=O)$_2$NR$^3$-alkylene-, —S(=O)$_2$—, —(C$_1$-C$_3$ heteroaryl)-, —NR$^3$C(=O)-alkylene-O—, —NR$^3$C(=O)-alkylene-S—, or —OC(=O)NR$^4$—;
Ring A is optionally substituted aryl, optionally substituted heteroaryl, optionally substituted C$_2$-C$_8$ heterocycloalkyl, or optionally substituted C$_3$-C$_8$ cycloalkyl;
each R$^1$ or R$^2$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, —NR$^c$R$^d$, or R$^1$ and R$^2$ are taken together to form a C$_1$-C$_6$ cycloalkyl or C$_1$-C$_6$ heterocycloalkyl, wherein both R$^1$ and R$^2$ on a single carbon are not hydrogen;
R$^a$ is hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;
R$^b$ is C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;
each R$^c$ and R$^d$ is independently hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;
or R$^c$ and R$^d$, together with the nitrogen atom to which they are attached, form a heterocycloalkyl or heteroaryl; wherein the heterocycloalkyl and heteroaryl is optionally substituted with one, two, or three of halogen, C$_1$-C$_6$ alkyl, C$_1$-C$_6$ haloalkyl, —OH, —OMe, or —NH$_2$;
R$^3$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;
R$^4$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;
R$^6$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;
R$^7$ and R$^9$ are independently hydrogen, —S(=O)R, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;
each R$^8$ is independently hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;
m is 1-5;
n is 0-3;
p is 0-9;
q is 0-5; and
provided that the atom chain connecting D and Z is 11, 12, 13, or 14 atoms.

Certain embodiments provided herein provide for a compound, or a pharmaceutically acceptable salt, solvate, or stereoisomer thereof, having the structure of Formula (I):

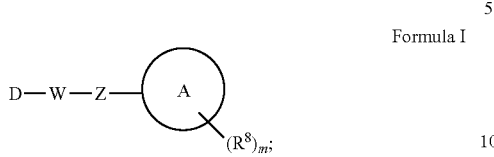

Formula I wherein:

D is —CO$_2$H, —C(=O)NR$^7$R$^9$, or tetrazolyl;

W is —(CH$_2$)$_p$-(L)$_n$-(CH$_2$)$_q$—;

each L is independently —(CR$^1$R$^2$)—, —O-alkylene-, —NR$^7$-alkylene-, —S-alkylene-, —S(=O)-alkylene-, —S(=O)$_2$-alkylene-, or —Se-alkylene-;

Z is a bond, —NR$^3$C(=O)NR$^4$—, —NR$^3$C(=O)—, —NR$^3$C(=O)NR$^4$-alkylene-, —NR$^3$C(=O)-alkylene-NR$^4$—, —NR$^3$C(=O)-alkylene-, —NR$^3$S(=O)$_2$—, —S(=O)$_2$NR$^3$, —NR$^3$S(=O)$_2$-alkylene-, —NR$^3$S(=O)$_2$-alkylene-NR$^6$—, —S(=O)$_2$NR$^3$-alkylene-, —S(=O)$_2$—, —(C$_1$-C$_3$ heteroaryl)-, —NR$^3$C(=O)-alkylene-O—, —NR$^3$C(=O)-alkylene-S—, or —OC(=O)NR$^4$—;

Ring A is optionally substituted aryl, optionally substituted heteroaryl, optionally substituted C$_2$-C$_8$ heterocycloalkyl, or optionally substituted C$_3$-C$_8$ cycloalkyl;

each R$^1$ or R$^2$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, —NR$^c$R$^d$, or R$^1$ and R$^2$ are taken together to form a C$_1$-C$_6$ cycloalkyl or C$_1$-C$_6$ heterocycloalkyl, wherein both R$^1$ and R$^2$ on a single carbon are not hydrogen;

R$^a$ is hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

R$^b$ is C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

each R$^c$ and R$^d$ is independently hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, C$_1$-C$_6$ alkyl, C$_1$-C$_6$ haloalkyl, —OH, —OMe, or —NH$_2$;

R$^3$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

R$^4$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

R$^6$ is hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

R$^7$ and R$^9$ are independently hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

each R$^8$ is independently hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

m is 1-5;
n is 0-3;
p is 0-9;
q is 0-5;
provided that the atom chain connecting D and Z is 11, 12, 13, or 14 atoms; and
provided that when A is

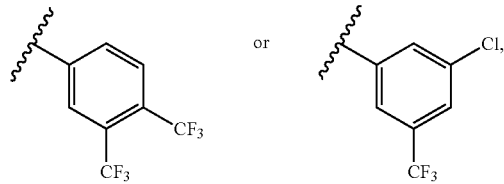 [SMILES: *c1ccc(C(F)(F)F)c(C(F)(F)F)c1 ; *c1cc(Cl)cc(C(F)(F)F)c1]

then
(iv) D is not —$CO_2H$,
(v) W is not —$(CH_2)_{12}$— or —$(CH_2)_{14}$—, or
(vi) Z is not —NHC(=O)NH—.

Certain embodiments provided herein provide for a compound, or a pharmaceutically acceptable salt, solvate, or stereoisomer thereof, having the structure of Formula (I):

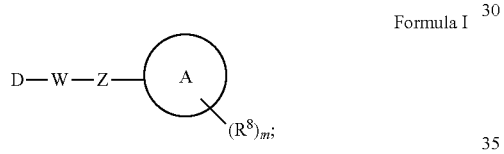

Formula I wherein:
D is —$CO_2H$, —C(=O)$NR^7R^9$, or tetrazolyl;
W is —$(CH_2)_p$-(L)$_n$-$(CH_2)_q$—;
each L is independently —($CR^1R^2$)—, —O-alkylene-, —$NR^7$-alkylene-, —S-alkylene-, —S(=O)-alkylene, —S(=O)$_2$-alkylene, or —Se-alkylene-;
Z is a bond, —$NR^3$C(=O)$NR^4$—, —$NR^3$C(=O)—, —$NR^3$C(=O)$NR^4$-alkylene-, —$NR^3$C(=O)-alkylene-$NR^4$—, —$NR^3$C(=O)-alkylene-, —$NR^3$S(=O)$_2$—, —S(=O)$_2NR^3$, —$NR^3$S(=O)$_2$-alkylene-, —$NR^3$S(=O)$_2$-alkylene-$NR^6$—, —S(=O)$_2NR^3$-alkylene-, —S(=O)$_2$—, —($C_1$-$C_3$ heteroaryl)-, —$NR^3$C(=O)-alkylene-O—, —$NR^3$C(=O)-alkylene-S—, or —OC(=O)$NR^4$—;
Ring A is optionally substituted aryl, optionally substituted heteroaryl, optionally substituted $C_2$-$C_8$ heterocycloalkyl, or optionally substituted $C_3$-$C_8$ cycloalkyl, wherein Ring A is not phenyl.
each $R^1$ or $R^2$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, —$NR^cR^d$, or $R^1$ and $R^2$ are taken together to form a $C_1$-$C_6$ cycloalkyl or $C_1$-$C_6$ heterocycloalkyl, wherein both $R^1$ and $R^2$ on a single carbon are not hydrogen;
$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;
$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;
each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;
or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$;
$R^3$ is hydrogen, —S(=O)$R^b$, —S(=O)$_2R^d$, —S(=O)$_2NR^cR^d$, —C(=O)$R^b$, —$CO_2R^a$, —C(=O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;
$R^4$ is hydrogen, —S(=O)$R^b$, —S(=O)$_2R^d$, —S(=O)$_2NR^cR^d$, —C(=O)$R^b$, —$CO_2R^a$, —C(=O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;
$R^6$ is hydrogen, —S(=O)$R^b$, —S(=O)$_2R^d$, —S(=O)$_2NR^cR^d$, —C(=O)$R^b$, —$CO_2R^a$, —C(=O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^c R^d$;

$R^7$ and $R^9$ are independently hydrogen, —$S(=O)R^b$, —$S(=O)_2 R^d$, —$S(=O)_2 NR^c R^d$, —$C(=O)R^b$, —$CO_2 R^a$, —$C(=O)NR^c R^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^c R^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^c R^d$;

each $R^8$ is independently hydrogen, —$S(=O)R^b$, —$S(=O)_2 R^d$, —$S(=O)_2 NR^c R^d$, —$C(=O)R^b$, —$CO_2 R^a$, —$C(=O)NR^c R^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^c R^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^c R^d$;

m is 1-5;
n is 0-3;
p is 0-9;
q is 0-5; and
provided that the atom chain connecting D and Z is 11, 12, 13, or 14 atoms.

In some embodiments of a compound of Formula (A) or Formula (I), the compound is of Formula (Ia-1) or Formula (Ia-2), or a pharmaceutically acceptable salt, solvate, or stereoisomer thereof:

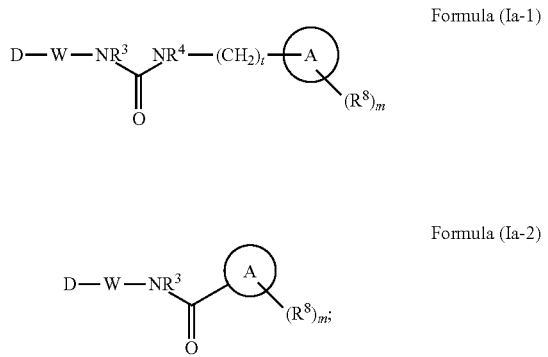

Formula (Ia-1)

Formula (Ia-2)

wherein:
D is —$CO_2 H$, —$C(=O)NR^7 R^9$, or tetrazolyl;
W is —$(CH_2)_p$-$(L)_n$-$(CH_2)_q$—;
each L is independently —$(CR^1 R^2)$—, —O-alkylene-, —$NR^7$-alkylene-, —S-alkylene-, —$S(=O)$-alkylene, —$S(=O)_2$-alkylene, or —Se-alkylene-;
Z is a bond, —$NR^3 C(=O)NR^4$—, —$NR^3 C(=O)$—, —$NR^3 C(=O)NR^4$-alkylene-, —$NR^3 C(=O)$-alkylene-$NR^4$—, —$NR^3 C(=O)$-alkylene-, —$NR^3 S(=O)_2$—, —$S(=O)_2 NR^3$, —$NR^3 S(=O)_2$-alkylene-, —$NR^3 S(=O)_2$-alkylene-$NR^6$—, —$S(=O)_2 NR^3$-alkylene-, —$S(=O)_2$—, —$(C_1$-$C_3$ heteroaryl)-, —$NR^3 C(=O)$-alkylene-O—, —$NR^3 C(=O)$-alkylene-S—, or —$OC(=O)NR^4$—;

Ring A is optionally substituted aryl, optionally substituted heteroaryl, optionally substituted $C_2$-$C_8$ heterocycloalkyl, or optionally substituted $C_3$-$C_8$ cycloalkyl, wherein Ring A is not phenyl.

each $R^1$ or $R^2$ is independently hydrogen, halogen, —CN, —$OR^a$, —$SR^a$, —$S(=O)R^b$, —$NO_2$, —$NR^c R^d$, —$S(=O)_2 R^d$, —$NR^a S(=O)_2 R^d$, —$S(=O)_2 NR^c R^d$, —$C(=O)R^b$, —$OC(=O)R^b$, —$CO_2 R^a$, —$OCO_2 R^a$, —$C(=O)NR^c R^d$, —$OC(=O)NR^c R^d$, —$NR^a C(=O)NR^c R^d$, —$NR^a C(=O)R^b$, —$NR^a C(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^c R^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, —$NR^c R^d$, or $R^1$ and $R^2$ are taken together to form a $C_1$-$C_6$ cycloalkyl or $C_1$-$C_6$ heterocycloalkyl, wherein both $R^1$ and $R^2$ on a single carbon are not hydrogen;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$;

$R^3$ is hydrogen, —$S(=O)R^b$, —$S(=O)_2 R^d$, —$S(=O)_2 NR^c R^d$, —$C(=O)R^b$, —$CO_2 R^a$, —$C(=O)NR^c R^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^c R^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^c R^d$;

$R^4$ is hydrogen, —$S(=O)R^b$, —$S(=O)_2 R^d$, —$S(=O)_2 NR^c R^d$, —$C(=O)R^b$, —$CO_2 R^a$, —$C(=O)NR^c R^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

$R^6$ is hydrogen, —$S(=O)R^b$, —$S(=O)_2R^d$, —$S(=O)_2NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

$R^7$ and $R^9$ are independently hydrogen, —$S(=O)R^b$, —$S(=O)_2R^d$, —$S(=O)_2NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^8$ is independently hydrogen, —$S(=O)R^b$, —$S(=O)_2R^d$, —$S(=O)_2NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

m is 1-5;
n is 0-3;
p is 0-9;
q is 0-5;
provided that the atom chain connecting D and Z is 11, 12, 13, or 14 atoms; and
t is 0-2.

In some embodiments of a compound of Formula (A) or Formula (I), the compound is of Formula (Ia-1) or a pharmaceutically acceptable salt, solvate, or stereoisomer thereof:

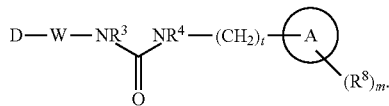

Formula (Ia-1)

In some embodiments of a compound of Formula (A) or Formula (I), the compound is of Formula (Ia-2), or a pharmaceutically acceptable salt, solvate, or stereoisomer thereof:

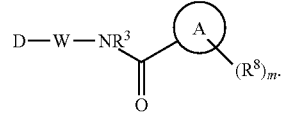

Formula (Ia-2)

In some embodiments of a compound of Formula (A) Formula (I), or Formula (Ia-2), or a pharmaceutically acceptable salt, solvate, or stereoisomer thereof has the structure:

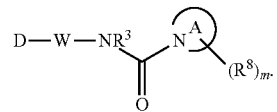

In some embodiments of a compound of Formula (A), Formula (I), Formula (Ia-1), or Formula (Ia-2), Ring A is optionally substituted aryl, optionally substituted heteroaryl, optionally substituted $C_2$-$C_8$ heterocycloalkyl, or optionally substituted $C_3$-$C_8$ cycloalkyl and D is $CO_2H$.

In some embodiments of a compound of Formula (A), Formula (I), Formula (Ia-1), or Formula (Ia-2), Ring A is optionally substituted aryl, optionally substituted heteroaryl, optionally substituted $C_2$-$C_8$ heterocycloalkyl, or optionally substituted $C_3$-$C_8$ cycloalkyl and D is tetrazolyl.

In some embodiments of a compound of Formula (A), Formula (I), Formula (Ia-1), or Formula (Ia-2), Ring A is optionally substituted aryl, optionally substituted heteroaryl, optionally substituted $C_2$-$C_8$ heterocycloalkyl, or optionally substituted $C_3$-$C_8$ cycloalkyl and D is —$C(=O)NR^7R^9$.

In some embodiments of a compound of Formula (A), Formula (I), Formula (Ia-1), or Formula (Ia-2), Ring A is N-heteroaryl and D is $CO_2H$. In some embodiments of a compound of Formula (A), Formula (I), or Formula (Ia-2), Ring A is N-heteroaryl and D is tetrazolyl. In some embodiments of a compound of Formula (A), Formula (I), or Formula (Ia-2), Ring A is N-heteroaryl and D is —$C(=O)NR^7R^9$.

In some embodiments of a compound of Formula (A), Formula (I), Formula (Ia-1), or Formula (Ia-2), Ring A is heteroaryl or $C_2$-$C_8$ heterocycloalkyl attached through a ring nitrogen.

In some embodiments of a compound of Formula (Ia-1) or Formula (Ia-2), t is 0. In some embodiments of a compound of Formula (Ia-1) or Formula (Ia-2), t is 1. In some embodiments of a compound of Formula (Ia-1) or Formula (Ia-2), t is 2.

In some embodiments of a compound of Formula (A) or Formula (I), the compound is of Formula (Ib), or a pharmaceutically acceptable salt, solvate, or stereoisomer thereof:

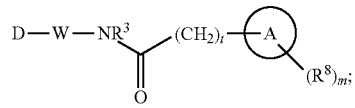

Formula (Ib)

wherein t is 0-2.

In some embodiments of a compound of Formula (A) or Formula (I), the compound is of Formula (Ic), or a pharmaceutically acceptable salt, solvate, or stereoisomer thereof:

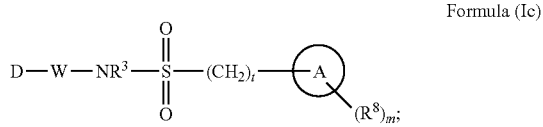

Formula (Ic)

wherein t is 0-2.

In some embodiments of a compound of Formula (Ib) or Formula (Ic), t is 0. In some embodiments of a compound of Formula (Ib) or Formula (Ic), t is 1. In some embodiments of a compound of Formula (Ib) or Formula (Ic), t is 2.

In some embodiments of a compound of Formula (A) or Formula (I), Z is a bond, $-NR^3C(=O)NR^4-$, $-NR^3C(=O)-$, $-NR^3C(=O)NR^4$-alkylene-, $-NR^3C(=O)$-alkylene-$NR^4-$, $-NR^3C(=O)$-alkylene-, $-NR^3S(=O)_2$-alkylene-, $-NR^3S(=O)_2$-alkylene-$NR^6-$, $-(C_1-C_3$ heteroaryl)-, $-NR^3C(=O)$-alkylene-O—, or $-OC(=O)NR^4-$.

In some embodiments of a compound of Formula (A) or Formula (I), Z is a bond.

In some embodiments of a compound of Formula (A) or Formula (I), Z is $-NR^3C(=O)NR^4-$.

In some embodiments of a compound of Formula (A) or Formula (I), Z is $-NR^3C(=O)NR^4$-alkylene-. In some embodiments of a compound of Formula (A) or Formula (I), Z is $-NR^3C(=O)NR^4-CH_2-$.

In some embodiments of a compound of Formula (A) or Formula (I), Z is $-NR^3C(=O)$-alkylene-$NR^4-$. In some embodiments of a compound of Formula (A) or Formula (I), Z is $-NR^3C(=O)-CH_2NR^4-$.

In some embodiments of a compound of Formula (A) or Formula (I), Z is $-(C_1-C_3$ heteroaryl)-. In some embodiments of a compound of Formula (A) or Formula (I), Z is triazolyl, tetrazolyl, furanyl, pyrrolyl, thiazolyl, oxazolyl, isoxazolyl, imidazolyl, pyrazolyl, thiadiazolyl, or oxadiazolyl. In some embodiments of a compound of Formula (A) or Formula (I), Z is triazolyl.

In some embodiments of a compound of Formula (A) or Formula (I), Z is $-NR^3C(=O)$-alkylene-O—. In some embodiments of a compound of Formula (A) or Formula (I), Z is $-NR^3C(=O)-CH_2-O-$.

In some embodiments of a compound of Formula (A) or Formula (I), Z is $-OC(=O)NR^4-$.

In some embodiments of a compound of Formula (A) or Formula (I), Z is $-NR^3S(=O)_2$-alkylene-$NR^6-$. In some embodiments of a compound of Formula (A) or Formula (I), Z is $-NR^3S(=O)_2-CH_2CH_2NR^6-$.

In some embodiments of a compound of Formula (A), Formula (I), Formula (Ia-1), Formula (Ia-2), Formula (Ib), or Formula (Ic), D is $-CO_2H$, $-C(=O)NR^7R^9$, or tetrazolyl. In some embodiments of a compound of Formula (A), Formula (I), Formula (Ia-1), Formula (Ia-2), Formula (Ib), or Formula (Ic), D is $-CO_2H$. In some embodiments of a compound of Formula (A) or Formula (I), Formula (Ia-1), Formula (Ia-2), Formula (Ib), or Formula (Ic), D is $-C(=O)NR^7R^9$. In some embodiments of a compound of Formula (A) or Formula (I), Formula (Ia-1), or Formula (Ia-2), Formula (Ib), or Formula (Ic), D is tetrazolyl.

In some embodiments of a compound of Formula (A), Formula (I), Formula (Ia-1), Formula (Ia-2), Formula (Ib), or Formula (Ic), $R^1$ and $R^2$ are independently hydrogen, $C_1-C_6$ alkyl, $C_3-C_8$ cycloalkyl, or $C_1-C_6$ haloalkyl. In some embodiments of a compound of Formula (A), Formula (I), Formula (Ia-1), Formula (Ia-2), Formula (Ib), or Formula (Ic), $R^1$ and $R^2$ are independently hydrogen. In some embodiments of a compound of Formula (A), Formula (I), Formula (Ia-1), Formula (Ia-2), Formula (Ib), or Formula (Ic), $R^1$ and $R^2$ are hydrogen.

In some embodiments of a compound of Formula (A), Formula (I), Formula (Ia-1), Formula (Ia-2), Formula (Ib), or Formula (Ic), $R^3$ and $R^4$ are independently hydrogen, $C_1-C_6$ alkyl, $C_3-C_8$ cycloalkyl, or $C_1-C_6$ haloalkyl. In some embodiments of a compound of Formula (A), Formula (I), Formula (Ia-1), Formula (Ia-2), Formula (Ib), or Formula (Ic), $R^3$ and $R^4$ are independently hydrogen. In some embodiments of a compound of Formula (A), Formula (I), Formula (Ia-1), Formula (Ia-2), Formula (Ib), or Formula (Ic), $R^3$ and $R^4$ are H. In some embodiments of a compound of Formula (A), Formula (I), Formula (Ia-1), Formula (Ia-2), Formula (Ib), or Formula (Ic), $R^3$ is H.

In some embodiments of a compound of Formula (A), Formula (I), Formula (Ia-1), Formula (Ia-2), Formula (Ib), or Formula (Ic), $R^6$ is hydrogen, $C_1-C_6$ alkyl, $C_3-C_8$ cycloalkyl, or $C_1-C_6$ haloalkyl. In some embodiments of a compound of Formula (A), Formula (I), Formula (Ia-1), Formula (Ia-2), Formula (Ib), or Formula (Ic), $R^6$ is hydrogen or $C_1-C_6$ alkyl. In some embodiments of a compound of Formula (A), Formula (I), Formula (Ia-1), Formula (Ia-2), Formula (Ib), or Formula (Ic), $R^6$ is methyl.

In some embodiments of a compound of Formula (A), Formula (I), Formula (Ia-1), Formula (Ia-2), Formula (Ib), or Formula (Ic), $R^7$ and $R^9$ are independently hydrogen, $C_1-C_6$ alkyl, $C_3-C_8$ cycloalkyl, or $C_1-C_6$ haloalkyl. In some embodiments of a compound of Formula (A), Formula (I), Formula (Ia-1), Formula (Ia-2), Formula (Ib), or Formula (Ic), $R^7$ and $R^9$ are independently hydrogen, or $C_1-C_6$ alkyl. In some embodiments of a compound of Formula (A), Formula (I), Formula (Ia-1), Formula (Ia-2), Formula (Ib), or Formula (Ic), $R^7$ and $R^9$ are independently hydrogen. In some embodiments of a compound of Formula (A), Formula (I), Formula (Ia-1), Formula (Ia-2), Formula (Ib), or Formula (Ic), $R^7$ is H. In some embodiments of a compound of Formula (A), Formula (I), Formula (Ia-1), Formula (Ia-2), Formula (Ib), or Formula (Ic), $R^7$ is H or $CH_3$. In some embodiments of a compound of Formula (A), Formula (I), Formula (Ia-1), Formula (Ia-2), Formula (Ib), or Formula (Ic), $R^7$ and $R^9$ are H.

In some embodiments of a compound of Formula (A), Formula (I), Formula (Ia-1), Formula (Ia-2), Formula (Ib), or Formula (Ic), each $R^8$ is hydrogen, halogen, $C_1-C_6$ alkyl, $C_3-C_8$ cycloalkyl, or $C_1-C_6$ haloalkyl. In some embodiments of a compound of Formula (A), Formula (I), Formula (Ia-1), Formula (Ia-2), Formula (Ib), or Formula (Ic), each $R^8$ is hydrogen. In some embodiments of a compound of Formula (A), Formula (I), Formula (Ia-1), Formula (Ia-2), Formula (Ib), or Formula (Ic), each $R^8$ is fluorine. In some embodiments of a compound of Formula (A), Formula (I), Formula (Ia-1), Formula (Ia-2), Formula (Ib), or Formula (Ic), each $R^8$ is hydrogen. In some embodiments of a compound of Formula (A), Formula (I), Formula (Ia-1), Formula (Ia-2), Formula (Ib), or Formula (Ic), each $R^8$ is $C_1-C_6$ haloalkyl. In some embodiments of a compound of Formula (A), Formula (I), Formula (Ia-1), Formula (Ia-2), Formula (Ib), or Formula (Ic), each $R^8$ is trifluoroalkyl. In some embodiments of a compound of Formula (A), Formula (I), Formula (Ia-1), Formula (Ia-2), Formula (Ib), or Formula (Ic), each $R^8$ is trifluoromethyl. In some embodiments of a compound of Formula (A), Formula (I), Formula (Ia-1), Formula (Ia-2), Formula (Ib), or Formula (Ic), each $R^8$ is $-C(=O)(C_1-C_6$ alkyl). In some embodiments of a compound of Formula (A), Formula (I), Formula (Ia-1), Formula (Ia-2), Formula (Ib), or Formula (Ic), each $R^8$ is $-C(=O)CH_3$. In some embodiments of a compound of Formula (A), Formula (I), Formula (Ia-1), Formula (Ia-2), Formula (Ib), or Formula (Ic), each $R^8$ is $C_1$-$C_6$ alkyl. In some embodiments of a compound of Formula (A), Formula (I), Formula (Ia-1), Formula (Ia-2), Formula (Ib), or Formula (Ic), each $R^8$ is $CH_3$. In some embodiments of a compound of Formula (A), Formula (I), Formula (Ia-1), Formula (Ia-2), Formula (Ib), or Formula (Ic), each $R^8$ is OH. In some embodiments of a compound of Formula (A), Formula (I), Formula (Ia-1), Formula (Ia-2), Formula (Ib), or Formula (Ic), each $R^8$ is OH or $CF_3$. In some embodiments of a compound of Formula (A), Formula (I), Formula (Ia-1), Formula (Ia-2), Formula (Ib), or Formula (Ic), each $R^8$ is Cl. In some embodiments of a compound of Formula (A), Formula (I), Formula (Ia-1), Formula (Ia-2), Formula (Ib), or Formula (Ic), each $R^8$ is Cl or $CF_3$. In some embodiments of a compound of Formula (A), Formula (I), Formula (Ia-1), Formula (Ia-2), Formula (Ib), or Formula (Ic), each $R^8$ is F or $CF_3$.

In some embodiments of a compound of Formula (A), Formula (I), Formula (Ia-1), Formula (Ia-2), Formula (Ib), or Formula (Ic), m is 1-5. In some embodiments of a compound of Formula (A), Formula (I), Formula (Ia-1), Formula (Ia-2), Formula (Ib), or Formula (Ic), m is 1. In some embodiments of a compound of Formula (A), Formula (I), Formula (Ia-1), Formula (Ia-2), Formula (Ib), or Formula (Ic), m is 2. In some embodiments of a compound of Formula (A), Formula (I), Formula (Ia-1), Formula (Ia-2), Formula (Ib), or Formula (Ic), m is 3. In some embodiments of a compound of Formula (A), Formula (I), Formula (Ia-1), Formula (Ia-2), Formula (Ib), or Formula (Ic), m is 4. In some embodiments of a compound of Formula (A), Formula (I), Formula (Ia-1), Formula (Ia-2), Formula (Ib), or Formula (Ic), m is 5. In some embodiments of a compound of Formula (A), Formula (I), Formula (Ia-1), Formula (Ia-2), Formula (Ib), or Formula (Ic), m is 2-5.

In some embodiments of a compound of Formula (A), Formula (I), Formula (Ia-1), Formula (Ia-2), Formula (Ib), or Formula (Ic), W is —$(CH_2)_p$-$(L)_n$-$(CH_2)_q$—, and each L is independently —$(CR^1R^2)$—, —O-alkylene-, —$NR^7$-alkylene-, —S-alkylene-, —S(=O)-alkylene-, —$S(=O)_2$-alkylene, or —Se-alkylene-. In some embodiments of a compound of Formula (A), Formula (I), Formula (Ia-1), Formula (Ia-2), Formula (Ib), or Formula (Ic), L is —S-alkylene-. In some embodiments of a compound of Formula (A), Formula (I), Formula (Ia-1), Formula (Ia-2), Formula (Ib), or Formula (Ic), L is —$OCH_2CH_2$—. In some embodiments of a compound of Formula (A), Formula (I), Formula (Ia-1), Formula (Ia-2), Formula (Ib), or Formula (Ic), L is —$SCH_2CH_2$—. In some embodiments of a compound of Formula (A), Formula (I), Formula (Ia-1), Formula (Ia-2), Formula (Ib), or Formula (Ic), L is —$NR^7CH_2CH_2$—. In some embodiments of a compound of Formula (A), Formula (I), Formula (Ia-1), Formula (Ia-2), Formula (Ib), or Formula (Ic), L is —$S(=O)_2$-alkylene. In some embodiments of a compound of Formula (A), Formula (I), Formula (Ia-1), Formula (Ia-2), Formula (Ib), or Formula (Ic), L is —$S(=O)_2$—$CH_2CH_2$—.

In some embodiments of a compound of Formula (A), Formula (I), Formula (Ia-1), Formula (Ia-2), Formula (Ib), or Formula (Ic), W is —$(CH_2)_{14}$—. In some embodiments of a compound of Formula (A), Formula (I), Formula (Ia-1), Formula (Ia-2), Formula (Ib), or Formula (Ic), W is —$(CH_2)_{13}$—. In some embodiments of a compound of Formula (A), Formula (I), Formula (Ia-1), Formula (Ia-2), Formula (Ib), or Formula (Ic), W is —$(CH_2)_{12}$—. In some embodiments of a compound of Formula (A), Formula (I), Formula (Ia-1), Formula (Ia-2), Formula (Ib), or Formula (Ic), W is —$(CH_2)_{11}$—.

In some embodiments of a compound of Formula (A), Formula (I), Formula (Ia-1), Formula (Ia-2), Formula (Ib), or Formula (Ic), W is

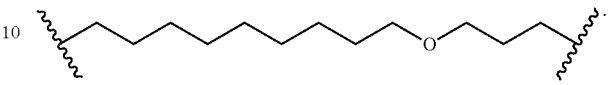

In some embodiments of a compound of Formula (A), Formula (I), Formula (Ia-1), Formula (Ia-2), Formula (Ib), or Formula (Ic), W is

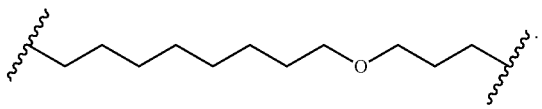 [SMILES: *CCCCCCCCOCCC*]

In some embodiments of a compound of Formula (A), Formula (I), Formula (Ia-1), Formula (Ia-2), Formula (Ib), or Formula (Ic), W is

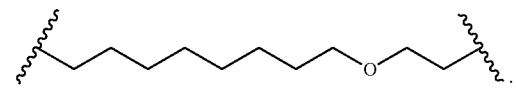 [SMILES: *CCCCCCCCOCC*]

In some embodiments of a compound of Formula (A), Formula (I), Formula (Ia-1), Formula (Ia-2), Formula (Ib), or Formula (Ic), W is

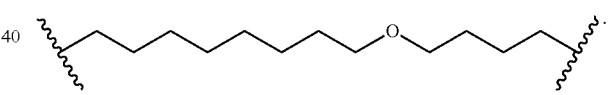

In some embodiments of a compound of Formula (A), Formula (I), Formula (Ia-1), Formula (Ia-2), Formula (Ib), or Formula (Ic), W is

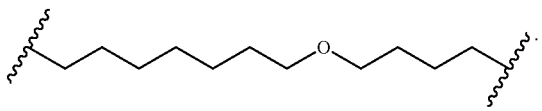 [SMILES: *CCCCCCCOCCCC*]

In some embodiments of a compound of Formula (A), Formula (I), Formula (Ia-1), Formula (Ia-2), Formula (Ib), or Formula (Ic), W is

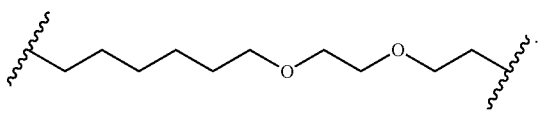 [SMILES: *CCCCCCOCCOCC*]

In some embodiments of a compound of Formula (A), Formula (I), Formula (Ia-1), Formula (Ia-2), Formula (Ib), or Formula (Ic), W is

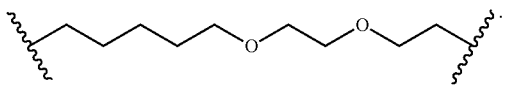 [SMILES: *CCCCCOCCOCC*]

In some embodiments of a compound of Formula (A), Formula (I), Formula (Ia-1), Formula (Ia-2), Formula (Ib), or Formula (Ic), W is

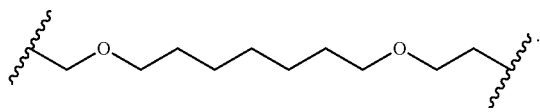 [SMILES: *CCOCCCCCCCOC*]

In some embodiments of a compound of Formula (A), Formula (I), Formula (Ia-1), Formula (Ia-2), Formula (Ib), or Formula (Ic), W is

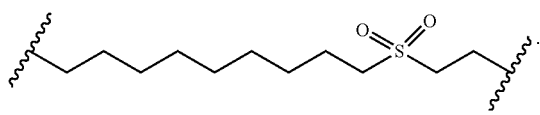 [SMILES: *CCCCCCCCCS(=O)(=O)CC*]

In some embodiments of a compound of Formula (A), Formula (I), Formula (Ia-1), Formula (Ia-2), Formula (Ib), or Formula (Ic), W is

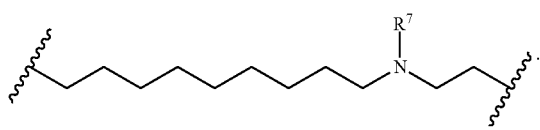

In some embodiments of a compound of Formula (A), Formula (I), Formula (Ia-1), Formula (Ia-2), Formula (Ib), or Formula (Ic), W is

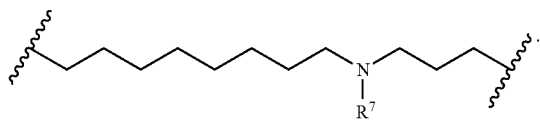

In some embodiments of a compound of Formula (A), Formula (I), Formula (Ia-1), Formula (Ia-2), Formula (Ib), or Formula (Ic), n is 1, 2, or 3. In some embodiments of a compound of Formula (A), Formula (I), Formula (Ia-1), Formula (Ia-2), Formula (Ib), or Formula (Ic), n is 1 or 2. In some embodiments of a compound of Formula (A), Formula (I), Formula (Ia-1), Formula (Ia-2), Formula (Ib), or Formula (Ic), n is 1, or 3. In some embodiments of a compound of Formula (A), Formula (I), Formula (Ia-1), Formula (Ia-2), Formula (Ib), or Formula (Ic), n is 2, or 3. In some embodiments of a compound of Formula (A), Formula (I), Formula (Ia-1), Formula (Ia-2), Formula (Ib), or Formula (Ic), n is 1. In some embodiments of a compound of Formula (A), Formula (I), Formula (Ia-1), Formula (Ia-2), Formula (Ib), or Formula (Ic), n is 2. In some embodiments of a compound of Formula (A), Formula (I), Formula (Ia-1), Formula (Ia-2), Formula (Ib), or Formula (Ic), n is 3.

In some embodiments of a compound of Formula (A), Formula (I), Formula (Ia-1), Formula (Ia-2), Formula (Ib), or Formula (Ic), p is 0-9. In some embodiments of a compound of Formula (A), Formula (I), Formula (Ia-1), Formula (Ia-2), Formula (Ib), or Formula (Ic), p is 1-6. In some embodiments of a compound of Formula (A), Formula (I), Formula (Ia-1), Formula (Ia-2), Formula (Ib), or Formula (Ic), p is 0-4. In some embodiments of a compound of Formula (A), Formula (I), Formula (Ia-1), Formula (Ia-2), Formula (Ib), or Formula (Ic), p is 3-7. In some embodiments of a compound of Formula (A), Formula (I), Formula (Ia-1), Formula (Ia-2), Formula (Ib), or Formula (Ic), p is 5-9. In some embodiments of a compound of Formula (A), Formula (I), Formula (Ia-1), Formula (Ia-2), Formula (Ib), or Formula (Ic), p is 6-9. In some embodiments of a compound of Formula (A), Formula (I), Formula (Ia-1), Formula (Ia-2), Formula (Ib), or Formula (Ic), p is 0. In some embodiments of a compound of Formula (A), Formula (I), Formula (Ia-1), Formula (Ia-2), Formula (Ib), or Formula (Ic), p is 1. In some embodiments of a compound of Formula (A), Formula (I), Formula (Ia-1), Formula (Ia-2), Formula (Ib), or Formula (Ic), p is 2. In some embodiments of a compound of Formula (A), Formula (I), Formula (Ia-1), Formula (Ia-2), Formula (Ib), or Formula (Ic), p is 3. In some embodiments of a compound of Formula (A), Formula (I), Formula (Ia-1), Formula (Ia-2), Formula (Ib), or Formula (Ic), p is 4. In some embodiments of a compound of Formula (A), Formula (I), Formula (Ia-1), Formula (Ia-2), Formula (Ib), or Formula (Ic), p is 5. In some embodiments of a compound of Formula (A), Formula (I), Formula (Ia-1), Formula (Ia-2), Formula (Ib), or Formula (Ic), p is 6. In some embodiments of a compound of Formula (A), Formula (I), Formula (Ia-1), Formula (Ia-2), Formula (Ib), or Formula (Ic), p is 7. In some embodiments of a compound of Formula (A), Formula (I), Formula (Ia-1), Formula (Ia-2), Formula (Ib), or Formula (Ic), p is 8. In some embodiments of a compound of Formula (A), Formula (I), Formula (Ia-1), Formula (Ia-2), Formula (Ib), or Formula (Ic), p is 9.

In some embodiments of a compound of Formula (A), Formula (I), Formula (Ia-1), Formula (Ia-2), Formula (Ib), or Formula (Ic), q is 0-5. In some embodiments of a compound of Formula (A), Formula (I), Formula (Ia-1), Formula (Ia-2), Formula (Ib), or Formula (Ic), q is 0-3. In some embodiments of a compound of Formula (A), Formula (I), Formula (Ia-1), Formula (Ia-2), Formula (Ib), or Formula (Ic), q is 2-5. In some embodiments of a compound of Formula (A), Formula (I), Formula (Ia-1), Formula (Ia-2), Formula (Ib), or Formula (Ic), q is 0. In some embodiments of a compound of Formula (A), Formula (I), Formula (Ia-1), Formula (Ia-2), Formula (Ib), or Formula (Ic), q is 1. In some embodiments of a compound of Formula (A), Formula (I), Formula (Ia-1), Formula (Ia-2), Formula (Ib), or Formula (Ic), q is 2. In some embodiments of a compound of Formula (A), Formula (I), Formula (Ia-1), Formula (Ia-2), Formula (Ib), or Formula (Ic), q is 3. In some embodiments of a compound of Formula (A), Formula (I), Formula (Ia-1), Formula (Ia-2), Formula (Ib), or Formula (Ic), q is 4. In some embodiments of a compound of Formula (A), Formula (I), Formula (Ia-1), Formula (Ia-2), Formula (Ib), or Formula (Ic), q is 5.

In some embodiments of a compound of Formula (A), Formula (I), Formula (Ia-1), Formula (Ia-2), Formula (Ib), or Formula (Ic), q is 9 and p is 5. In some embodiments of a compound of Formula (A), Formula (I), Formula (Ia-1), Formula (Ia-2), Formula (Ib), or Formula (Ic), q is 9 and p is 4. In some embodiments of a compound of Formula (A), Formula (I), Formula (Ia-1), Formula (Ia-2), Formula (Ib), or Formula (Ic), q is 9 and p is 3. In some embodiments of a compound of Formula (A), Formula (I), Formula (Ia-1), Formula (Ia-2), Formula (Ib), or Formula (Ic), q is 9 and p is 2. In some embodiments of a compound of Formula (A), Formula (I), Formula (Ia-1), Formula (Ia-2), Formula (Ib), or Formula (Ic), p is 0-5 and q is 0-4. In some embodiments of a compound of Formula (A), Formula (I), Formula (Ia-1), Formula (Ia-2), Formula (Ib), or Formula (Ic), p is 3-6 and q is 2-4. In some embodiments of a compound of Formula (A), Formula (I), Formula (Ia-1), Formula (Ia-2), Formula (Ib), or Formula (Ic), p is 0-9 and q is 1. In some embodiments of a compound of Formula (A), Formula (I), Formula (Ia-1), Formula (Ia-2), Formula (Ib), or Formula (Ic), p is 0-9 and q is 2.

In some embodiments of a compound of Formula (A), Formula (I), Formula (Ia-1), Formula (Ia-2), Formula (Ib), or Formula (Ic), Ring A is aryl. In some embodiments of a compound of Formula (A), Formula (I), Formula (Ia-1), Formula (Ia-2), Formula (Ib), or Formula (Ic), Ring A is phenyl.

In some embodiments of a compound of Formula (A), Formula (I), Formula (Ia-1), Formula (Ia-2), Formula (Ib), or Formula (Ic), Ring A is heteroaryl.

In some embodiments of a compound of Formula (A), Formula (I), Formula (Ia-1), Formula (Ia-2), Formula (Ib), or Formula (Ic), Ring A is 6-membered heteroaryl. In some embodiments of a compound of Formula (A), Formula (I), Formula (Ia-1), Formula (Ia-2), Formula (Ib), or Formula (Ic), Ring A is pyridyl, pyrimidinyl, or pyrazinyl. In some embodiments of a compound of Formula (A), Formula (I), Formula (Ia-1), Formula (Ia-2), Formula (Ib), or Formula (Ic), Ring A is pyrimidinyl. In some embodiments of a compound of Formula (A), Formula (I), Formula (Ia-1), Formula (Ia-2), Formula (Ib), or Formula (Ic), Ring A is pyrazinyl.

In some embodiments of a compound of Formula (A), Formula (I), Formula (Ia-1), Formula (Ia-2), Formula (Ib), or Formula (Ic), Ring A is 5-membered heteroaryl. In some embodiments of a compound of Formula (A), Formula (I), Formula (Ia-1), Formula (Ia-2), Formula (Ib), or Formula (Ic), Ring A is thiophenyl, furanyl, pyrrolyl, thiazolyl, oxazolyl, isoxazolyl, imidazolyl, triazolyl, tetrazolyl, pyrazolyl, thiadiazolyl, or oxadiazolyl. In some embodiments of a compound of Formula (A), Formula (I), Formula (Ia-1), Formula (Ia-2), Formula (Ib), or Formula (Ic), Ring A is oxazolyl, pyrazolyl, pyrrolyl, or imidazolyl.

In some embodiments of a compound of Formula (A), Formula (I), Formula (Ia-1), Formula (Ia-2), Formula (Ib), or Formula (Ic), Ring A is $C_2$-$C_8$ heterocycloalkyl. In some embodiments of a compound of Formula (A), Formula (I), Formula (Ia-1), Formula (Ia-2), Formula (Ib), or Formula (Ic), Ring A is tetrahydropyranyl, morpholinyl, pyrrolidinyl, piperidinyl, or piperazinyl. In some embodiments of a compound of Formula (A), Formula (I), Formula (Ia-1), Formula (Ia-2), Formula (Ib), or Formula (Ic), Ring A is piperidinyl.

In some embodiments of a compound of Formula (A), Formula (I), Formula (Ia-1), Formula (Ia-2), Formula (Ib), or Formula (Ic), Ring A is $C_3$-$C_8$ cycloalkyl. In some embodiments of a compound of Formula (A), Formula (I), Formula (Ia-1), Formula (Ia-2), Formula (Ib), or Formula (Ic), Ring A is Ring A is cyclohexyl.

In some embodiments of a compound of Formula (A), Formula (I), Formula (Ia-1), Formula (Ia-2), Formula (Ib), or Formula (Ic), Ring A is heteroaryl or $C_2$-$C_8$ heterocycloalkyl. In some embodiments of a compound of Formula (A), Formula (I), Formula (Ia-1), Formula (Ia-2), Formula (Ib), or Formula (Ic), Ring comprises at least one N atom in the ring. In some embodiments of a compound of Formula (A), Formula (I), Formula (Ia-1), Formula (Ia-2), Formula (Ib), or Formula (Ic), Ring A comprises at least two N atoms in the ring. In some embodiments of a compound of Formula (A), Formula (I), Formula (Ia-1), Formula (Ia-2), Formula (Ib), or Formula (Ic), Ring comprises at least one O atom in the ring. In some embodiments of a compound of Formula (A), Formula (I), Formula (Ia-1), Formula (Ia-2), Formula (Ib), or Formula (Ic), Ring comprises at least one S atom in the ring. In some embodiments of a compound of Formula (A), Formula (I), Formula (Ia-1), Formula (Ia-2), Formula (Ib), or Formula (Ic), Ring A is heteroaryl or $C_2$-$C_8$ heterocycloalkyl and Z is connected to Ring A through a ring nitrogen.

In some embodiments of a compound of Formula (A), Formula (I), Formula (Ia-1), Formula (Ia-2), Formula (Ib), or Formula (Ic), the atom chain connecting D and Z is 11, 12, 13, or 14 atoms. In some embodiments of a compound of Formula (A), Formula (I), Formula (Ia-1), Formula (Ia-2), Formula (Ib), or Formula (Ic), the atom chain connecting D and Z is 11 or 14 atoms. In some embodiments of a compound of Formula (A), Formula (I), Formula (Ia-1), Formula (Ia-2), Formula (Ib), or Formula (Ic), the atom chain connecting D and Z is 12 or 14 atoms. In some embodiments of a compound of Formula (A), Formula (I), Formula (Ia-1), Formula (Ia-2), Formula (Ib), or Formula (Ic), the atom chain connecting D and Z is 11 atoms. In some embodiments of a compound of Formula (A), Formula (I), Formula (Ia-1), Formula (Ia-2), Formula (Ib), or Formula (Ic), the atom chain connecting D and Z is 12 atoms. In some embodiments of a compound of Formula (A), Formula (I), Formula (Ia-1), Formula (a-2), Formula (Ib), or Formula (Ic), the atom chain connecting D and Z is 13 atoms. In some embodiments of a compound of Formula (A), Formula (I), Formula (Ia-1), Formula (a-2), Formula (Ib), or Formula (Ic), the atom chain connecting D and Z is 14 atoms.

In some embodiments, the compounds disclosed herein are provided in Table 1.

TABLE 1

| # | Structure | Name |
|---|-----------|------|
| 1 | 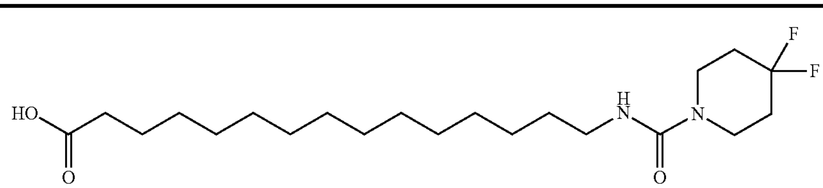 | 15-(4,4-difluoropiperidine-1-carboxamido)pentadecanoic acid |

TABLE 1-continued

| # | Structure | Name |
|---|---|---|
| 2 | 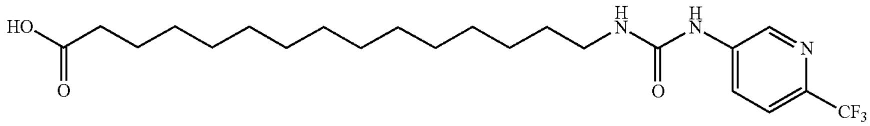 [SMILES: O=C(O)CCCCCCCCCCCCCCNC(=O)Nc1ccc(C(F)(F)F)nc1] | 15-(3-(6-(trifluoromethyl)pyridin-3-yl)ureido)pentadecanoic acid |
| 3 | 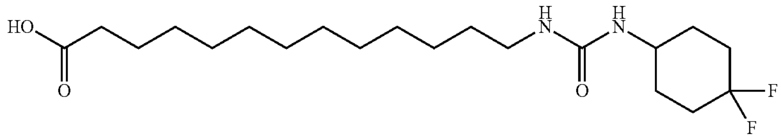 [SMILES: O=C(O)CCCCCCCCCCCCNC(=O)NC1CCC(F)(F)CC1] | 13-(3-(4,4-difluorocyclohexyl)ureido)tridecanoic acid |
| 4 | 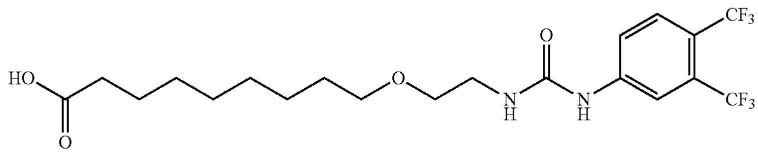 [SMILES: O=C(O)CCCCCCCCOCCNC(=O)Nc1ccc(C(F)(F)F)c(C(F)(F)F)c1] | 9-(2-(3-(3,4-bis(trifluoromethyl)phenyl)ureido)ethoxy)nonanoic acid |
| 5 | 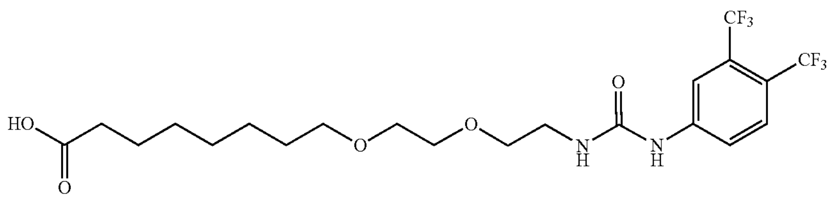 [SMILES: O=C(O)CCCCCCCOCCOCCNC(=O)Nc1ccc(C(F)(F)F)c(C(F)(F)F)c1] | 8-(2-(2-(3-(3,4-bis(trifluoromethyl)phenyl)ureido)ethoxy)ethoxy)octanoic acid |
| 6 | 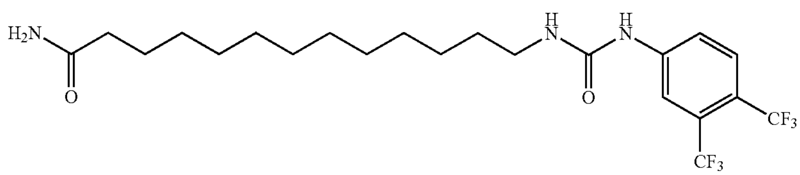 [SMILES: NC(=O)CCCCCCCCCCCCNC(=O)Nc1ccc(C(F)(F)F)c(C(F)(F)F)c1] | 13-(3-(3,4-bis(trifluoromethyl)phenyl)ureido)tridecanamide |
| 7 | 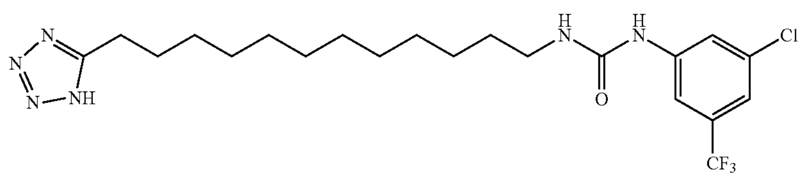 [SMILES: O=C(NCCCCCCCCCCCCc1nnn[nH]1)Nc1cc(Cl)cc(C(F)(F)F)c1] | 1-(12-(1H-tetrazol-5-yl)dodecyl)-3-(3-chloro-5-(trifluoromethyl)phenyl)urea |
| 8 | 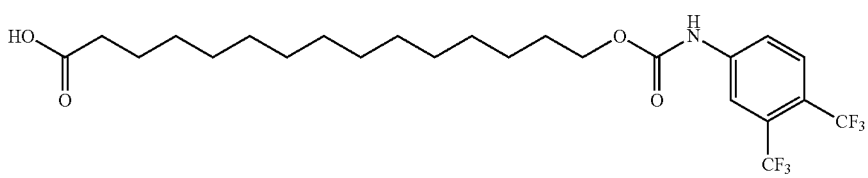 [SMILES: O=C(O)CCCCCCCCCCCCCCOC(=O)Nc1ccc(C(F)(F)F)c(C(F)(F)F)c1] | 15-(((3,4-bis(trifluoromethyl)phenyl)carbamoyl)oxy)pentadecanoic acid |
| 9 | 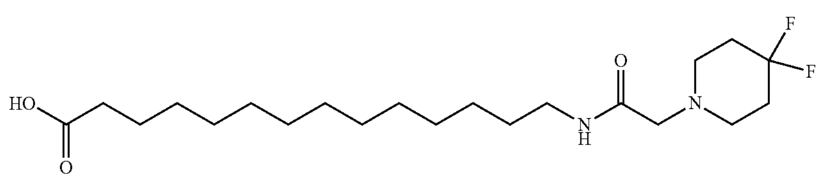 [SMILES: O=C(O)CCCCCCCCCCCCCNC(=O)CN1CCC(F)(F)CC1] | 14-(2-(4,4-difluoropiperidin-1-yl)acetamido)tetradecanoic acid |
| 10 | 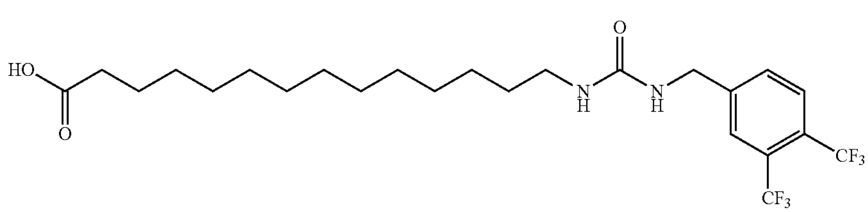 [SMILES: O=C(O)CCCCCCCCCCCCCNC(=O)NCc1ccc(C(F)(F)F)c(C(F)(F)F)c1] | 14-(3-(3,4-bis(trifluoromethyl)benzyl)ureido)tetradecanoic acid |

TABLE 1-continued

| # | Structure | Name |
|---|---|---|
| 11 | 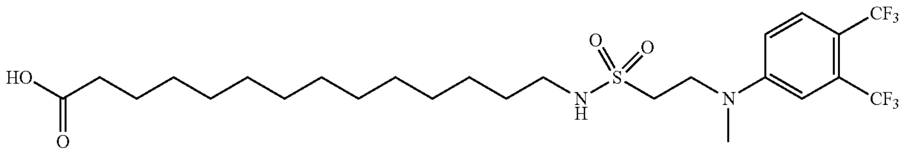 [SMILES: CN(CCS(=O)(=O)NCCCCCCCCCCCCCC(=O)O)c1ccc(C(F)(F)F)c(C(F)(F)F)c1] | 14-((2-((3,4-bis(trifluoromethyl)phenyl)(methyl)amino)ethyl)sulfonamido)tetradecanoic acid |
| 12 | 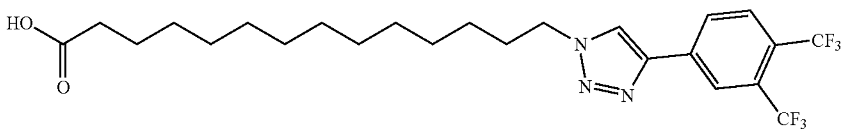 [SMILES: O=C(O)CCCCCCCCCCCCCn1cc(-c2ccc(C(F)(F)F)c(C(F)(F)F)c2)nn1] | 14-(4-(3,4-bis(trifluoromethyl)phenyl)-1H-1,2,3-triazol-1-yl)tetradecanoic acid |
| 13 | 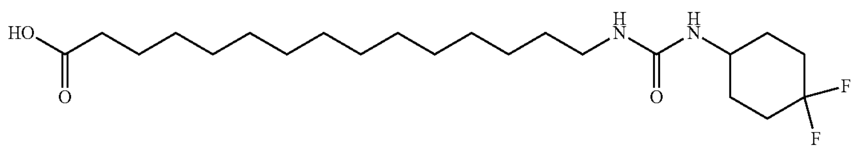 [SMILES: O=C(O)CCCCCCCCCCCCCCNC(=O)NC1CCC(F)(F)CC1] | 15-(3-(4,4-difluorocyclohexyl)ureido)pentadecanoic acid |
| 14 | 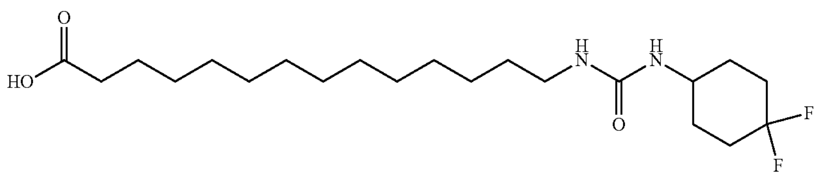 [SMILES: O=C(O)CCCCCCCCCCCCCNC(=O)NC1CCC(F)(F)CC1] | 14-(3-(4,4-difluorocyclohexyl)ureido)tetradecanoic acid |
| 15 | 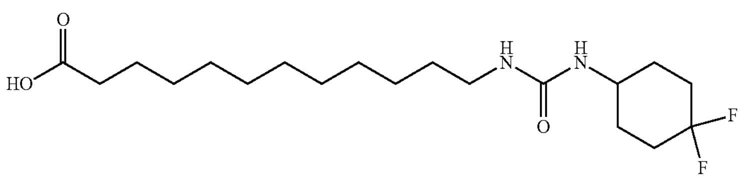 [SMILES: O=C(O)CCCCCCCCCCCNC(=O)NC1CCC(F)(F)CC1] | 12-(3-(4,4-difluorocyclohexyl)ureido)dodecanoic acid |
| 16 | 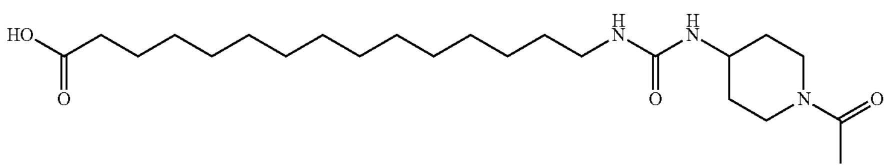 [SMILES: CC(=O)N1CCC(NC(=O)NCCCCCCCCCCCCCCC(=O)O)CC1] | 15-(3-(1-acetylpiperidin-4-yl)ureido)pentadecanoic acid |
| 17 | 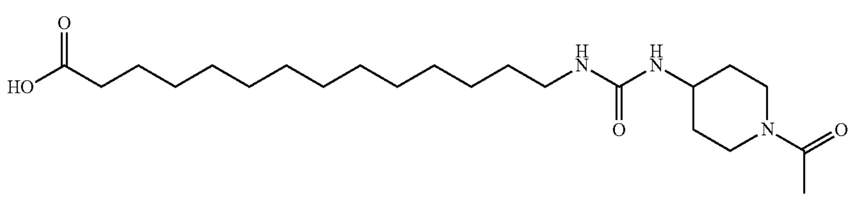 [SMILES: CC(=O)N1CCC(NC(=O)NCCCCCCCCCCCCCC(=O)O)CC1] | 14-(3-(1-acetylpiperidin-4-yl)ureido)tetradecanoic acid |
| 18 | 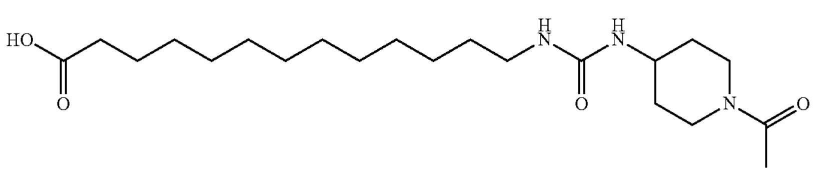 [SMILES: CC(=O)N1CCC(NC(=O)NCCCCCCCCCCCCC(=O)O)CC1] | 13-(3-(1-acetylpiperidin-4-yl)ureido)tridecanoic acid |
| 19 | 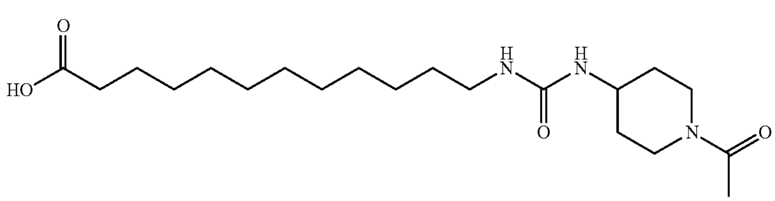 [SMILES: CC(=O)N1CCC(NC(=O)NCCCCCCCCCCCC(=O)O)CC1] | 12-(3-(1-acetylpiperidin-4-yl)ureido)dodecanoic acid |

TABLE 1-continued

| # | Structure | Name |
|---|---|---|
| 20 | 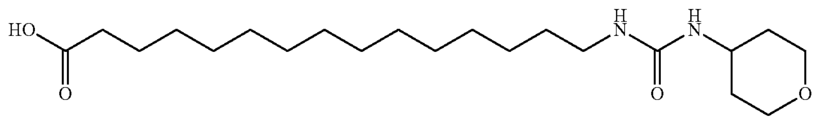 [SMILES: O=C(O)CCCCCCCCCCCCCCNC(=O)NC1CCOCC1] | 15-(3-(tetrahydro-2H-pyran-4-yl)ureido)pentadecanoic acid |
| 21 | 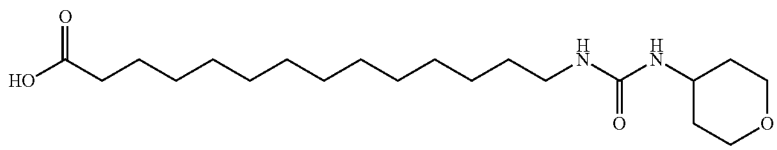 [SMILES: O=C(O)CCCCCCCCCCCCCNC(=O)NC1CCOCC1] | 14-(3-(tetrahydro-2H-pyran-4-yl)ureido)tetradecanoic acid |
| 22 | 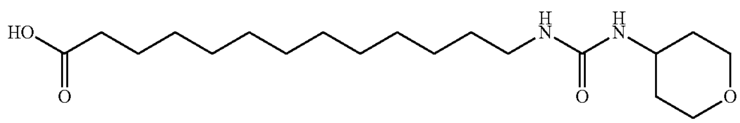 [SMILES: O=C(O)CCCCCCCCCCCCNC(=O)NC1CCOCC1] | 13-(3-(tetrahydro-2H-pyran-4-yl)ureido)tridecanoic acid |
| 23 | 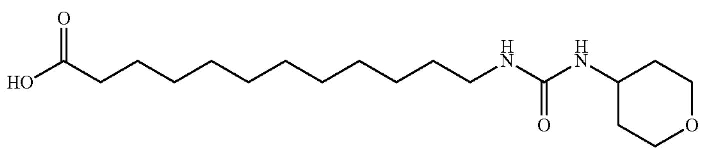 [SMILES: O=C(O)CCCCCCCCCCCNC(=O)NC1CCOCC1] | 12-(3-(tetrahydro-2H-pyran-4-yl)ureido)dodecanoic acid |
| 24 | 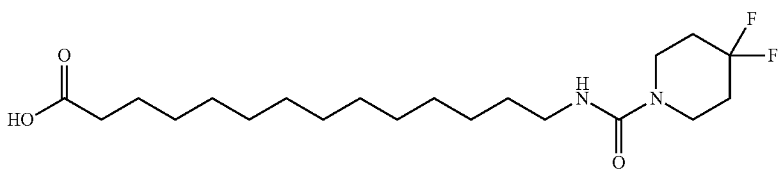 [SMILES: O=C(O)CCCCCCCCCCCCCNC(=O)N1CCC(F)(F)CC1] | 14-(4,4-difluoropiperidine-1-carboxamido)tetradecanoic acid |
| 25 | 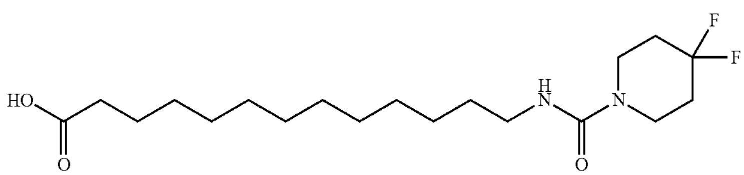 [SMILES: O=C(O)CCCCCCCCCCCCNC(=O)N1CCC(F)(F)CC1] | 13-(4,4-difluoropiperidine-1-carboxamido)tridecanoic acid |
| 26 | 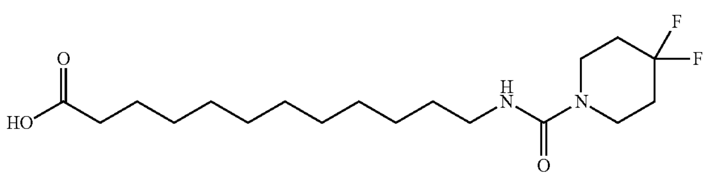 [SMILES: O=C(O)CCCCCCCCCCCNC(=O)N1CCC(F)(F)CC1] | 12-(4,4-difluoropiperidine-1-carboxamido)dodecanoic acid |
| 27 | 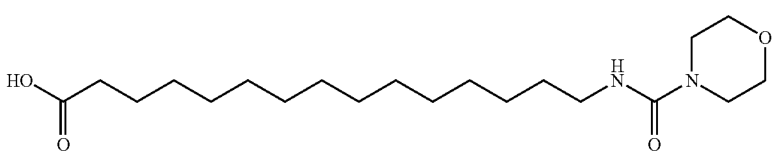 [SMILES: O=C(O)CCCCCCCCCCCCCCNC(=O)N1CCOCC1] | 15-(morpholine-4-carboxamido)pentadecanoic acid |
| 28 | 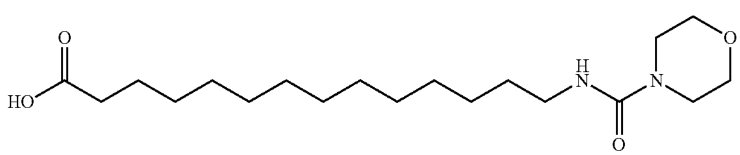 [SMILES: O=C(O)CCCCCCCCCCCCCNC(=O)N1CCOCC1] | 14-(morpholine-4-carboxamido)tetradecanoic acid |
| 29 | 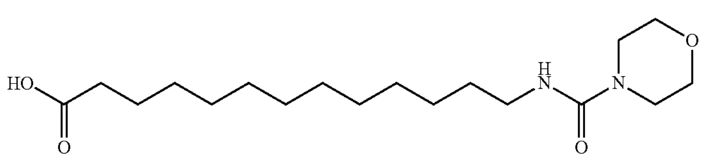 [SMILES: O=C(O)CCCCCCCCCCCCNC(=O)N1CCOCC1] | 13-(morpholine-4-carboxamido)tridecanoic acid |

TABLE 1-continued

| # | Structure | Name |
|---|---|---|
| 30 | 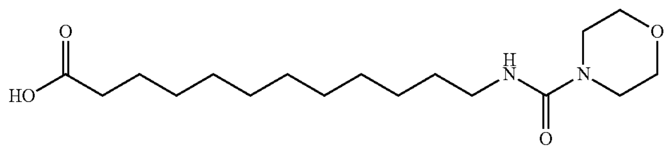 [SMILES: O=C(O)CCCCCCCCCCCNC(=O)N1CCOCC1] | 12-(morpholine-4-carboxamido) dodecanoic acid |
| 31 | 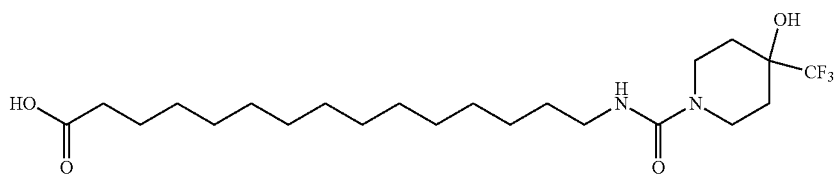 [SMILES: O=C(O)CCCCCCCCCCCCCCNC(=O)N1CCC(O)(C(F)(F)F)CC1] | 15-(4-hydroxy-4-(trifluoromethyl) piperidine-1-carboxamido) pentadecanoic acid |
| 32 | 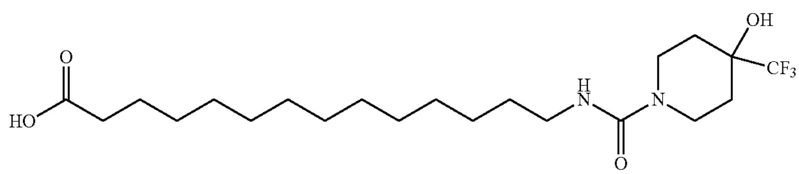 [SMILES: O=C(O)CCCCCCCCCCCCCNC(=O)N1CCC(O)(C(F)(F)F)CC1] | 14-(4-hydroxy-4-(trifluoromethyl) piperidine-1-carboxamido) tetradecanoic acid |
| 33 | 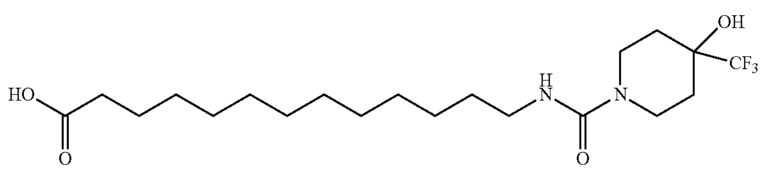 [SMILES: O=C(O)CCCCCCCCCCCCNC(=O)N1CCC(O)(C(F)(F)F)CC1] | 13-(4-hydroxy-4-(trifluoromethyl) piperidine-1-carboxamido) tridecanoic acid |
| 34 | 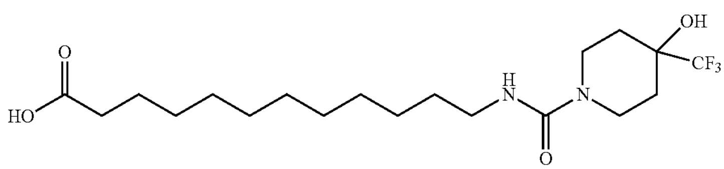 [SMILES: O=C(O)CCCCCCCCCCCNC(=O)N1CCC(O)(C(F)(F)F)CC1] | 12-(4-hydroxy-4-(trifluoromethyl) piperidine-1-carboxamido) dodecanoic acid |
| 35 | 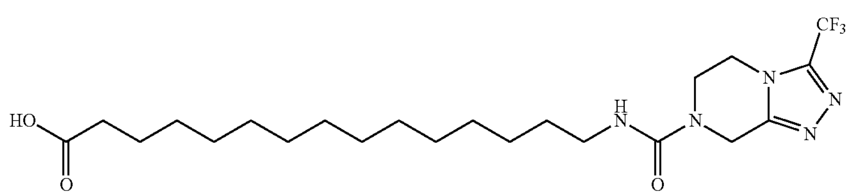 [SMILES: O=C(O)CCCCCCCCCCCCCCNC(=O)N1CCn2c(nnc2C(F)(F)F)C1] | 15-(3-(trifluoromethyl)-5,6,7,8-tetrahydro-[1,2,4]triazolo[4,3-a]pyrazine-7-carboxamido) pentadecanoic acid |
| 36 | 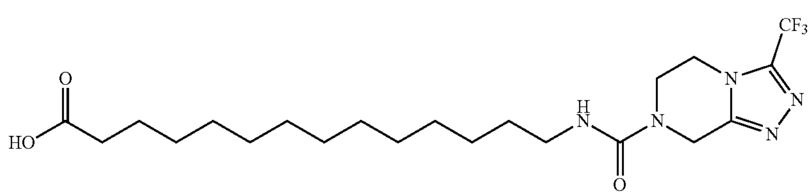 [SMILES: O=C(O)CCCCCCCCCCCCCNC(=O)N1CCn2c(nnc2C(F)(F)F)C1] | 14-(3-(trifluoromethyl)-5,6,7,8-tetrahydro-[1,2,4]triazolo[4,3-a]pyrazine-7-carboxamido) tetradecanoic acid |
| 37 | 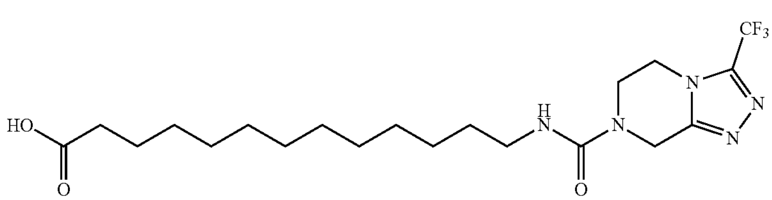 [SMILES: O=C(O)CCCCCCCCCCCCNC(=O)N1CCn2c(nnc2C(F)(F)F)C1] | 13-(3-(trifluoromethyl)-5,6,7,8-tetrahydro-[1,2,4]triazolo[4,3-a]pyrazine-7-carboxamido) tridecanoic acid |

TABLE 1-continued

| # | Structure | Name |
|---|-----------|------|
| 38 | 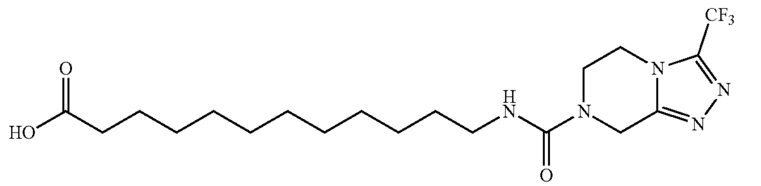 [SMILES: O=C(O)CCCCCCCCCCCNC(=O)N1CCn2c(nnc2C(F)(F)F)C1] | 12-(3-(trifluoromethyl)-5,6,7,8-tetrahydro-[1,2,4]triazolo[4,3-a]pyrazine-7-carboxamido)dodecanoic acid |
| 39 | 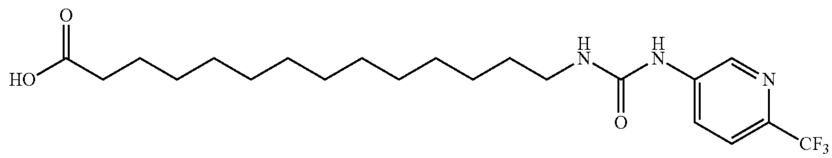 [SMILES: O=C(O)CCCCCCCCCCCCCNC(=O)Nc1ccc(C(F)(F)F)nc1] | 14-(3-(6-(trifluoromethyl)pyridin-3-yl)ureido)tetradecanoic acid |
| 40 | 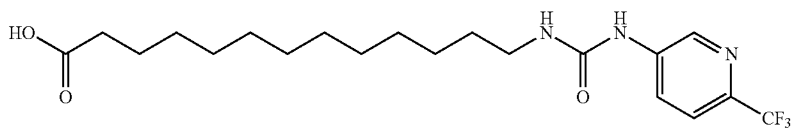 [SMILES: O=C(O)CCCCCCCCCCCCNC(=O)Nc1ccc(C(F)(F)F)nc1] | 13-(3-(6-(trifluoromethyl)pyridin-3-yl)ureido)tridecanoic acid |
| 41 | 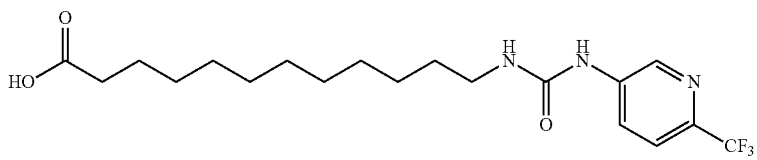 [SMILES: O=C(O)CCCCCCCCCCCNC(=O)Nc1ccc(C(F)(F)F)nc1] | 12-(3-(6-(trifluoromethyl)pyridin-3-yl)ureido)dodecanoic acid |
| 42 | 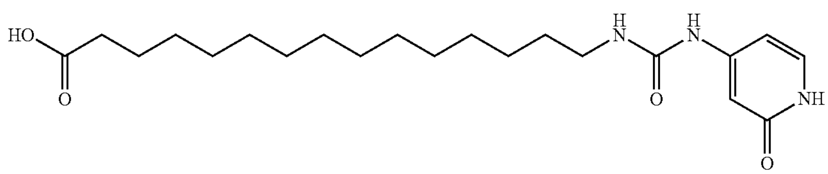 [SMILES: O=C(O)CCCCCCCCCCCCCCNC(=O)Nc1cc[nH]c(=O)c1] | 15-(3-(2-oxo-1,2-dihydropyridin-4-yl)ureido)pentadecanoic acid |
| 43 | 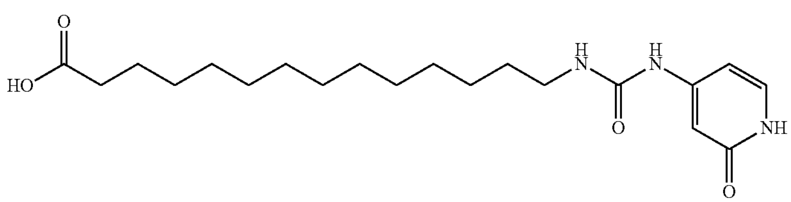 [SMILES: O=C(O)CCCCCCCCCCCCCNC(=O)Nc1cc[nH]c(=O)c1] | 14-(3-(2-oxo-1,2-dihydropyridin-4-yl)ureido)tetradecanoic acid |
| 44 | 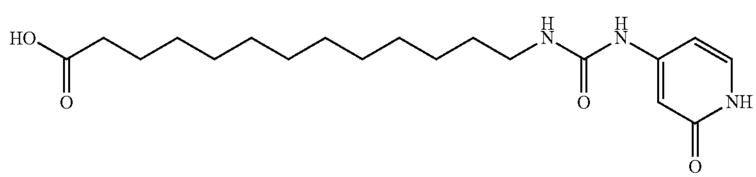 [SMILES: O=C(O)CCCCCCCCCCCCNC(=O)Nc1cc[nH]c(=O)c1] | 13-(3-(2-oxo-1,2-dihydropyridin-4-yl)ureido)tridecanoic acid |
| 45 | 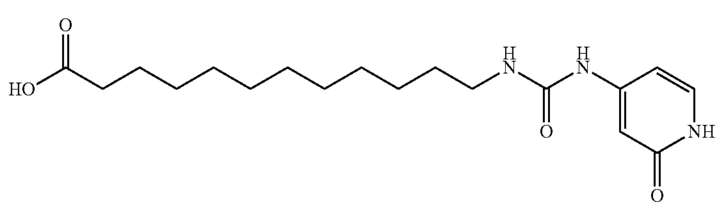 [SMILES: O=C(O)CCCCCCCCCCCNC(=O)Nc1cc[nH]c(=O)c1] | 12-(3-(2-oxo-1,2-dihydropyridin-4-yl)ureido)dodecanoic acid |
| 46 | 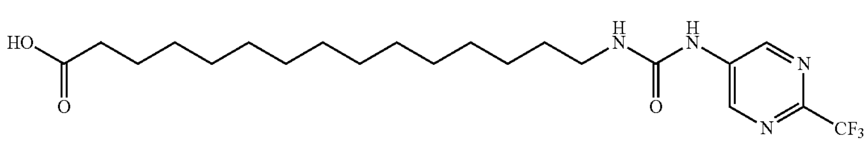 [SMILES: O=C(O)CCCCCCCCCCCCCCNC(=O)Nc1cnc(C(F)(F)F)nc1] | 15-(3-(2-(trifluoromethyl)pyrimidin-5-yl)ureido)pentadecanoic acid |

TABLE 1-continued

| # | Structure | Name |
|---|-----------|------|
| 47 | 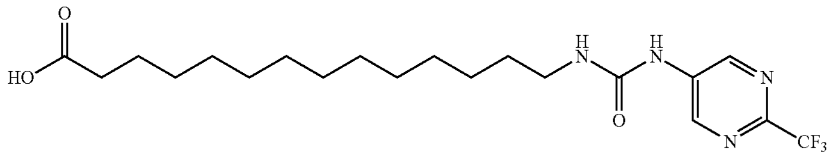 [SMILES: O=C(O)CCCCCCCCCCCCCNC(=O)Nc1cnc(C(F)(F)F)nc1] | 14-(3-(2-(trifluoromethyl)pyrimidin-5-yl)ureido)tetradecanoic acid |
| 48 | 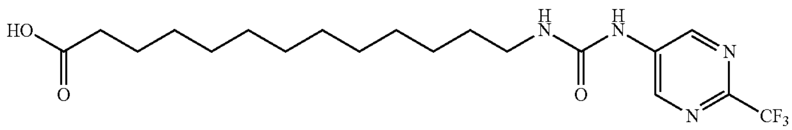 [SMILES: O=C(O)CCCCCCCCCCCCNC(=O)Nc1cnc(C(F)(F)F)nc1] | 13-(3-(2-(trifluoromethyl)pyrimidin-5-yl)ureido)tridecanoic acid |
| 49 | 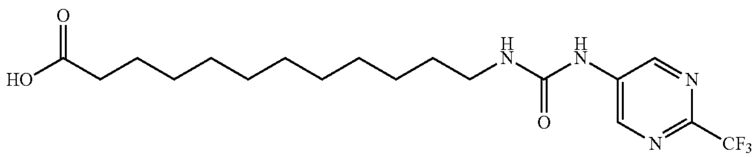 [SMILES: O=C(O)CCCCCCCCCCCNC(=O)Nc1cnc(C(F)(F)F)nc1] | 12-(3-(2-(trifluoromethyl)pyrimidin-5-yl)ureido)dodecanoic acid |
| 50 | 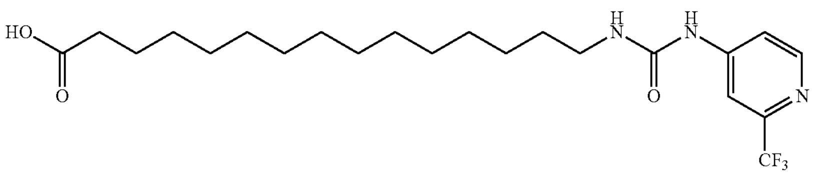 [SMILES: O=C(O)CCCCCCCCCCCCCCNC(=O)Nc1ccnc(C(F)(F)F)c1] | 15-(3-(2-(trifluoromethyl)pyridin-4-yl)ureido)pentadecanoic acid |
| 51 | 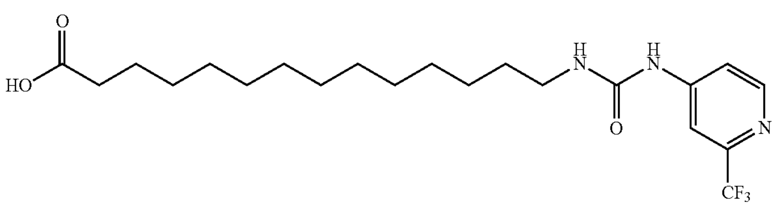 [SMILES: O=C(O)CCCCCCCCCCCCCNC(=O)Nc1ccnc(C(F)(F)F)c1] | 14-(3-(2-(trifluoromethyl)pyridin-4-yl)ureido)tetradecanoic acid |
| 52 | 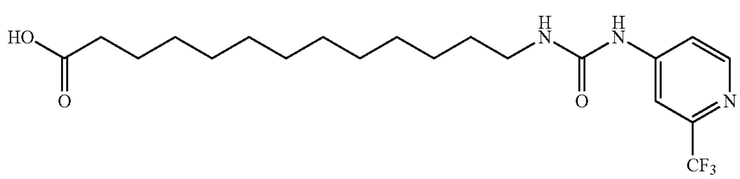 [SMILES: O=C(O)CCCCCCCCCCCCNC(=O)Nc1ccnc(C(F)(F)F)c1] | 13-(3-(2-(trifluoromethyl)pyridin-4-yl)ureido)tridecanoic acid |
| 53 | 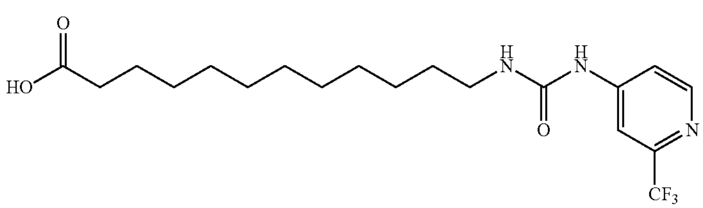 [SMILES: O=C(O)CCCCCCCCCCCNC(=O)Nc1ccnc(C(F)(F)F)c1] | 12-(3-(2-(trifluoromethyl)pyridin-4-yl)ureido)dodecanoic acid |
| 54 | 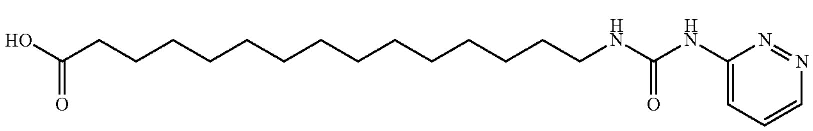 [SMILES: O=C(O)CCCCCCCCCCCCCCNC(=O)Nc1cccnn1] | 15-(3-(pyridazin-3-yl)ureido)pentadecanoic acid |
| 55 | 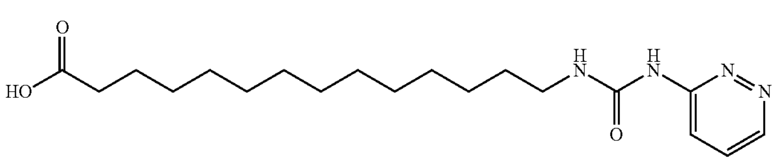 [SMILES: O=C(O)CCCCCCCCCCCCCNC(=O)Nc1cccnn1] | 14-(3-(pyridazin-3-yl)ureido)tetradecanoic acid |

TABLE 1-continued

| # | Structure | Name |
|---|---|---|
| 56 | 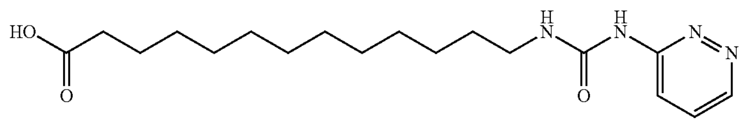 [SMILES: O=C(O)CCCCCCCCCCCCNC(=O)Nc1cccnn1] | 13-(3-(pyridazin-3-yl)ureido)tridecanoic acid |
| 57 | 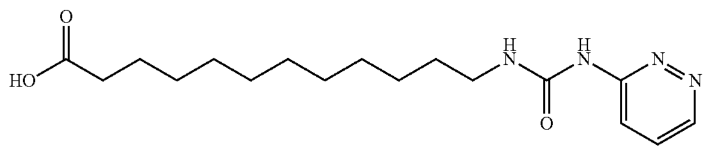 [SMILES: O=C(O)CCCCCCCCCCCNC(=O)Nc1cccnn1] | 12-(3-(pyridazin-3-yl)ureido)dodecanoic acid |
| 58 | 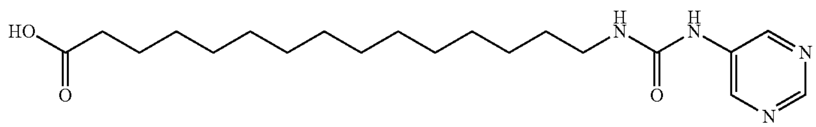 [SMILES: O=C(O)CCCCCCCCCCCCCCNC(=O)Nc1cncnc1] | 15-(3-(pyrimidin-5-yl)ureido) pentadecanoic acid |
| 59 | 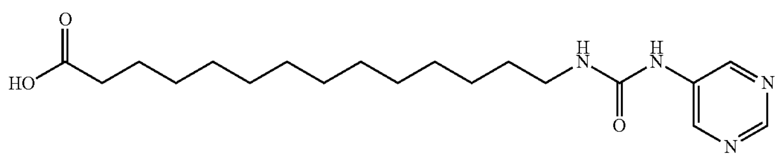 [SMILES: O=C(O)CCCCCCCCCCCCCNC(=O)Nc1cncnc1] | 14-(3-(pyrimidin-5-yl)ureido) tetradecanoic acid |
| 60 | 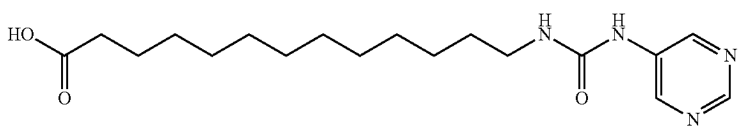 [SMILES: O=C(O)CCCCCCCCCCCCNC(=O)Nc1cncnc1] | 13-(3-(pyrimidin-5-yl)ureido)tridecanoic acid |
| 61 | 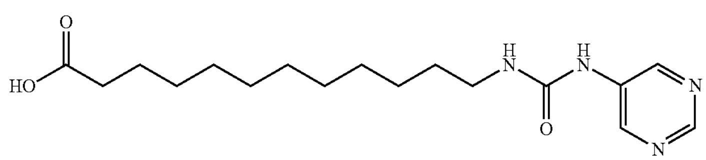 [SMILES: O=C(O)CCCCCCCCCCCNC(=O)Nc1cncnc1] | 12-(3-(pyrimidin-5-yl)ureido)dodecanoic acid |
| 62 | 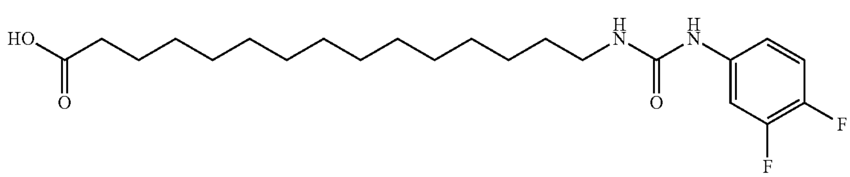 [SMILES: O=C(O)CCCCCCCCCCCCCCNC(=O)Nc1ccc(F)c(F)c1] | 15-(3-(3,4-difluorophenyl) ureido) pentadecanoic acid |
| 63 | 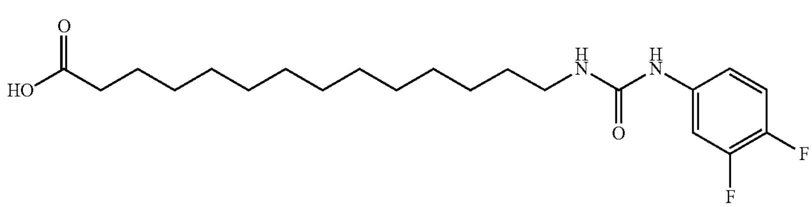 [SMILES: O=C(O)CCCCCCCCCCCCCNC(=O)Nc1ccc(F)c(F)c1] | 14-(3-(3,4-difluorophenyl) ureido) tetradecanoic acid |
| 64 | 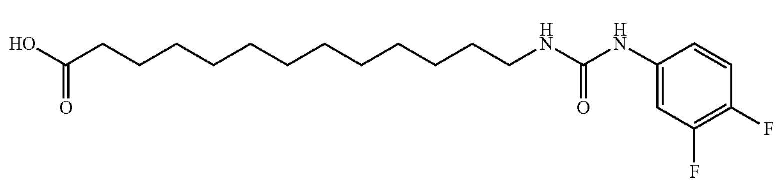 [SMILES: O=C(O)CCCCCCCCCCCCNC(=O)Nc1ccc(F)c(F)c1] | 13-(3-(3,4-difluorophenyl) ureido) tridecanoic acid |

TABLE 1-continued

| # | Structure | Name |
|---|---|---|
| 65 | 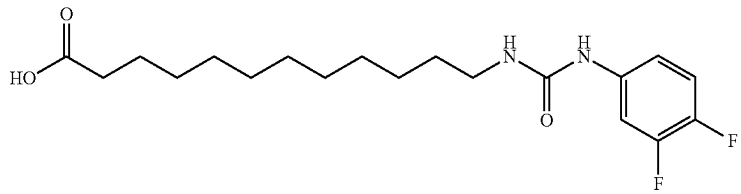 [SMILES: O=C(O)CCCCCCCCCCCNC(=O)Nc1ccc(F)c(F)c1] | 12-(3-(3,4-difluorophenyl)ureido)dodecanoic acid |
| 66 | 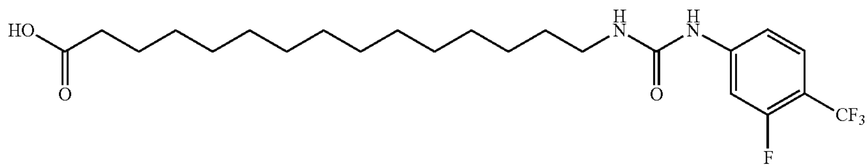 [SMILES: O=C(O)CCCCCCCCCCCCCCNC(=O)Nc1ccc(C(F)(F)F)c(F)c1] | 15-(3-(3-fluoro-4-(trifluoromethyl)phenyl)ureido)pentadecanoic acid |
| 67 | 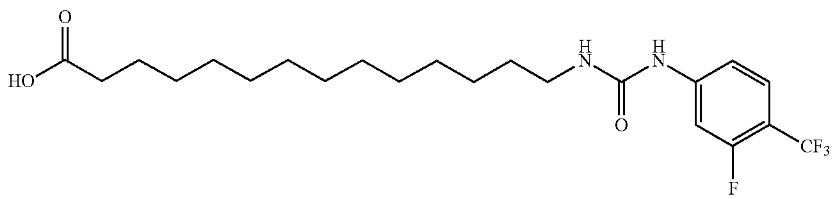 [SMILES: O=C(O)CCCCCCCCCCCCCNC(=O)Nc1ccc(C(F)(F)F)c(F)c1] | 14-(3-(3-fluoro-4-(trifluoromethyl)phenyl)ureido)tetradecanoic acid |
| 68 | 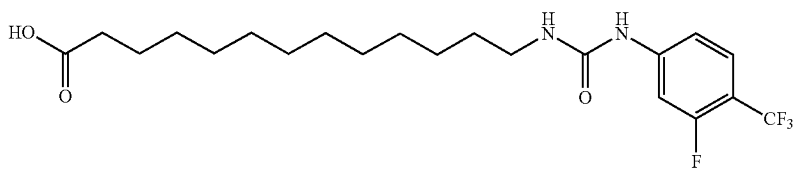 [SMILES: O=C(O)CCCCCCCCCCCCNC(=O)Nc1ccc(C(F)(F)F)c(F)c1] | 13-(3-(3-fluoro-4-(trifluoromethyl)phenyl)ureido)tridecanoic acid |
| 69 | 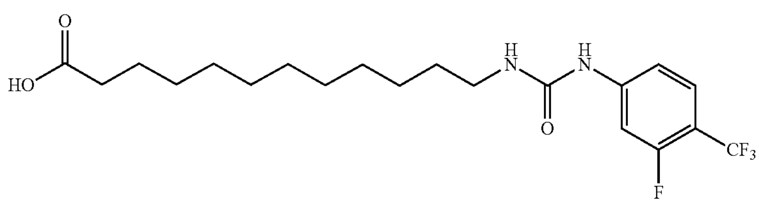 [SMILES: O=C(O)CCCCCCCCCCCNC(=O)Nc1ccc(C(F)(F)F)c(F)c1] | 12-(3-(3-fluoro-4-(trifluoromethyl)phenyl)ureido)dodecanoic acid |
| 70 | 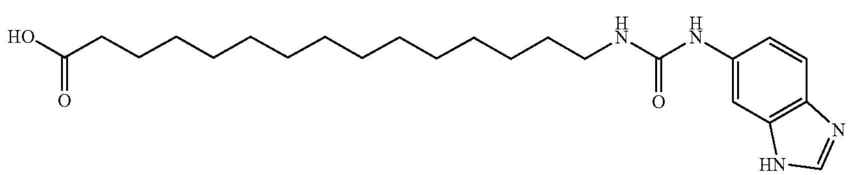 [SMILES: O=C(O)CCCCCCCCCCCCCCNC(=O)Nc1ccc2nc[nH]c2c1] | 15-(3-(1H-benzo[d]imidazol-6-yl)ureido)pentadecanoic acid |
| 71 | 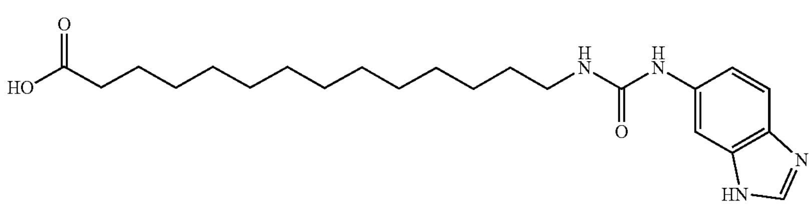 [SMILES: O=C(O)CCCCCCCCCCCCCNC(=O)Nc1ccc2nc[nH]c2c1] | 14-(3-(1H-benzo[d]imidazol-6-yl)ureido)tetradecanoic acid |
| 72 | 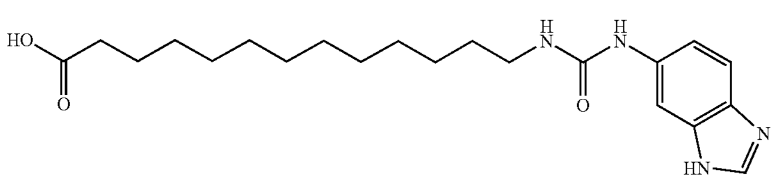 [SMILES: O=C(O)CCCCCCCCCCCCNC(=O)Nc1ccc2nc[nH]c2c1] | 13-(3-(1H-benzo[d]imidazol-6-yl)ureido)tridecanoic acid |

TABLE 1-continued

| # | Structure | Name |
|---|---|---|
| 73 | 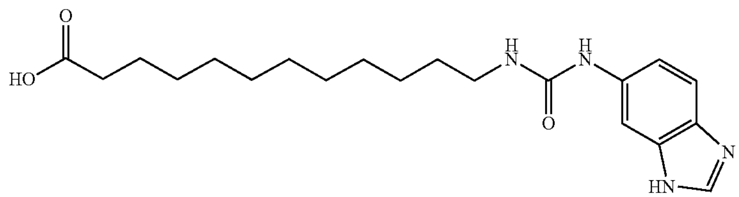 [SMILES: O=C(O)CCCCCCCCCCCNC(=O)Nc1ccc2nc[nH]c2c1] | 12-(3-(1H-benzo[d]imidazol-6-yl)ureido)dodecanoic acid |
| 74 | 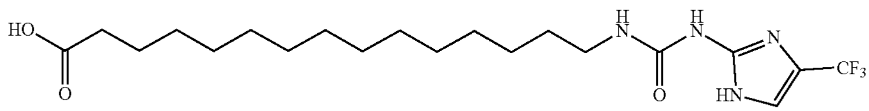 [SMILES: O=C(O)CCCCCCCCCCCCCCNC(=O)Nc1nc(C(F)(F)F)c[nH]1] | 15-(3-(4-(trifluoromethyl)-1H-imidazol-2-yl)ureido)pentadecanoic acid |
| 75 | 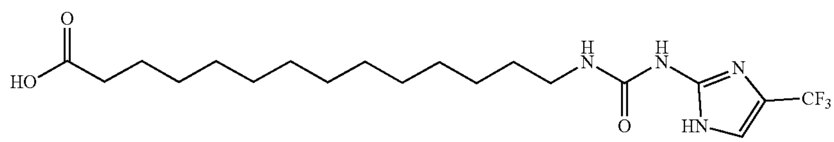 [SMILES: O=C(O)CCCCCCCCCCCCCNC(=O)Nc1nc(C(F)(F)F)c[nH]1] | 14-(3-(4-(trifluoromethyl)-1H-imidazol-2-yl)ureido)tetradecanoic acid |
| 76 | 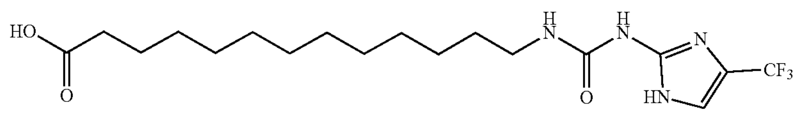 [SMILES: O=C(O)CCCCCCCCCCCCNC(=O)Nc1nc(C(F)(F)F)c[nH]1] | 13-(3-(4-(trifluoromethyl)-1H-imidazol-2-yl)ureido)tridecanoic acid |
| 77 | 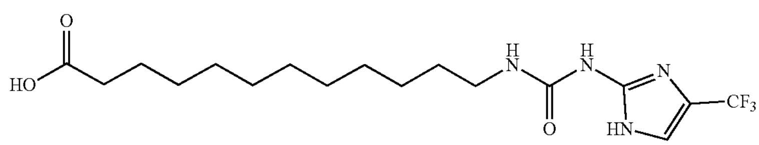 [SMILES: O=C(O)CCCCCCCCCCCNC(=O)Nc1nc(C(F)(F)F)c[nH]1] | 12-(3-(4-(trifluoromethyl)-1H-imidazol-2-yl)ureido)dodecanoic acid |
| 78 | 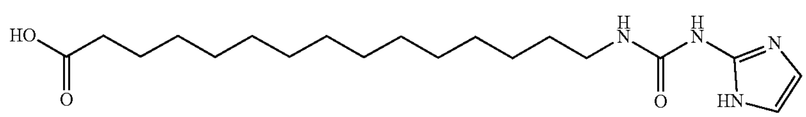 [SMILES: O=C(O)CCCCCCCCCCCCCCNC(=O)Nc1ncc[nH]1] | 15-(3-(1H-imidazol-2-yl)ureido)pentadecanoic acid |
| 79 | 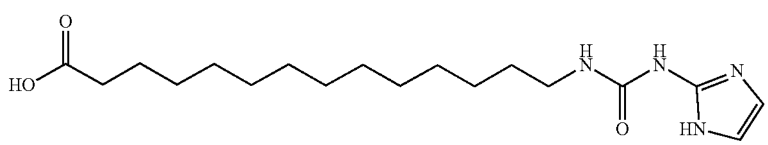 [SMILES: O=C(O)CCCCCCCCCCCCCNC(=O)Nc1ncc[nH]1] | 14-(3-(1H-imidazol-2-yl)ureido)tetradecanoic acid |
| 80 | 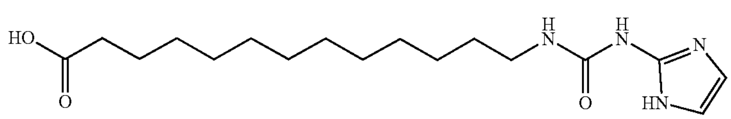 [SMILES: O=C(O)CCCCCCCCCCCCNC(=O)Nc1ncc[nH]1] | 13-(3-(1H-imidazol-2-yl)ureido)tridecanoic acid |
| 81 | 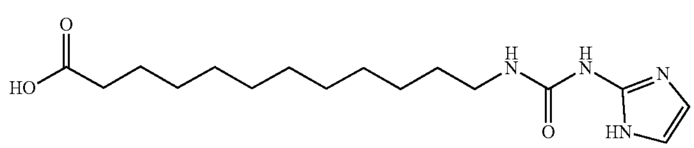 [SMILES: O=C(O)CCCCCCCCCCCNC(=O)Nc1ncc[nH]1] | 12-(3-(1H-imidazol-2-yl)ureido)dodecanoic acid |
| 82 | 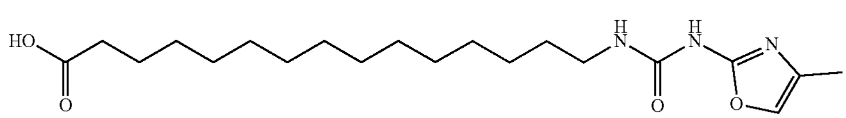 [SMILES: Cc1coc(NC(=O)NCCCCCCCCCCCCCCC(=O)O)n1] | 15-(3-(4-methyloxazol-2-yl)ureido)pentadecanoic acid |
| 83 | 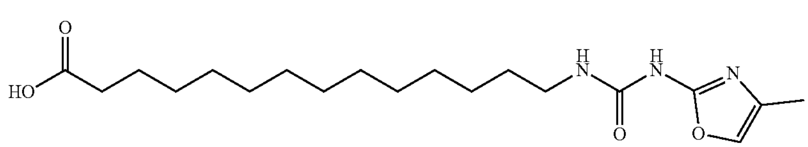 [SMILES: Cc1coc(NC(=O)NCCCCCCCCCCCCCC(=O)O)n1] | 14-(3-(4-methyloxazol-2-yl)ureido)tetradecanoic acid |

TABLE 1-continued

| # | Structure | Name |
|---|---|---|
| 84 | 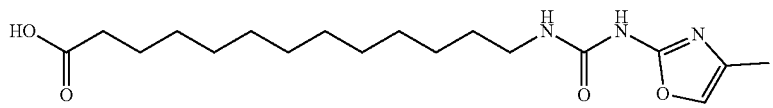 [SMILES: Cc1coc(NC(=O)NCCCCCCCCCCCCC(=O)O)n1] | 13-(3-(4-methyloxazol-2-yl)ureido)tridecanoic acid |
| 85 | 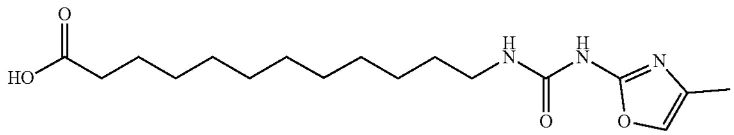 [SMILES: Cc1coc(NC(=O)NCCCCCCCCCCCC(=O)O)n1] | 12-(3-(4-methyloxazol-2-yl)ureido)dodecanoic acid |
| 86 | 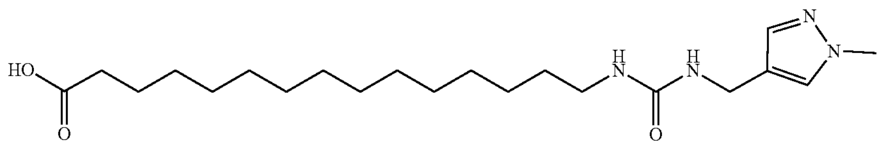 [SMILES: Cn1cc(CNC(=O)NCCCCCCCCCCCCCCC(=O)O)cn1] | 15-(3-((1-methyl-1H-pyrazol-4-yl)methyl)ureido)pentadecanoic acid |
| 87 | 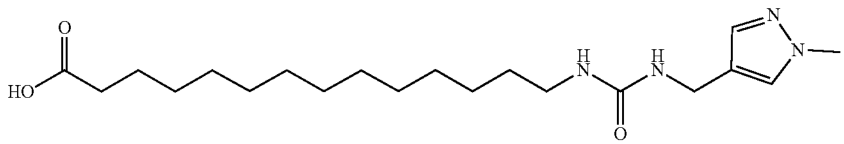 [SMILES: Cn1cc(CNC(=O)NCCCCCCCCCCCCCC(=O)O)cn1] | 14-(3-((1-methyl-1H-pyrazol-4-yl)methyl)ureido)tetradecanoic acid |
| 88 | 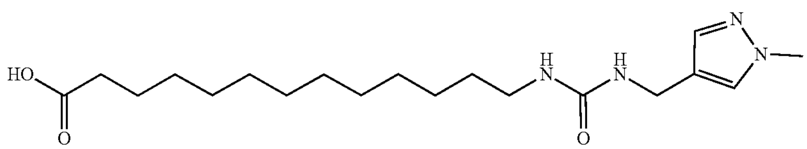 [SMILES: Cn1cc(CNC(=O)NCCCCCCCCCCCCC(=O)O)cn1] | 13-(3-((1-methyl-1H-pyrazol-4-yl)methyl)ureido)tridecanoic acid |
| 89 | 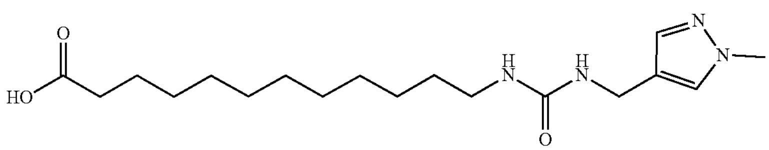 [SMILES: Cn1cc(CNC(=O)NCCCCCCCCCCCC(=O)O)cn1] | 12-(3-((1-methyl-1H-pyrazol-4-yl)methyl)ureido)dodecanoic acid |
| 90 | 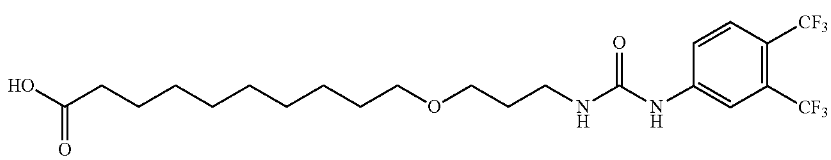 [SMILES: O=C(O)CCCCCCCCCOCCCNC(=O)Nc1ccc(C(F)(F)F)c(C(F)(F)F)c1] | 10-(3-(3-(3,4-bis(trifluoromethyl)phenyl)ureido)propoxy)decanoic acid |
| 91 | 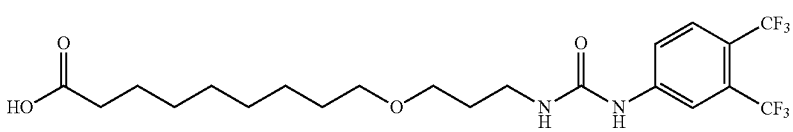 | 9-(3-(3-(3,4-bis(trifluoromethyl)phenyl)ureido)propoxy)nonanoic acid |
| 92 | 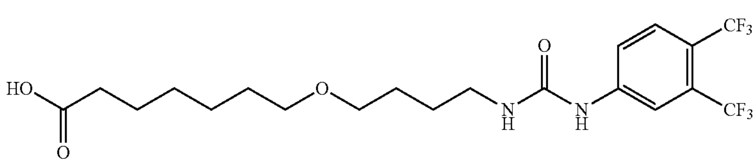 [SMILES: O=C(O)CCCCCCOCCCCNC(=O)Nc1ccc(C(F)(F)F)c(C(F)(F)F)c1] | 7-(4-(3-(3,4-bis(trifluoromethyl)phenyl)ureido)butoxy)heptanoic acid |
| 93 | 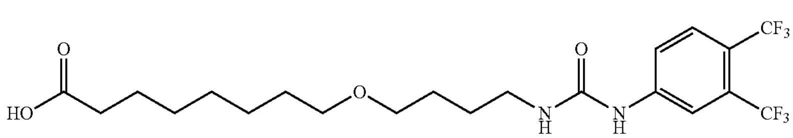 [SMILES: O=C(O)CCCCCCCOCCCCNC(=O)Nc1ccc(C(F)(F)F)c(C(F)(F)F)c1] | 8-(4-(3-(3,4-bis(trifluoromethyl)phenyl)ureido)butoxy)octanoic acid |
| 94 | 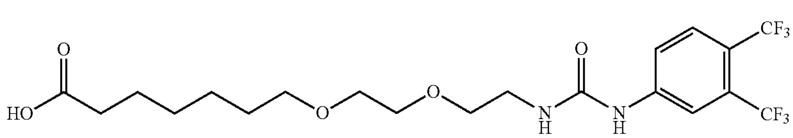 [SMILES: O=C(O)CCCCCCOCCOCCNC(=O)Nc1ccc(C(F)(F)F)c(C(F)(F)F)c1] | 7-(2-(2-(3-(3,4-bis(trifluoromethyl)phenyl)ureido)ethoxy)ethoxy)heptanoic acid |

TABLE 1-continued

| # | Structure | Name |
|---|---|---|
| 95 | 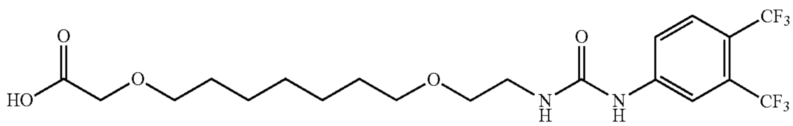 [SMILES: O=C(O)COCCCCCCCOCCNC(=O)Nc1ccc(C(F)(F)F)c(C(F)(F)F)c1] | 2-((7-(2-(3-(3,4-bis(trifluoromethyl)phenyl)ureido)ethoxy)heptyl)oxy)acetic acid |
| 96 | 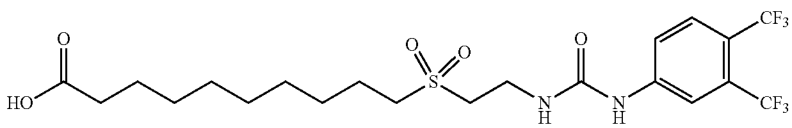 [SMILES: O=C(O)CCCCCCCCCS(=O)(=O)CCNC(=O)Nc1ccc(C(F)(F)F)c(C(F)(F)F)c1] | 10-((2-(3-(3,4-bis(trifluoromethyl)phenyl)ureido)ethyl)sulfonyl)decanoic acid |
| 97 | 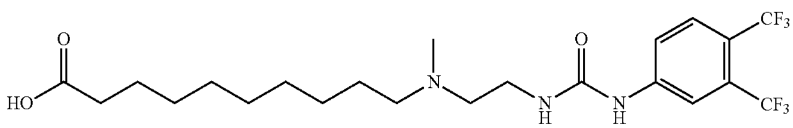 [SMILES: CN(CCCCCCCCCC(=O)O)CCNC(=O)Nc1ccc(C(F)(F)F)c(C(F)(F)F)c1] | 10-((2-(3-(3,4-bis(trifluoromethyl)phenyl)ureido)ethyl)(methyl)amino)decanoic acid |
| 98 | 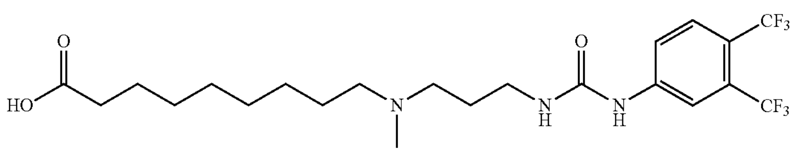 [SMILES: CN(CCCCCCCCC(=O)O)CCCNC(=O)Nc1ccc(C(F)(F)F)c(C(F)(F)F)c1] | 9-((3-(3-(3,4-bis(trifluoromethyl)phenyl)ureido)propyl)(methyl)amino)nonanoic acid |
| 99 | 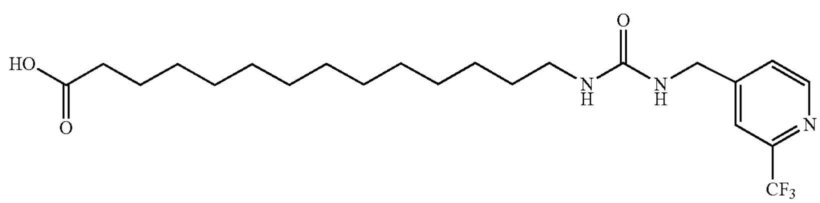 [SMILES: O=C(O)CCCCCCCCCCCCCNC(=O)NCc1ccnc(C(F)(F)F)c1] | 14-(3-((2-(trifluoromethyl)pyridin-4-yl)methyl)ureido)tetradecanoic acid |
| 100 | 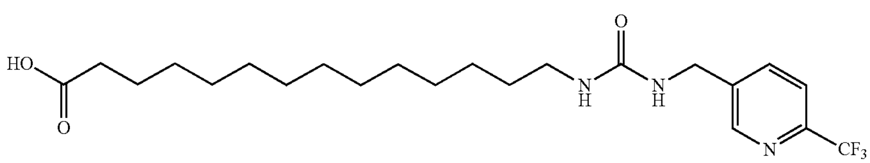 [SMILES: O=C(O)CCCCCCCCCCCCCNC(=O)NCc1ccc(C(F)(F)F)nc1] | 14-(3-((6-(trifluoromethyl)pyridin-3-yl)methyl)ureido)tetradecanoic acid |
| 101 | 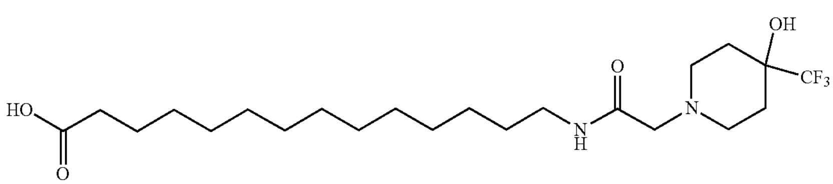 [SMILES: O=C(O)CCCCCCCCCCCCCNC(=O)CN1CCC(O)(C(F)(F)F)CC1] | 14-(2-(4-hydroxy-4-(trifluoromethyl)piperidin-1-yl)acetamido)tetradecanoic acid |
| 102 | 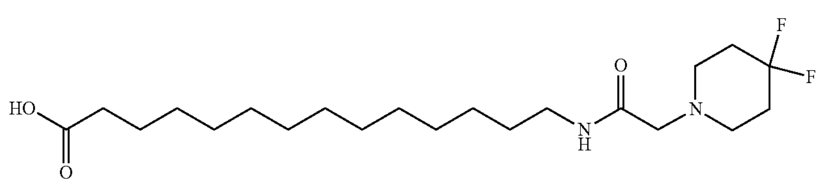 [SMILES: O=C(O)CCCCCCCCCCCCCNC(=O)CN1CCC(F)(F)CC1] | 14-(2-(4,4-difluoropiperidin-1-yl)acetamido)tetradecanoic acid |
| 103 | 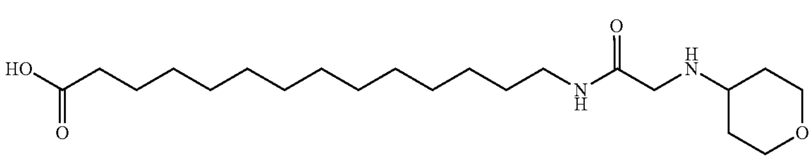 [SMILES: O=C(O)CCCCCCCCCCCCCNC(=O)CNC1CCOCC1] | 14-(2-((tetrahydro-2H-pyran-4-yl)amino)acetamido)tetradecanoic acid |

TABLE 1-continued

| # | Structure | Name |
|---|---|---|
| 104 | 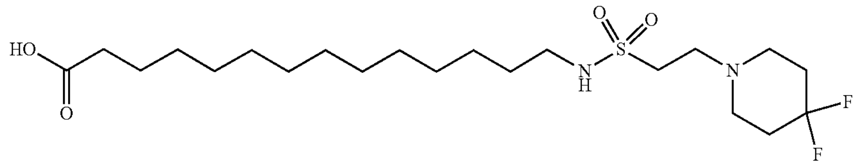 [SMILES: O=C(O)CCCCCCCCCCCCCNS(=O)(=O)CCN1CCC(F)(F)CC1] | 14-((2-(4,4-difluoropiperidin-1-yl)ethyl)sulfonamido)tetradecanoic acid |
| 105 | 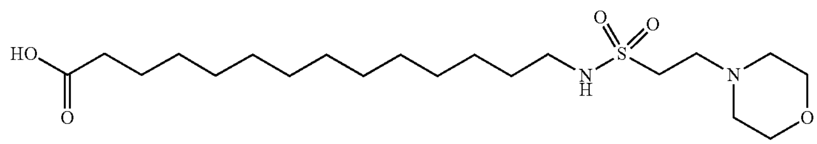 [SMILES: O=C(O)CCCCCCCCCCCCCNS(=O)(=O)CCN1CCOCC1] | 14-((2-morpholinoethyl)sulfonamido)tetradecanoic acid |
| 106 | 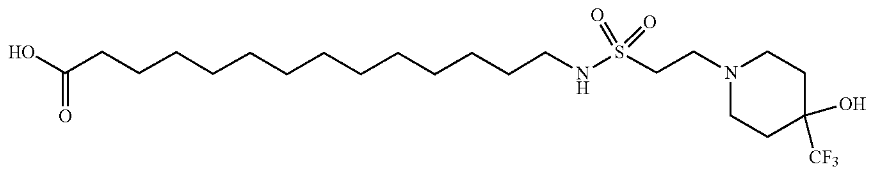 [SMILES: O=C(O)CCCCCCCCCCCCCNS(=O)(=O)CCN1CCC(O)(C(F)(F)F)CC1] | 14-((2-(4-hydroxy-4-(trifluoromethyl)piperidin-1-yl)ethyl)sulfonamido)tetradecanoic acid |
| 107 | 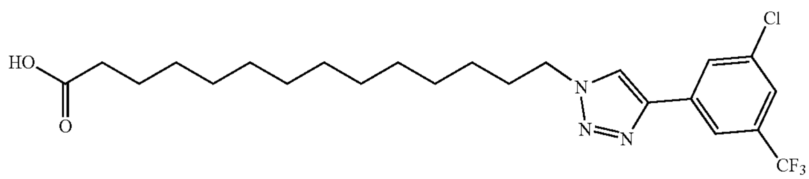 [SMILES: O=C(O)CCCCCCCCCCCCCn1cc(-c2cc(Cl)cc(C(F)(F)F)c2)nn1] | 14-(4-(3-chloro-5-(trifluoromethyl)phenyl)-1H-1,2,3-triazol-1-yl)tetradecanoic acid |
| 108 | 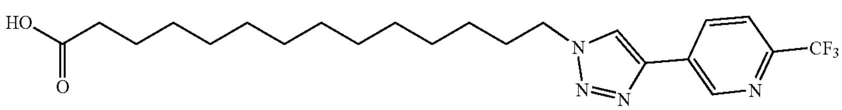 [SMILES: O=C(O)CCCCCCCCCCCCCn1cc(-c2ccc(C(F)(F)F)nc2)nn1] | 14-(4-(6-(trifluoromethyl)pyridin-3-yl)-1H-1,2,3-triazol-1-yl)tetradecanoic acid |
| 109 | 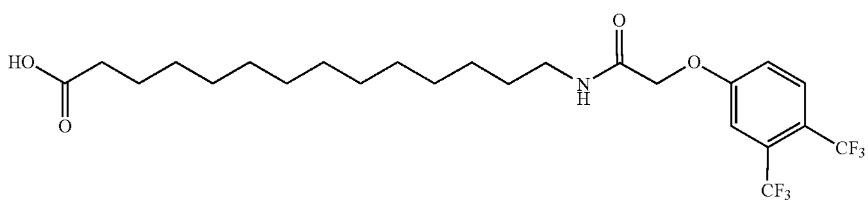 [SMILES: O=C(O)CCCCCCCCCCCCCNC(=O)COc1ccc(C(F)(F)F)c(C(F)(F)F)c1] | 14-(2-(3,4-bis(trifluoromethyl)phenoxy)acetamido)tetradecanoic acid |
| 110 | 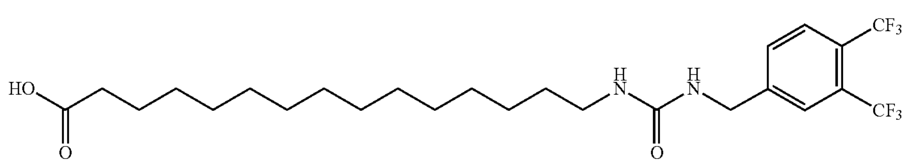 [SMILES: O=C(O)CCCCCCCCCCCCCCNC(=O)NCc1ccc(C(F)(F)F)c(C(F)(F)F)c1] | 15-(3-(3,4-bis(trifluoromethyl)benzyl)ureido)pentadecanoic acid |
| 111 | 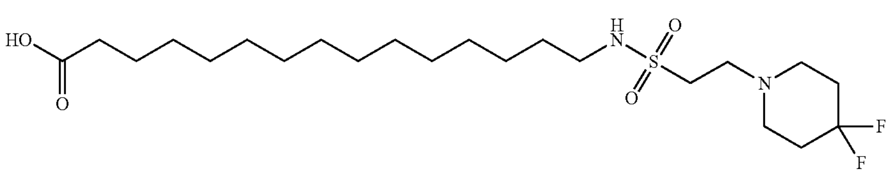 [SMILES: O=C(O)CCCCCCCCCCCCCCNS(=O)(=O)CCN1CCC(F)(F)CC1] | 15-((2-(4,4-difluoropiperidin-1-yl)ethyl)sulfonamido)pentadecanoic acid |

Preparation of Compounds

The compounds used in the chemical reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, NH), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Alternatively, specific and analogous reactants can be identified through the indices of known chemicals and reactions prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compound described herein is P. H. Stahl & C. G. Wermuth "Handbook of Pharmaceutical Salts", Verlag Helvetica Chimica Acta, Zurich, 2002.

The compounds described herein are prepared using the general methods in the art of organic synthesis, as described in the Examples section. Alternative synthetic methods are also used to generate the compounds described herein.

Methods of Treatment

In certain embodiments, the compounds described herein are used to treat or prevent a disease or condition. The compounds described herein are in some instances promoters of apoptosis, and are variously used to treat cell-division or proliferative diseases. In some embodiments, the compounds described herein target mitochondria, leading to cell death. In some embodiments, the compounds described herein influence downstream cell signaling pathways that promote selective apoptosis of rapidly dividing cells. In some embodiments, compounds described herein deplete one or more phospholipids, such as cardiolipin. In other embodiments, the compounds described herein are used to treat cardiovascular, autoimmune/inflammatory diseases, or dry eye syndrome.

Diseases or conditions treated or prevented by the compounds described herein in some embodiments include proliferative diseases. In some embodiments, a proliferative disease is cancer. Cancers of various organs or tissues such as heart, liver, brain, blood, skin or other types of cancers are in some embodiments treatable or preventable by the compounds described herein. In some embodiments cancers include brain cancer, skin cancer, bladder cancer, lung cancer, prostate cancer, breast cancer, uterine cancer, ovarian cancer, colon cancer, thyroid cancer, or pancreatic cancer. In some embodiments, the cancer is a tumor. In some embodiments, the cancer is breast cancer. In some embodiments, the breast cancer is metastatic. In some embodiments, the cancer comprises is a solid tumor.

In some embodiments cancers include breast, colon, lung, and prostate cancers, cancer of the adrenal cortex, ACTH-producing tumor, bladder cancer, brain cancer, Ewing's sarcoma, head and neck cancer (including mouth cancer and larynx cancer), thyroid cancer, trophoblastic neoplasms, Wilms' tumor, kidney cancer (including renal cell carcinoma), liver cancer, Kaposi's sarcoma, bone cancer (including osteomas and sarcomas such as fibrosarcoma and osteosarcoma), lung cancer including small and non-small cell lung cancers, mesothelioma, malignant peritoneal effusion, malignant pleural effusion, skin cancers (including malignant melanoma, tumor progression of human skin keratinocytes, squamous cell carcinoma, basal cell carcinoma, and hemangiopericytoma), gastrointestinal cancers (including esophageal cancer, stomach/gastric cancer, colorectal cancer, polyps associated with colorectal neoplasms, pancreatic cancer and gallbladder cancer), cancers of the female reproductive tract (including uterine cancer, endometrial cancer, ovarian cancer, ovarian (germ cell) cancer and solid tumors in the ovarian follicle, vaginal cancer, cancer of the vulva, and cervical cancer), breast cancer (small cell and ductal), male reproductive system (penile cancer, testicular cancer), and eye cancers (retinoblastoma, intraocular lymphoma, hemangioma). In some embodiments, cancers include non-melanoma skin cancer, lung cancer, brain cancer, breast cancer, prostate cancer, colorectal cancer, bladder cancer, melanoma, non-Hodgkin lymphoma, kidney cancer, leukemia, pancreatic cancer, mesothelioma, head and neck cancer, gastric cancer, small cell lung cancer, or eye cancer.

In some embodiments breast cancers include Luminal A, Luminal B, triple-negative, Her2-enriched, and normal-like breast cancer.

Cancers including cancers of different outcomes are in some embodiments treated or prevented with the compounds described herein. In some embodiments, cancers are malignant cancers. In some embodiments, cancers are benign. In some embodiments, compounds described herein are used to treat metastatic cancers. In some embodiments the cancer is a primary cancer, originating in a specific tissue. In some embodiments, the cancer spreads from a primary site to a secondary site in a different location, such as a different organ or tissue. In some embodiments, compounds described herein facilitate remission of a previously treated or diagnosed tumor.

In various aspects of the invention, compounds described herein often are used in combination with other cancer therapies, such as additional chemotherapy (including immune-stimulating drugs), surgery, radiation treatment, or other treatment used in the art for the treatment or prevention of cancer.

Further provided herein compounds used to treat cardiovascular diseases. Non-limited examples of cardiovascular diseases include heart disease (such as coronary artery disease, arrhythmia, rheumatic heart disease, cardiomyopathy, hypertriglyceridemia, heart valve disease, aneurysm, pericardial diseases, myocardial infarction, or other heart disease), peripheral arterial disease, vascular disease (such as cerebrovascular diseases, deep venous thrombosis (DVT), renal artery stenosis, pulmonary embolism, hypertension, atherosclerosis), or other cardiovascular disease or related disease, such as diabetes. In some embodiments, the compounds described herein lower triglyceride levels.

In some cases, compounds are used to treat autoimmune or inflammatory diseases. Inflammatory or autoimmune diseases variously comprise rheumatoid arthritis, Crohn's disease, ulcerative colitis, psoriasis, lupus erythematosus, multiple sclerosis or migraine headaches. In some embodiments, the compounds described herein lower levels of pro-inflammatory cytokines, such as interleukins (e.g., IL-1 or other interleukin).

Described herein are compounds to treat dry eye syndrome ("dry eye"). Dry eye syndrome may be caused by any number of contributing diseases or conditions. For example, diseases or conditions causing dry eye include keratoconjunctivitis sicca, diabetes, rheumatoid arthritis, lupus, scleroderma, Sjogren's syndrome, aqueous tear deficiency, lipid abnormalities, lacrimal gland dysfunction, lacrimal gland inflammation, meibomian gland dysfunction, thyroid disorders or vitamin A deficiency. In some embodiments, the disease causes inflammation. In some embodiments, the disease is keratoconjunctivitis sicca. Causes of dry eye include but are not limited to specific types of drugs, such as antihistamines, decongestants, hormones/steroids, antidepressants, blood pressure medication, acne medication, or drugs used to treat Parkinson's diseases. Dry eye is also in some cases caused by eye surgery, or environmental factors such as wind, dust, smoke, or activities such as driving or reading. In some embodiments, the compounds described herein increase tear production or secretion. In some embodiments, compounds described herein reduce tear evaporation.

Pharmaceutical Compositions

In certain embodiments, the compound as described herein is administered as a pure chemical. In other embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: *The Science and Practice of Pharmacy* (Gennaro, 21$^{st}$ Ed. Mack Pub. Co., Easton, Pa. (2005)).

Provided herein are pharmaceutical compositions comprising at least one compound described herein, or a stereoisomer, pharmaceutically acceptable salt, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject or patient) of the composition.

One embodiment provides a pharmaceutical composition comprising a compound described herein, or a pharmaceutically acceptable salt thereof, and a pharmaceutically acceptable excipient. In one embodiment, the pharmaceutical compositions are provided in a dosage form for oral administration, which comprise a compound provided herein, and one or more pharmaceutically acceptable excipients or carriers.

In certain embodiments, a compound described herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

In some embodiments, the pharmaceutical compositions provided herein are formulated for oral administration in tablet, capsule, powder, or liquid form. In some embodiments, a tablet comprises a solid carrier or an adjuvant. Liquid pharmaceutical compositions generally comprise a liquid carrier such as water, petroleum, animal or vegetable oils, mineral oil, or synthetic oil. In some embodiments, physiological saline solution, dextrose or other saccharide solution, or glycols are optionally included. In some embodiments, a capsule comprises a solid carrier such as gelatin.

In another embodiment, the pharmaceutical compositions are provided in a dosage form for parenteral administration, which comprise a compound provided herein, and one or more pharmaceutically acceptable excipients or carriers. Where pharmaceutical compositions are formulated for intravenous, cutaneous or subcutaneous injection, the active ingredient is in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. In some embodiments, preservatives, stabilizers, buffers, antioxidants, and/or other additives are included. Pharmaceutical compositions are in some embodiments pH-adjusted with acids or bases, such as hydrochloric acid and/or sodium hydroxide.

In yet another embodiment, the pharmaceutical compositions are provided in a dosage form for topical administration, which comprise a compound provided herein, and one or more pharmaceutically acceptable excipients or carriers.

In some embodiments, the pharmaceutical compositions comprising a compound provided herein are provided in a dosage form for ophthalmic administration, such as eye drops. Such formulations are variously used to treat diseases and conditions described herein, such as dry eyes. Such ophthalmic formulations often comprise any number of ingredients, including lubricants, oils, preservatives, stabilizers, redness reducers, buffers, antioxidants, antihistamines, anti-inflammatory agents, vasoconstrictors, excipients, carriers, and/or other additives. Ophthalmic formulations in some instances comprise ingredients such as polyvinyl alcohol, povidone, carboxymethylcellulose salts, glycerin, polysorbate 80, mineral oil, white petrolatum, polyethylene glycol, propylene glycol, hypromellose (for example, 2910), dextran, (such as dextran 70), hydroxypropyl methylcellulose, carmellose salts, zinc sulfate, or other ingredient. In some embodiments, ophthalmic formulations comprise vasocontrictors such as tetrahydrozoline, naphazoline HCl, phenylephrine HCl, or other vasoconstrictor.

Ophthalmic formulations of the compounds described herein in some embodiments comprise ingredients such as castor oil, sorbitol, boric acid, butylated hydroxyl toluene, calcium chloride, calcium chloride dihydrate, carbomer copolymer type A, castor oil, citric acid, dextrose, dibasic sodium phosphate, dimyristoyl phosphatidylglycerol, disodium edetate dihydrate, erythritol, ethanol, flaxseed oil, gellan gum, GenAqua (sodium perborate), glycerin, glycerol, glycine, hydrochloric acid, hydroxyalkylphosphonate, hydroxyethylcellulose, hydroxypropyl guar, lecithin, levocarnitine, magnesium chloride, mineral oil, monobasic sodium phosphate, octoxynol-40, pemulen TR-2, phosphonic acid, polixetonium, poloxamer 188, polyoxyl 35 castor oil, polyoxyl 40 stearate, polysorbate 80, potassium chloride, PURITE (stabilized oxychloro complex), sodium alginate, sodium bicarbonate, sodium borate, sodium chloride, sodium citrate, sodium hyaluronate, sodium hydroxide, sodium lactate, sodium phosphate, sodium phosphate dibasic, sodium phosphate monobasic, sorbic acid, sorbitan tristearate, sorbitol, trehalose, tris hydrochloride, tromethamine, tyloxapol, zinc chloride, aminomethylpropanol, anhydrous liquid lanolin, ascorbic acid, benzalkonium chloride, benzalkonium chloride, borate buffer, boric acid, calcium chloride, Carbopol 980, cetalkonium chloride, chlorobutanol, lanolin alcohols, hyaluronan, lanolin alcohols, oxychloro complex, polysorbate 80, potassium chloride, edetate disodium, sorbic acid, or other ingredient.

Ophthalmic formulations of the compounds described herein often comprise lubricants, such as polyvinyl alcohol, povidone, carboxymethylcellulose sodium, glycerin, mineral oil, white petrolatum, light mineral oil, polyethylene glycol, propylene glycol, hypromellose, hydroxypropyl methylcellulose, carmellose sodium, or dextran.

Ophthalmic formulations of the compounds described herein often contain preservatives. In some embodiments, ophthalmic formulations comprise preservatives such as Dequest (e.g., Dequest 2000, 2066, 2066a, 2006, 2010), sodium perborate, Vanish (stabilized peroxy complex), benzalkonium chloride, polyquaternium-42, POLYQUAD (polyquaternium-1), or other preservative.

Ophthalmic formulations of the compounds described herein in some cases comprise steroids. For example, formulations comprise steroids (e.g., corticosteroids) such as dexamethasone, hydrocortisone, loteprednol, prednisolone, or other steroid. In some embodiments, ophthalmic formulations comprise dexamethasone.

Ophthalmic formulations of the compounds described herein optionally comprise immunosuppressants. In some embodiments, ophthalmic formulations comprise immunosuppressants including T-cell inhibitors, or other immunosuppressant. In some embodiments, ophthalmic formulations comprise cyclosporine A.

Ophthalmic formulations of the compounds in some instances comprise anti-inflammatory agents. In some embodiments, ophthalmic formulations comprise anti-inflammatory agents such as anti-inflammatory CD44, tacrolimus, voclosporin, anti-TNF-alpha agents, resolvins, lefitegrast, or other anti-inflammatory agent. In some embodiments, ophthalmic formulations comprise lefitegrast.

In some instances, ophthalmic formulations of the compounds described herein do not comprise preservatives.

Ophthalmic formulations of the compounds described herein often comprise ingredients to reduce redness or inflammation. Such ingredients include but are not limited to naphazoline, phenylephrine, tetrahydrozoline, or pharmaceutically acceptable salts thereof.

Opthamological formulations of the compounds described herein comprise combinations of one or more ingredients. In some embodiments, ophthalmic formulations comprise polyvinyl alcohol and Povidone. In some embodiments, ophthalmic formulations comprise carboxymethylcellulose sodium. In some embodiments, ophthalmic formulations comprise carboxymethylcellulose sodium and glycerin. In some embodiments, ophthalmic formulations comprise carboxymethylcellulose sodium, polysorbate 80, and glycerin. In some embodiments, ophthalmic formulations comprise glycerin. In some embodiments, ophthalmic formulations comprise mineral oil. In some embodiments, ophthalmic formulations comprise mineral oil and petrolatum. In some embodiments, ophthalmic formulations comprise mineral oil. In some embodiments, ophthalmic formulations comprise light mineral oil. In some embodiments, ophthalmic formulations comprise light mineral oil and mineral oil. In some embodiments, ophthalmic formulations comprise white petrolatum. In some embodiments, ophthalmic formulations comprise polyethylene glycol. In some embodiments, ophthalmic formulations comprise polyethylene glycol 400. In some embodiments, ophthalmic formulations comprise polyethylene glycol 400 and propylene glycol. In some embodiments, ophthalmic formulations comprise propylene glycol. In some embodiments, ophthalmic formulations comprise hypromellose (such as 2910). In some embodiments, ophthalmic formulations comprise hydroxypropyl methylcellulose. In some embodiments, ophthalmic formulations comprise hydroxypropyl methylcellulose and dextran. In some embodiments, ophthalmic formulations comprise dextran. In some embodiments, ophthalmic formulations comprise dextran and hypromellose. In some embodiments, ophthalmic formulations comprise dextran, glycerin, and hypromellose. In some embodiments, ophthalmic formulations comprise polyethylene glycol 400, glycerin, and hypromellose. In some embodiments, ophthalmic formulations comprise polyvinyl pyrrolidone. In some embodiments, ophthalmic formulations comprise polyvinyl alcohol. In some embodiments, ophthalmic formulations comprise carmellose sodium. In some embodiments, ophthalmic formulations comprise polysorbate. In some embodiments, ophthalmic formulations comprise zinc sulfate. In some embodiments, ophthalmic formulations comprise Povidone. In some embodiments, ophthalmic formulations comprise hypromellose, naphazoline HCl, polysorbate 80, and zinc sulfate. In some embodiments, ophthalmic formulations comprise hypromellose, glycerin, and phenylephrine hydrochloride. In some embodiments, ophthalmic formulations comprise hypromellose, glycerin, polyethylene glycol, tetrahydrozoline HCl, and zinc sulfate.

In yet another embodiment, exemplary (non-limiting) ophthalmic formulations 1-57 of Table 2 further comprise a compound described herein.

TABLE 2

| Formula # | Ingredients A | Ingredients B |
|---|---|---|
| 1 | Polyvinyl Alcohol 1.4% Povidone 0.6% | Purified water, sodium chloride. |
| 2 | Carboxymethylcellulose Sodium | Oxychloro complex, Sodium Borate decahydrate, Sodium chloride, Potassium chloride, Calcium chloride dihydrate, Magnesium chloride hexahydrate, Boric acid. |
| 3 | Carboxymethylcellulose sodium 0.5% | Calcium chloride; magnesium chloride; potassium chloride; purified water; sodium chloride; and sodium lactate. |
| 4 | Carboxymethylcellulose sodium 0.5%, Glycerin 0.9% | Boric acid; calcium chloride dihydrate; erythritol; levocarnitine; magnesium chloride hexahydrate; potassium chloride; purified water; sodium borate decahydrate; and sodium citrate dihydrate. |
| 5 | Carboxymethylcellulose sodium 0.5%, Glycerin 0.9% | Boric acid; calcium chloride dihydrate; erythritol; levocarnitine; magnesium chloride hexahydrate; potassium chloride; purified water; PURITE ® (stabilized oxychloro complex); sodium borate decahydrate; and sodium citrate dihydrate. |
| 6 | Carboxymethylcellulose sodium 0.5% Glycerin 1% Polysorbate 80 0.5% | Boric acid; carbomer copolymer type A; castor oil; erythritol; levocarnitine; purified water; and sodium hydroxide. |
| 7 | Carboxymethylcellulose sodium 0.5% Glycerin 1% Polysorbate 80 0.5% | Boric acid; castor oil; erythritol; levocarnitine; carbomer copolymer type A; purified water; and PURITE ®(stabilized oxychloro complex). |
| 8 | Carboxymethylcellulose sodium 0.5% Glycerin 1% Polysorbate 80 0.5% | Boric acid; butylated hydroxyl toluene; castor oil; erythritol; flaxseed oil; levocarnitine; pemulen TR-2; polyoxyl 40 stearate; purified water; sodium hydroxide; trehalose. |
| 9 | Carboxymethylcellulose sodium 1% | Calcium chloride, potassium chloride, purified water, sodium chloride, and sodium lactate. |
| 10 | Carboxymethylcellulose sodium 10 mg in 1 mL, glycerin 9 mg in 1 mL | Boric acid; calcium chloride dihydrate; erythritol; levocarnitine; magnesium chloride hexahydrate; potassium chloride; PURITE ® (stabilized oxychloro complex); sodium borate decahydrate; sodium citrate dihydrate; purified water. |
| 11 | Mineral Oil 42.5% White Petrolatum 57.3% | Lanolin alcohols |
| 12 | Mineral Oil 42.5% White Petrolatum 56.8% | Chlorobutanol and lanolin alcohols. |
| 12 | Carboxymethylcellulose sodium 1% | Boric acid, calcium chloride, magnesium chloride, potassium chloride, purified water, PURITE ® (stabilized oxychloro complex), sodium borate, and sodium chloride. |
| 13 | Polyethylene Glycol 400 0.4%, Propylene Glycol 0.3% | Aminomethylpropanol, boric acid, hydroxypropyl guar, potassium chloride, purified water, sodium chloride, sorbitol. |
| 14 | Polyethylene Glycol 400 0.4%, Propylene Glycol 0.3% | Aminomethylpropanol, boric acid, hydroxypropyl guar, POLYQUAD ® (polyquaternium-1) 0.001% preservative, potassium chloride, purified water, sodium chloride, sorbitol. |
| 15 | Propylene Glycol 0.6% | Boric acid, dimyristoyl phosphatidylglycerol, edetate disodium, hydroxypropyl guar, mineral oil, polyoxyl 40 stearate, POLYQUAD ® (polyquaternium-1) 0.001% preservative, sorbitan tristearate, sorbitol and purified water. |
| 16 | Polyethylene Glycol 400 0.4%, Propylene Glycol 0.3% | Boric acid, calcium chloride, hydroxypropyl guar, magnesium chloride, potassium chloride, purified water, sodium chloride, zinc chloride. |
| 17 | White petrolatum 94% Mineral oil 3% | Anhydrous Liquid Lanolin 3%. |
| 18 | Hypromellose (0.3%) | Carbopol 980, phosphonic acid, purified water, sodium perborate and sorbitol. |
| 19 | Polyethylene Glycol 400 0.4%, Propylene Glycol 0.3% | Aminomethylpropanol, boric acid, edetate disodium, hydroxypropyl guar, POLYQUAD ® (polyquaternium-1) 0.001% preservative, potassium chloride, sodium chloride, sorbitol and purified water. |
| 20 | Polyethylene Glycol 400 0.4% Lubricant Propylene Glycol 0.3% | Aminomethylpropanol, boric acid, hydroxypropyl guar, POLYQUAD ® (polyquaternium-1) 0.001% preservative, potassium chloride, purified water, sodium chloride, sorbitol. |
| 21 | dextran, hydroxypropyl methylcellulose | sodium chloride, potassium chloride, with edetate disodium 0.1% and POLYQUAD ® (polyquaternium-1) |
| 22 | Hypromellose 0.2% | Boric acid, calcium chloride dihydrate, GenAqua (sodium perborate), phosphonic acid, potassium chloride, purified water, and sodium chloride |

TABLE 2-continued

| Formula # | Ingredients A | Ingredients B |
|---|---|---|
| 23 | Dextran 70 0.1%, Glycerin 0.2%, Hypromellose 0.3% | Boric acid, calcium chloride, glycine, hydrochloric acid and/or sodium hydroxide (to adjust pH), magnesium chloride, POLYQUAD ® (polyquaternium-1) 0.001% preservative, polysorbate 80, potassium chloride, purified water, sodium chloride, zinc chloride. |
| 24 | Hypromellose 0.3%. | carbopol 980, phosphoric acid, purifed water, sodium hydroxide, sodium perborate, and sorbitol |
| 25 | White petrolatum 93% Mineral oil 4% | anhydrous liquid lanolin |
| 26 | Dextran 70 0.1%, Hypromellose 2910 0.3% | Potassium Chloride, Purified Water, Sodium Borate, Sodium Chloride |
| 27 | Dextran 70 0.1%, Hypromellose 2910 0.3% | Calcium chloride, magnesium chloride, potassium chloride, purified water, sodium bicarbonate, sodium chloride, zinc chloride |
| 28 | Light mineral oil (1.0%), Mineral oil (4.5%) | boric acid, edetate disodium, octoxynol-40, polyquaternium-1 (preservative), polysorbate 80, purified water, sodium borate decahydrate |
| 29 | Povidone (2.0%) | benzalkonium chloride (0.005%), boric acid, edetate disodiumdihydrate, purified water, sodium borate, sodium chloride, tyloxapol. |
| 30 | Povidone (1.25%) | boric acid, potassium chloride, sodium borate and sodium chloride; preserved with edetate disodium 0.1% and sorbic acid 0.1% |
| 31 | Glycerin (0.6%) Propylene Glycol (0.6%) | boric acid, hydroxyalkylphosphonate, purified water, sodium alginate, sodium borate |
| 32 | Mineral oil (20%), White petrolatum (80%) | None |
| 33 | Glycerin (0.3%) Propylene glycol (1.0%) | benzalkonium chloride (0.01%), boric acid, edetate disodium, potassium chloride, purified water, sodium borate, sodium chloride. |
| 34 | Glycerin (0.2%) | Hyaluronan, sodium chloride, sodium phosphate dibasic, sodium phosphate monobasic, water. |
| 35 | Glycerin (0.2%) | Hyaluronan, sodium chloride, sodium phosphate dibasic, sodium phosphate monobasic, water. |
| 36 | Polyvinyl pyrrolidone 2.0%, Polyvinyl alcohol 2.7% | Boric acid, Disodium edetate dihydrate, Ethanol, Glycerin, Lecithin, Polixetonium, Polysorbate-80, Potassium chloride, Purified water, Sodium chloride |
| 37 | Light Mineral Oil (0.5) Mineral Oil (0.5%) | Cetalkonium chloride, glycerol, poloxamer 188, tris hydrochloride, tromethamine, tyloxapol, water for injection. |
| 38 | Hypromellose 0.3% | Citric acid, sodium citrate, sorbitol, water for injection. |
| 39 | Carboxymethylcellulose sodium 0.5% | Calcium chloride, magnesium chloride, potassium chloride, purified water, sodium chloride, sodium lactate. |
| 40 | Sodium Carboxymethyl Cellulose (0.25%) | Borate Buffers, Calcium Chloride, Dequest, Magnesium Chloride, Potassium Chloride, Purified Water, Sodium Bicarbonate, Sodium Chloride, Sodium Perborate, Sodium Phosphate |
| 41 | Sodium Carboxymethyl Cellulose (0.25%) | Borate Buffers, Calcium Chloride, Magnesium Chloride, Potassium Chloride, Purified Water, Sodium Bicarbonate, Sodium Chloride and Sodium Phosphate. |
| 42 | Sodium Carboxymethyl Cellulose (1%) | Borate Buffer, Calcium Chloride, Magnesium Chloride, Potassium Chloride, Water (Purified), Sodium Bicarbonate (Baking Soda), Sodium Chloride, Sodium Phosphate |
| 43 | Carmellose sodium | Borate Buffer, Sodium Chloride, Potassium Chloride, Sodium Bicarbonate (baking soda), Calcium Chloride, Magnesium Chloride, Sodium Phosphate, Sodium Perborate stabilized with phosphonic acid |
| 44 | Polyethylene Glycol 400 0.4%, Propylene Glycol 0.3% | Boric acid, castor oil, gellan gum, glycerin, hydroxyethylcellulose, polyoxyl 35 castor oil, polysorbate 80, sorbitol, tromethamine, Vanish (stabilized peroxy complex) and purified water. |
| 45 | Polyethylene Glycol 400 0.4%, Propylene Glycol 0.3% | Boric acid, gellan gum, glycerin, hydroxyethylcellulose, polyoxyl 35 castor oil, polysorbate 80, sorbitol, tromethamine, and purified water. |
| 46 | Polyethylene Glycol 400 0.4%, Propylene Glycol 0.3% | Boric acid, castor oil, gellan gum, glycerin, hydroxyethylcellulose, polyoxyl 35 castor oil, polysorbate 80, sorbitol, tromethamine, Vanish (stabilized peroxy complex) and purified water. |
| 47 | Glycerin 0.25% | Boric acid, purified water, sodium borate, sodium chloride, sodium hyaluronate |
| 48 | Polyvinyl alcohol 0.5%, Povidone 0.6% | Benzalkonium Chloride, Dextrose, Edetate Disodium, Potassium Chloride, Purified Water, Sodium Bicarbonate, Sodium Chloride, Sodium Citrate, Sodium Phosphate (mono- and dibasic) |

TABLE 2-continued

| Formula # | Ingredients A | Ingredients B |
|---|---|---|
| 49 | Hypromellose 0.20%, Naphazoline HCl 0.025%, Polysorbate 80 0.50%, Zinc Sulfate 0.25% | Calcium Chloride, Citric Acid, Edetate Disodium, Magnesium Chloride, Potassium Chloride, Purified water, Sodium Citrate, Sodium Chloride, Sorbic Acid |
| 50 | Polyvinyl Alcohol 0.5%, Povidone 0.6%, Tetrahydrozoline Hydrochloride 0.05% | Benzalkonium Chloride, Dextrose, Dibasic Sodium Phosphate, Edetate Disodium, Monobasic Sodium Phosphate, Potassium Chloride, Purified Water, Sodium Bicarbonate, Sodium Chloride, Sodium Citrate |
| 51 | Phenylephrine Hydrochloride 0.10%, Glycerin 0.25%, Hypromellose 0.30%, Glycerin 0.2%, Hypromellose 0.2% | Citric Acid, Purified Water, Sodium Chloride, Sodium Citrate Benzalkonium Chloride, Dextrose, Dibasic Sodium Phosphate, Edetate Disodium, Monobasic Sodium Phosphate, Potassium Chloride, Purified Water, Sodium Bicarbonate, Sodium Chloride, Sodium Citrate |
| 52 | Glycerin 0.2%, Hypromellose 0.36%, Polyethylene glycol 400 1% | ascorbic acid, boric acid, dextrose, glycine, magnesium chloride, polyquaternium-42, potassium chloride, purified water, sodium borate, sodium chloride, sodium citrate, sodium lactate, sodium phosphate dibasic |
| 53 | Glycerin 0.2%, Hypromellose 0.36%, Polyethylene glycol 400 1% | ascorbic acid, boric acid, dextrose, glycine, magnesium chloride, polyquaternium-42, potassium chloride, purified water, sodium borate, sodium chloride, sodium citrate, sodium lactate, sodium phosphate dibasic |
| 54 | Glycerin 0.2% Hypromellose 0.36% Polyethylene glycol 400 1% Tetrahydrozoline HCl 0.05% Zinc sulfate 0.25% | benzalkonium chloride, boric acid, edetate disodium, purified water, sodium chloride, sodium citrate |
| 55 | Lifitegrast 5% | sodium chloride, Dibasic Sodium Phosphate, sodium thiosulfate |
| 56 | Cyclosporine 0.05% | carbomer copolymer type A, castor oil, glycerin, polysorbate 80, purified water |
| 57 | Dexamethasone 0.01% Hypromellose 0.5% | benzalkonium chloride, sodium chloride, dibasic sodium phosphate, polysorbate 80, edetate disodium |

Methods of Dosing and Treatment Regimens

The dose of the composition comprising at least one compound as described herein differ, depending upon the patient's condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome), or a lessening of symptom severity. Optimal doses are generally determined using experimental models and/or clinical trials. The optimal dose depends upon the body mass, weight, or blood volume of the patient.

In one embodiment, the compounds described herein, or a pharmaceutically acceptable salt thereof, are used in the preparation of medicaments for the treatment of diseases or conditions in a mammal that would benefit from administration of any one of the compounds disclosed. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, in which the mammal previously experienced at least one symptom of the disease being treated and is currently in remission, a pharmaceutical composition comprising a compound described herein, or a pharmaceutically acceptable salt thereof, in order to prevent a return of the symptoms of the disease or condition.

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracistemal injection or infusion, subcutaneous injection, or implant), inhalation, nasal, vaginal, rectal, sublingual, ophthalmic, or topical (e.g., transdermal or local) routes of administration and can be formulated, alone or together, in suitable dosage unit with pharmaceutically acceptable excipients, carriers, adjuvants, and vehicles appropriate for each route of administration as described elsewhere herein.

In certain embodiments, compositions comprising the compounds described herein are administered ophthalmically. In some embodiments, compositions are administered directly to the ocular surface. In some embodiments, compositions are administered to the immediate vicinity of the ocular surface. In some embodiments, compositions are administered directly to the ocular surface or the immediate vicinity of the ocular surface. In some embodiments, compositions are administered by a dropper. Typical methods of ophthalmic administration of the compositions described herein include topical delivery, delivery to the back of the eye, intravitreal, or periocular administration. Dosages and the treatment regimen depend on variables such as the condition, patient, formulation, or other variables. For example, the composition formulated as eye drops can be administered as frequently as from 1 to 4 times a day or as infrequently as 1 to 4 times a week. In some embodiments the composition formulated as eye drops is administered 1 times per day. In some embodiments the composition formulated as eye drops is administered 2 times per day. In some embodiments the composition formulated as eye drops is administered no more than 5 times per day. In some embodiments the composition formulated as eye drops is administered no more than 2 times per day.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

Toxicity and therapeutic efficacy of such therapeutic regimens are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the ED50 with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; (f) administered ophthalmically to the mammal, and/or (g) administered non-systemically or locally to the mammal. In some embodiments, a compound of Formula (I), Formula (Ia-1), Formula (Ia-2), Formula (Ib), Formula (Ic), a pharmaceutically acceptable salt, solvate, polymorph, prodrug, metabolite, N-oxide, stereoisomer, or isomer thereof is administered orally or parenterally to the subject in need thereof. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration. In some embodiments, a compound of Formula (I), Formula (Ia-1), Formula (Ia-2), Formula (Ib), Formula (Ic), a pharmaceutically acceptable salt, solvate, polymorph, prodrug, metabolite, N-oxide, stereoisomer, or isomer thereof is administered orally or intravenously to a subject in need thereof. In some embodiments, a compound of Formula (I), Formula (Ia-1), Formula (Ia-2), Formula (Ib), Formula (Ic), a pharmaceutically acceptable salt, solvate, polymorph, prodrug, metabolite, N-oxide, stereoisomer, or isomer thereof is administered orally to a subject in need thereof. In some embodiments, a compound of Formula (I), Formula (Ia-1), Formula (Ia-2), Formula (Ib), Formula (Ic), a pharmaceutically acceptable salt, solvate, polymorph, prodrug, metabolite, N-oxide, stereoisomer, or isomer thereof is administered intravenously to a subject in need thereof.

In any of the aforementioned aspects are further embodiments comprising single administrations of the effective amount of the compound, including further embodiments in which (i) the compound is administered once a day; or (ii) the compound is administered to the mammal multiple times over the span of one day, e.g., two, three, four or more times daily. In some embodiments, the compounds described herein are administered daily, every other day, every other day 3 times a week, every 2 weeks, every 3 weeks, every 4 weeks, every 5 weeks, every 3 days, every 4 days, every 5 days, every 6 days, weekly, bi-weekly, 3 times a week, 4 times a week, 5 times a week, 6 times a week, once a month, twice a month, 3 times a month, once every 2 months, once every 3 months, once every 4 months, once every 5 months, or once every 6 months. In some embodiments, the compounds described herein, or a pharmaceutically acceptable salt, solvate, polymorph, prodrug, metabolite, N-oxide, stereoisomer, or isomer thereof, are administered daily.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours.

In certain embodiments wherein a patient's status does improve, the dose of drug being administered is temporarily reduced or temporarily suspended for a certain length of time (e.g., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 7 days. In one embodiment, the length of the drug holiday is 7 days. In one embodiment, the length of the drug holiday is 14 days. In one embodiment, the length of the drug holiday is 28 days.

Dietary Supplement Formulations and Methods

Disclosed herein are dietary supplement formulations and methods. These formulations and methods can be useful for helping individuals, among other things, to support a healthy lifestyle.

In one aspect, the dietary supplement formulations and methods described herein are useful for helping individuals reduce depression or anxiety, or associated symptoms such as sadness, lethargy, or general loss of interest in life.

In another aspect, the dietary supplement formulations and methods described herein are useful for supporting eye health. Eye health includes but is not limited to healthy visual acuity, night vision, and health of specific eye structures, such as retina or macula, tear production, or other eye-related health issue.

In some instances, the dietary supplement formulations and methods described herein support brain health. Brain health includes but is not limited to increased intelligence, improved communication and social skills, decreased risk of developmental delay, ADHD, autism, and cerebral palsy. The dietary supplement formulations and methods described herein are helpful for decreasing hyperactivity, impulsiveness, restlessness, and aggression in some instances. Other benefits include supporting a reduction in mood swings, or reduction of relapses in patients with schizophrenia or bipolar disorder. The dietary supplement formulations and methods described herein are also helpful for reducing age-related mental decline, or related diseases, such as Alzheimer's disease.

In other aspects, dietary supplement formulations and methods described herein support a healthy cardiovascular system. This includes but is not limited to a reduction in triglycerides, blood pressure, blood clots, arterial plaques, and inflammation. Additionally, dietary supplement formulations and methods described herein help support regulation of cholesterol levels, such as by increasing levels of high-density lipids (HDL).

In some cases, the dietary supplement formulations and methods described herein are used to support a healthy inflammatory response. This includes a reduction in inflammation, such as acute or chronic inflammation. Such dietary supplement formulations and methods in some instances support a reduction in molecules related to inflammation, such as eicosanoids and/or cytokines.

In some cases, the dietary supplement formulations and methods described herein are useful for regulating a healthy immune system. For example, healthy immune system regulation in some instances supports lowering the risk or symptoms of diseases such as diabetes, multiple sclerosis, lupus, rheumatoid arthritis, ulcerative colitis, Crohn's disease, or psoriasis.

The dietary supplement formulations and methods described herein are useful for supporting a reduced risk of cancer in some embodiments. For example, a reduced risk of colon cancer, prostate cancer, or breast cancer is supported.

The dietary supplement formulations and methods described herein are useful for supporting healthy respiratory health. For example, respiratory health in some instances includes asthma or associated symptoms such as coughing, shortness of breath, or wheezing.

The dietary supplement formulations and methods described herein are useful for maintaining a health liver. Liver health includes but is not limited to reducing fat in the liver, or helping conditions such as non-alcoholic fatty liver disease (NAFLD).

The dietary supplement formulations and methods described herein are useful for supporting healthy bone and joint health. Bone and join health variously comprise helping lower the risk of osteoporosis by increasing calcium levels, and/or reducing arthritis and increasing grip strength.

The dietary supplement formulations and methods described herein are useful for managing pain. For example, pain management comprises helping reduce lower abdominal or pelvic pain, such as menstrual pain.

The dietary supplement formulations and methods described herein are useful for supporting healthy sleep. Sleep health comprises length of sleep, quality of sleep, as well as regulation of sleep cycles. In some instances, sleep health comprises regulation of melatonin.

The dietary supplement formulations and methods described herein are useful for supporting healthy skin and cell membranes. Skin health variously comprises softness, wrinkle reduction, regulation of oil production, regulation of hydration, reduction of hyperkeratinization of hair follicles, reduction of premature aging, reduction of acne, and reduction or prevention of sun damage.

In some cases, dietary supplement formulations and methods support a healthy pregnancy, including prenatal development.

The compounds described herein may be combined with additional components to generate formulations. Such components may include excipients, vitamins, minerals, adaptogens, anti-oxidants, amino acids, or additional components A method of making a supplement formulation in unit dose form can comprise combining a compound described herein with omega-3 DHA, omega-3 EPA, phosphatidylcholine or a salt thereof, myo-inositol, choline, soy lecithin or a salt thereof, alpha-glycerophosphocholine or a salt thereof, phosphatidylserine or a salt thereof, citicoline or a salt thereof, L-arginine or a salt thereof, L-citrulline or a salt thereof, taurine or a salt thereof, beet root extract, acetyl-L-carnitine or a salt thereof, alpha lipoic acid or a salt thereof, resveratrol or a salt thereof, quercetin or a salt thereof, astaxanthin or a salt thereof, CoQ10, soybean oil, flax seed oil, turmeric root extract, boswellia extract, grape seed extract, rosemary leaf extract, cayenne pepper, ginkgo leaf extract, Korean ginseng root extract, and garlic bulb. A method of making a supplement formulation comprising the compounds described herein in unit dose form can comprise combining omega-3 DHA, omega-3 EPA, phosphatidylcholine or a salt thereof, myo-inositol, choline, soy lecithin or a salt thereof, alpha-glycerophosphocholine or a salt thereof, phosphatidylserine or a salt thereof, citicoline or a salt thereof, L-arginine or a salt thereof, L-citrulline or a salt thereof, taurine or a salt thereof, beet root extract, acetyl-L-carnitine or a salt thereof, alpha lipoic acid or a salt thereof, resveratrol or a salt thereof, quercetin or a salt thereof, astaxanthin or a salt thereof, CoQ10, soybean oil, flax seed oil, turmeric root extract, boswellia extract, grape seed extract, rosemary leaf extract, cayenne pepper, ginkgo leaf extract, Korean ginseng root extract, and garlic bulb, wherein the myo-inositol can be present in the formulation, individually, in each case, in an amount of from about 10 mg to about 160 mg.

Provided are methods comprising administration of at least one formulation described herein, wherein at least one formulation can be administered orally, intravenously, intraperitoneal, subcutaneous, topically, or a combination thereof. Optionally, at least one formulation can be administered as a pill, or as two or more pills. The two or more pills can be administered simultaneously, sequentially, or intermittently. At least one formulation can be administered as a powder formulation. At least one formulation can be administered as a combination of one or more pills and a powder formulation. The combination can be administered simultaneously, sequentially, or intermittently.

The formulations can be administered as tablets once or twice a day. More than one tablet can be administered at the same time. The formulation can be administered as capsules once or twice a day. More than one capsule can be administered at the same time. The formulation can be administered as liquid doses once or twice a day. More than one liquid dose can be administered at the same time. The compositions can be administered by inhalation once or twice a day.

At least one formulation can be administered as a liquid formulation. The liquid formulation can be obtained by reconstituting a powder formulation in a liquid. At least one formulation can be administered as a combination of one or more pills and a liquid formulation. The combination can be administered simultaneously, sequentially, or intermittently. At least one formulation can be administered as an emulsion formulation. At least one formulation can be administered as a combination of one or more pills and an emulsion formulation. The combination can be administered simultaneously, sequentially, or intermittently. At least one formulation can be mixed in food. The food can be a beverage, a shake, or a snack. The beverage can be tea, coffee, or energy drink. The food can be consumed by the subject as part of a meal or diet plan.

The following examples are set forth to illustrate more clearly the principle and practice of instances disclosed herein to those skilled in the art and are not to be construed as limiting the scope of any claimed instances. Unless otherwise stated, all parts and percentages are on a weight basis.

EXAMPLES

Example 1: Preparation of 15-(3-(3,4-bis(trifluoromethyl)benzyl)ureido)pentadecanoic Acid (Compound 110)

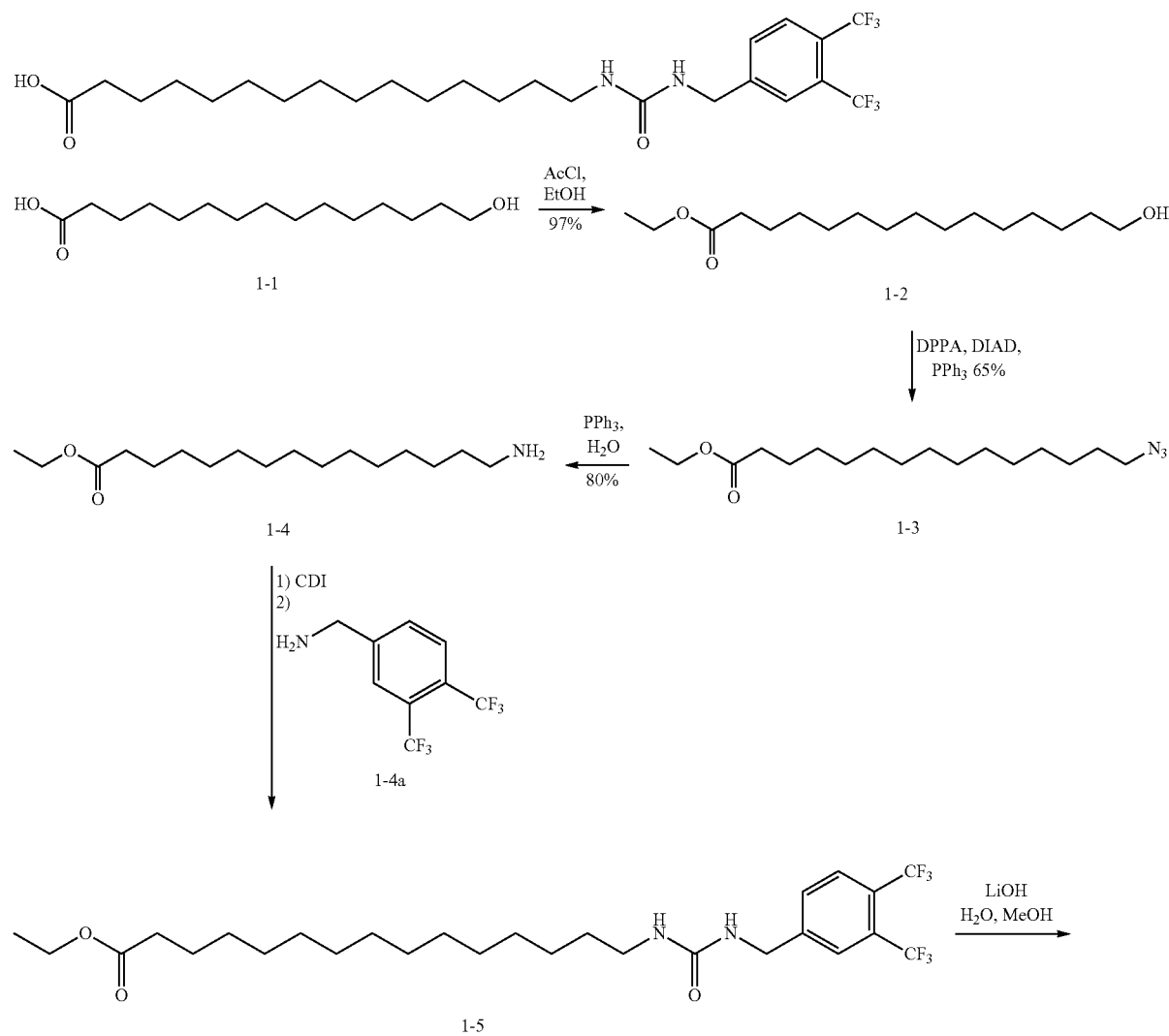

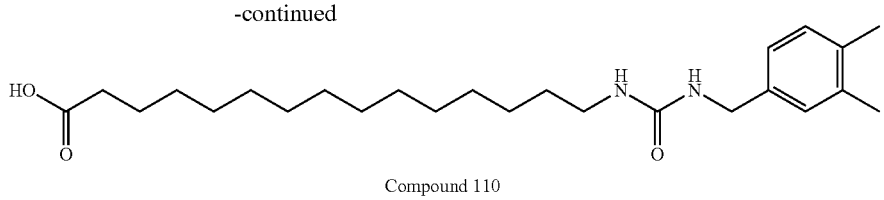

Compound 110

Step 1. 1-1 was reacted with acetyl chloride in ethanol to form ester 1-2 in 97% yield.

Step 2. 1-2 was reacted under Mitsunobu conditions with diisopropylazocarboxylate, diphenylphosphoryl azide, and triphenylphosphine to form azide 1-3 in 65% yield.

Step 3. 1-3 was reduced with triphenylphosphine in water to form amine 1-4 in 80% yield.

Step 4. 1-4 is reacted with carbonyldiimidazole, followed by amine 1-4a to form urea 1-5.

Step 5. 1-5 is reacted with LiOH in H₂O/methanol to generate Compound 110.

Example 2: Preparation of 15-((2-(4,4-difluoropip-eridin-1-yl)ethyl)sulfonamido)pentadecanoic Acid (Compound 111)

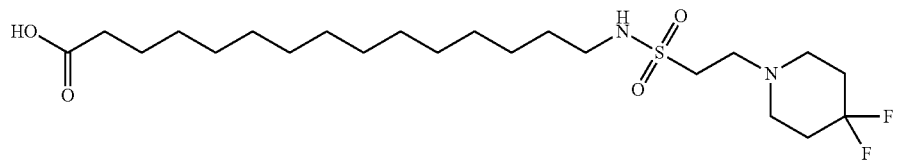

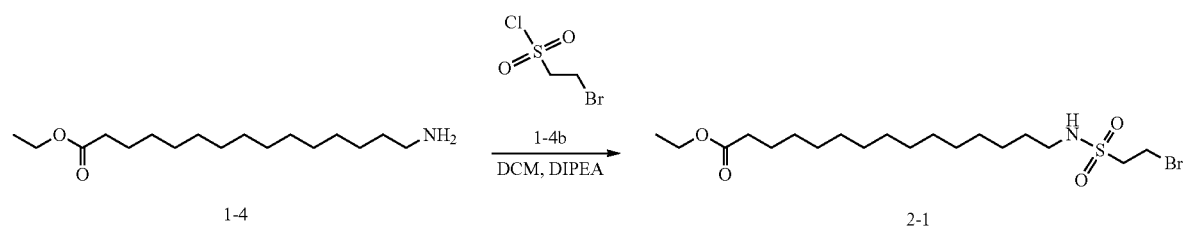

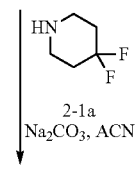

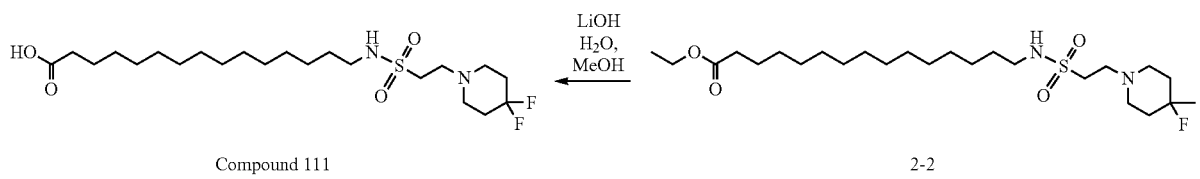

Step 1. 1-4 is reacted with chlorosulfonamide 1-4b and diisopropylethylamine in dichloromethane to form bromide 2-1.

Step 2. 2-1 is reacted with piperidine 2-1a and Na₂CO₃ in acetonitrile to form sulfonamide 2-2.

Step 3. 2-2 is reacted with LiOH in H₂O/methanol to generate Compound 111.

Example 3: Preparation of 9-(3-(3-(3,4-bis(trifluoromethyl)phenyl)ureido)propoxy)nonanoic Acid (Compound 91)

Step 4. 3-4 is reacted with carbonyldiimidazole, followed by amine 3-4a to form urea 3-5.

Step 5. 3-5 is reacted with LiOH in H₂O/methanol to generate Compound 91.

Example 4: In-Vivo Cancer Study of Compounds of Table 1

Breast tumour growth is evaluated in a nude mouse animal model with human MDA-MB-231 breast cancer cell xenografts. Tumors are generated by subcutaneous injection

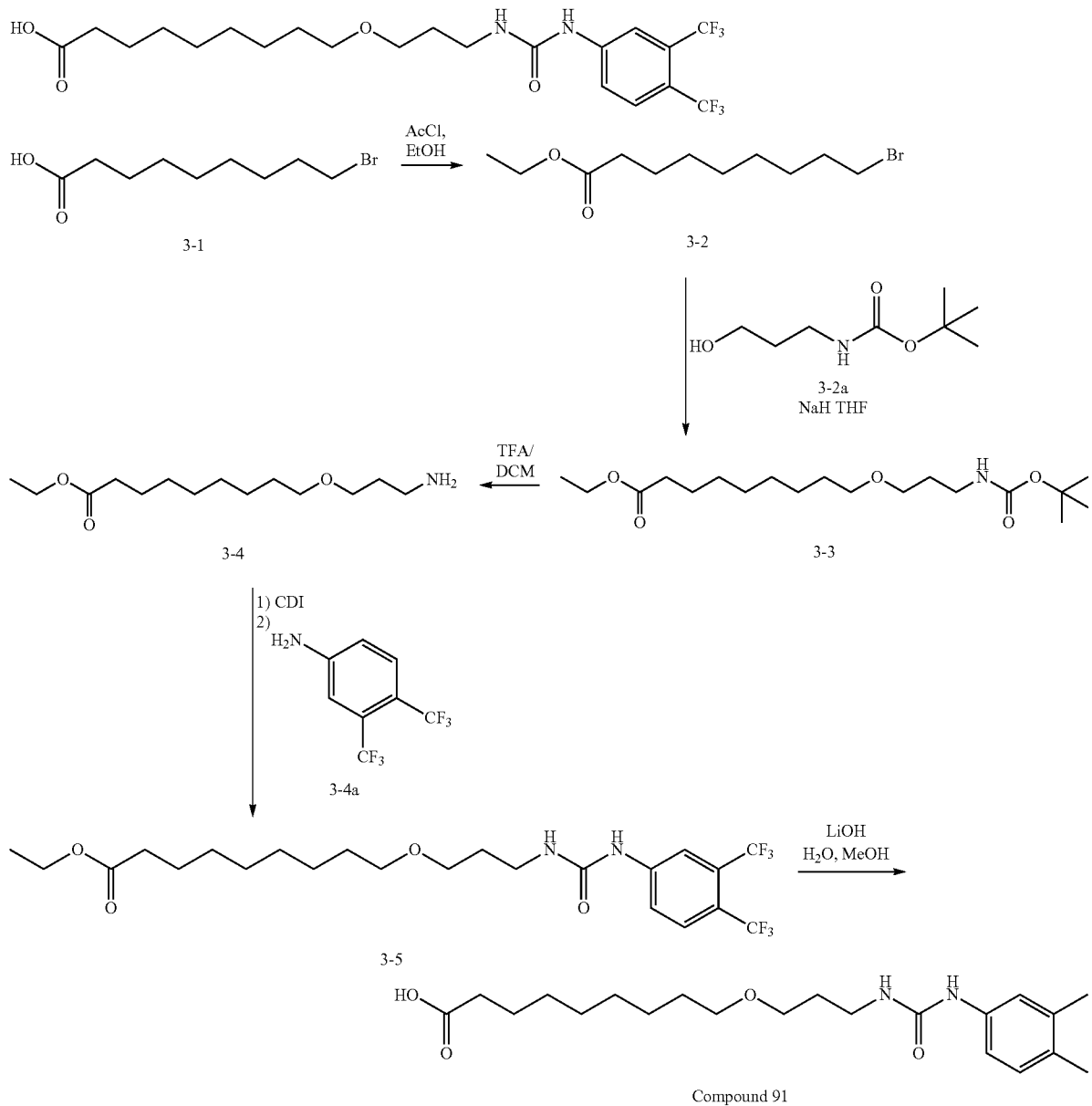

Step 1. 3-1 is reacted with acetyl chloride in ethanol to form ester 3-2.

Step 2. 3-2 is reacted with 3-2a and sodium hydride in THF to form 3-3.

Step 3. 3-3 is deprotected with trifluoroacetic acid in dichloromethane to form amine 3-4.

of 4×10⁵ cells/100 uL MDA-MB-231 cells into the mammary fat pad). Mice are divided into several treatment and control groups, with treatment groups receiving 2.5 mg/kg, 10 mg/kg or 40 mg/kg of a compound of Table 1 delivered as a DMSO intraperitoneal injection with an oil excipient. Compounds are injected once per day, six days a week for five weeks. Body weight and tumor size are measured daily to establish the effect of the compounds described herein on reducing tumor growth.

Example 5: Treatment of Dry Eye in Humans by Ophthalmic Administration

Adult patients aged between 35 and 65 years suffering from moderate to severe dry eye are treated with an ophthalmic formulation comprising any one of the compounds of Table 1. Such formulations are administered to the ocular surface or area adjacent to the ocular surface at intervals of once per day, twice per day, or four times per day. Subjects wearing contact lenses for the previous 30 days or during the study, those with chronic illness, or a history of glaucoma are excluded. The subjects are assessed before the study, at intervals during the study, such as every 2 weeks during the study, at the end of the treatment period, and 4 weeks after the last dose of the compound, for safety and pharmacodynamic evaluations. The evaluations include measurement of visual acuity, intraocular pressure, as well as scoring by imaging methods such as corneal staining, conjunctival staining, and ophthalmoscopy. Drug concentrations are also evaluated at these times points in samples obtained from plasma, urine, and tears.

We claim:

1. A compound of Formula (Ia-1) or (Ia-2), or a pharmaceutically acceptable salt, solvate, or stereoisomer thereof:

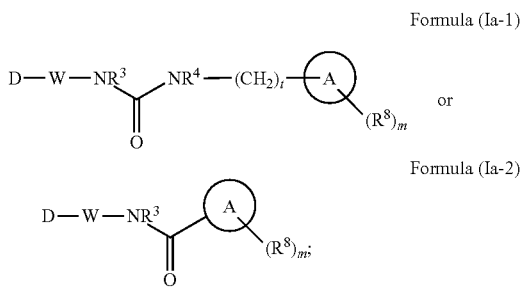

Formula (Ia-1)

Formula (Ia-2)

wherein:

D is —$CO_2H$ or —C(=O) $NR^7R^9$;

W is —$(CH_2)_p$-$(L)_n$-$(CH_2)_q$;

t is 0-2;

each L is independently —$(CR^1R^2)$—, —O-alkylene-, —$NR^7$-alkylene-, —S-alkylene-, —S(=O)-alkylene, or —S(=O)$_2$-alkylene wherein $R^1$ and $R^2$ are not both alkyl when the compound is of the Formula (Ia-1);

Ring A is substituted aryl, substituted heteroaryl, or substituted $C_2$-$C_8$ heterocycloalkyl wherein each of the substituents of the substituted aryl, substituted heteroaryl, or substituted $C_2$-$C_8$ heterocycloalkyl is itself unsubstituted; wherein if Ring A is heteroaryl or $C_2$-$C_8$ heterocycloakyl then at least one substituent of the substituted heteroaryl or the substituted $C_2$-$C_8$ heterocycloakyl is $CF_3$; and wherein if Ring A is substituted aryl then at least two substituent of the substituted aryl is each $CF_3$;

each $R^1$ or $R^2$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O) $NR^cR^d$, —OC(=O) $NR^cR^d$, —$NR^aC(=O) NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^3$ is hydrogen, —S(=O)$R^b$, —S(=O)$_2R^d$, —S(=O)$_2NR^cR^d$, —C(=O)$R^b$, —$CO_2R^a$, —C(=O) $NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

$R^4$ is hydrogen, —S(=O)$R^b$, —S(=O)$_2R^d$, —S(=O)$_2NR^cR^d$, —C(=O)$R^b$, —$CO_2R^a$, —C(=O) $NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

$R^7$ and $R^9$ are independently hydrogen;

each $R^8$ is independently hydrogen, —S(=O)$R^b$, —S(=O)$_2R^d$, —S(=O)$_2NR^cR^d$, —C(=O)$R^b$, —$CO_2R^a$, —C(=O) $NR^cR^d$, $C_1$-$C_6$ alkyl, $C_2$-$C_6$ alkenyl, $C_2$-$C_6$ alkynyl, $C_1$-$C_6$ heteroalkyl;

wherein the alkyl, alkenyl, alkynyl, and heteroalkyl is optionally substituted with one, two, or three of halogen, —$OR^a$, or —$NR^cR^d$, wherein $R^a$, $R^b$, $R^c$ and $R^d$ each is not $C_3$-$C_8$ cycloalkyl, $C_2$-$C_8$ heterocycloalkyl, aryl, or heteroaryl;

m is 1-5;

n is 0-3;

p is 0-9;

q is 0-5; and the atom chain connecting D and —$NR^3C$ (=O) $NR^4$— or —$NR^3C$(=O)— is 11, 12, 13, or 14 atoms.

2. The compound of claim 1, wherein D is —CO$_2$H.

3. The compound of claim 1, wherein D is —C(=O)NR$^7$R$^9$.

4. The compound of claim 1, wherein R$^1$ and R$^2$ are independently hydrogen, C$_1$-C$_6$ alkyl, C$_3$-C$_8$ cycloalkyl, or C$_1$-C$_6$ haloalkyl.

5. The compound of claim 1, wherein R$^1$ and R$^2$ are independently hydrogen.

6. The compound of claim 1, wherein R$^1$ and R$^2$ are hydrogen.

7. The compound of claim 1, wherein R$^3$ and R$^4$ are independently hydrogen, C$_1$-C$_6$ alkyl, C$_3$-C$_8$ cycloalkyl, or C$_1$-C$_6$ haloalkyl.

8. The compound of claim 1, wherein R$^3$ and R$^4$ are independently hydrogen.

9. The compound of claim 1, wherein R$^3$ and R$^4$ are H.

10. The compound of claim 1, or a pharmaceutically acceptable salt, solvate, or stereoisomer thereof, wherein the compound is selected from:

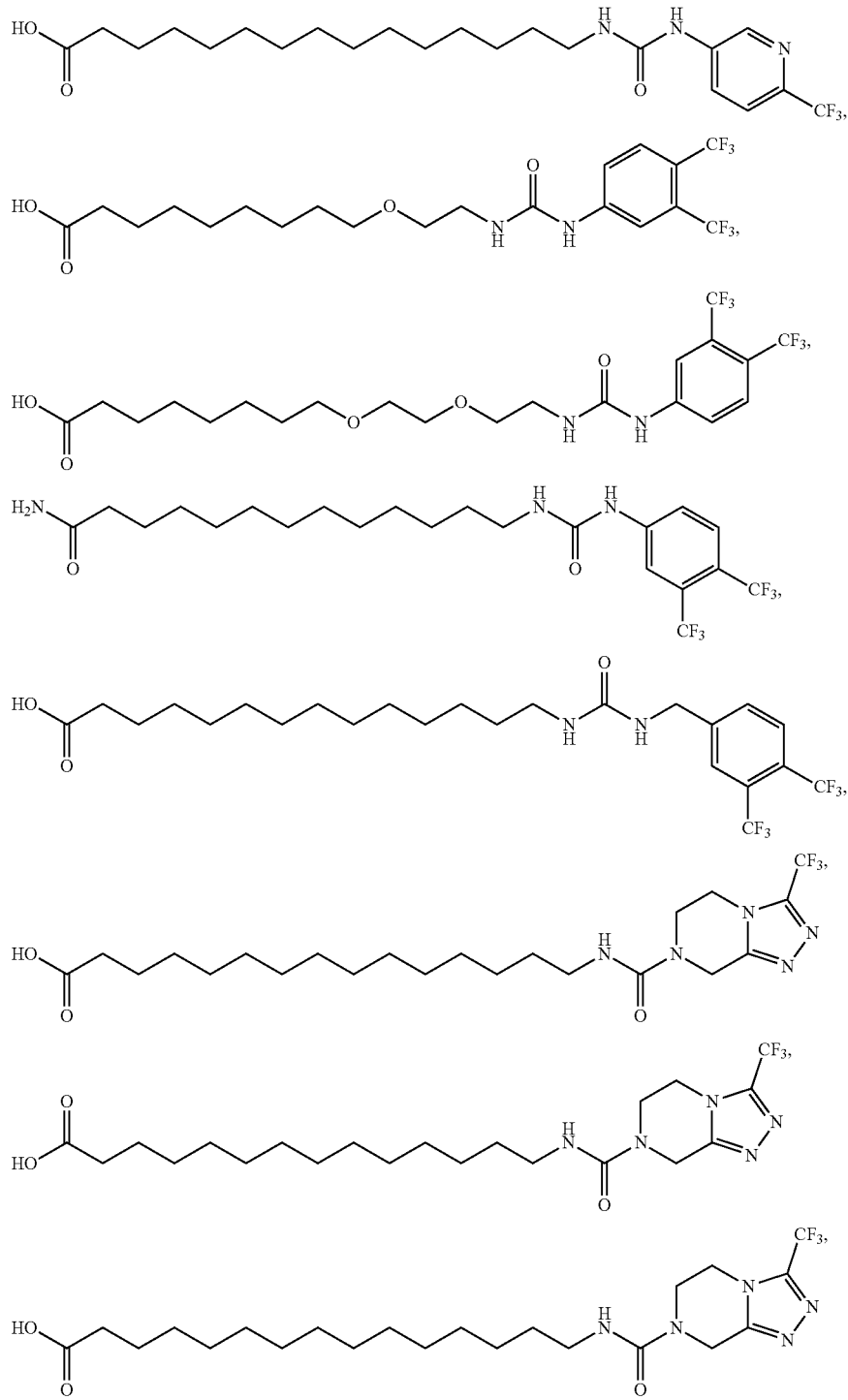

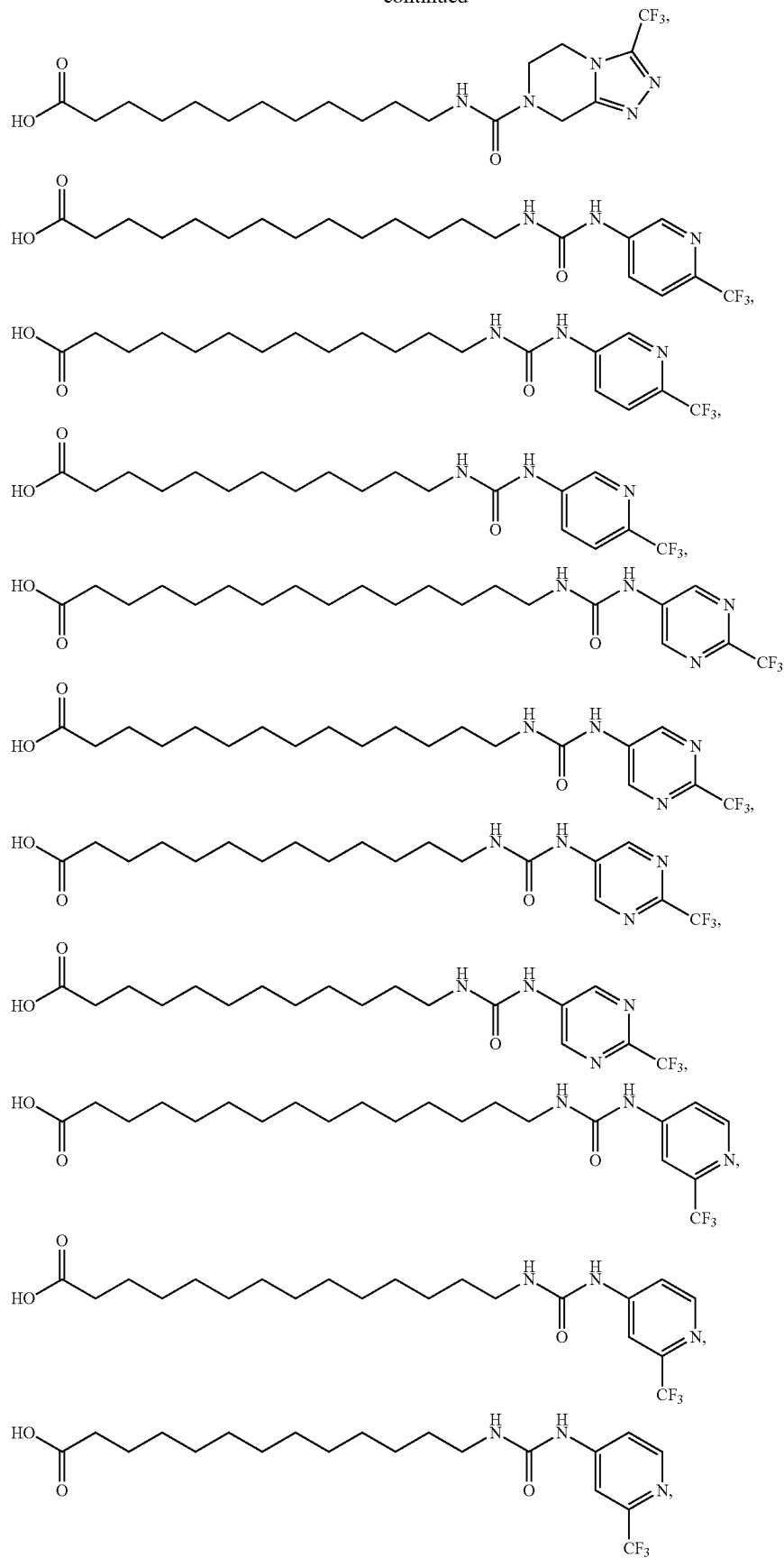

-continued
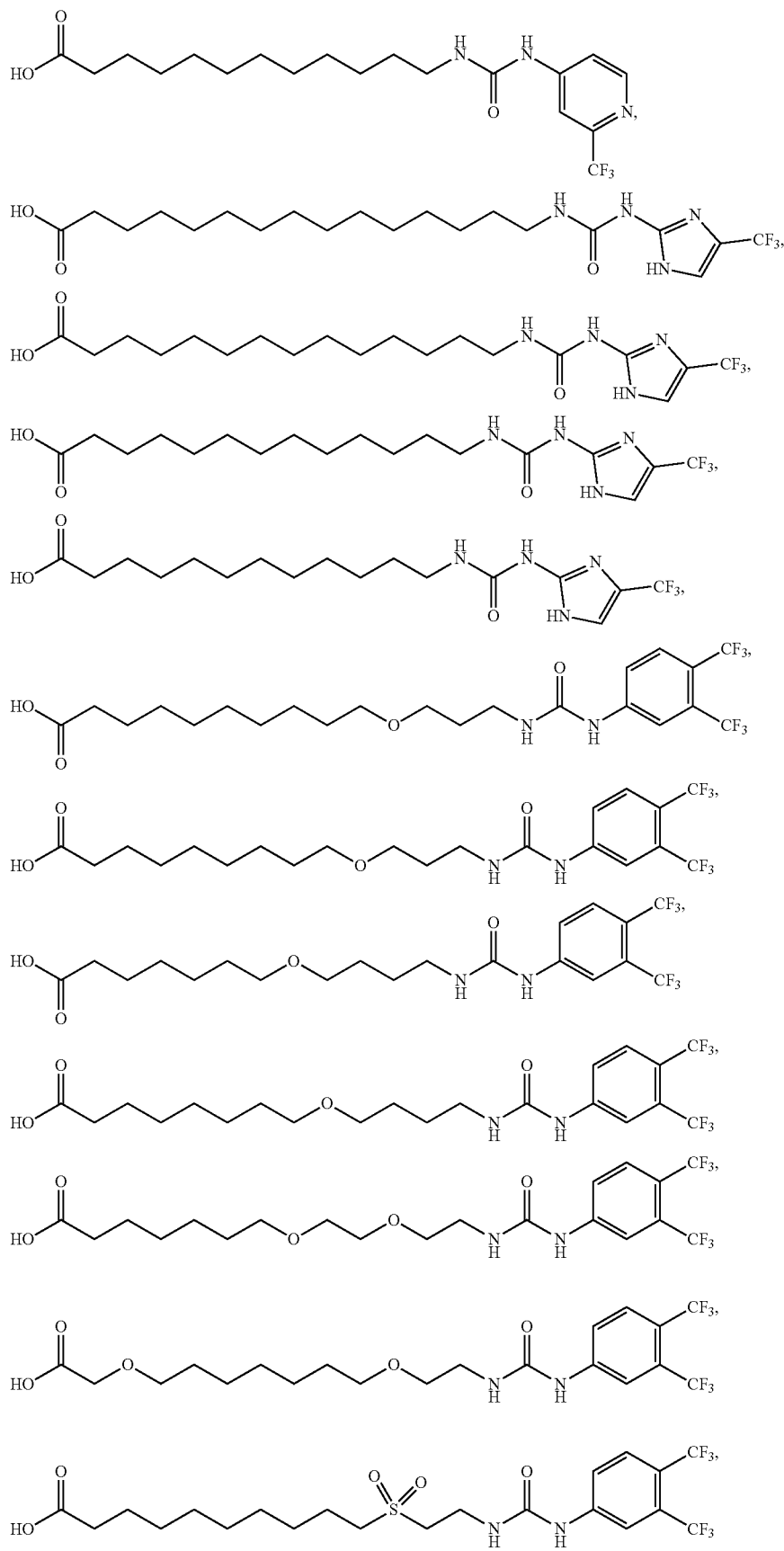

-continued

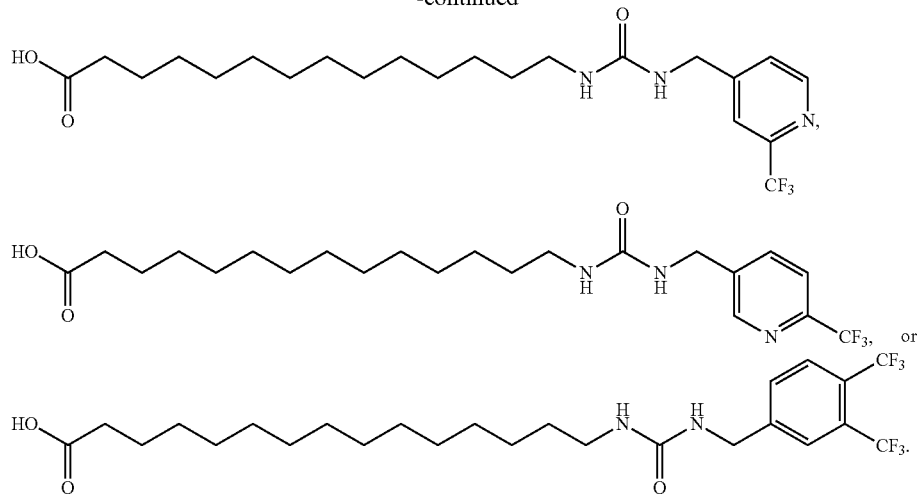

11. A pharmaceutical composition comprising a compound of claim 1, or a pharmaceutically acceptable salt, solvate, or stereoisomer thereof, and a pharmaceutically acceptable excipient.

12. The pharmaceutical composition of claim 11, wherein the pharmaceutical composition is formulated as a capsule.

13. A method of treating a proliferative disease, wherein the method comprises administering the compound or pharmaceutical composition of claim 1, or a pharmaceutically acceptable salt, solvate, or stereoisomer thereof to a subject in need thereof.

14. The method of claim 13, wherein the proliferative disease is cancer.

15. The method of claim 14, wherein the cancer is non-melanoma skin cancer, lung cancer, brain cancer, breast cancer, prostate cancer, colorectal cancer, bladder cancer, melanoma, non-Hodgkin lymphoma, kidney cancer, leukemia, pancreatic cancer, mesothelioma, head and neck cancer, gastric cancer, small cell lung cancer, or eye cancer.

* * * * *